(12) United States Patent
Han

(10) Patent No.: US 6,774,212 B2
(45) Date of Patent: Aug. 10, 2004

(54) ALPHA-KETOAMIDE INHIBITORS OF HEPATITIS C VIRUS NS3 PROTEASE

(75) Inventor: Wei Han, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 107 days.

(21) Appl. No.: 09/728,653

(22) Filed: Dec. 1, 2000

(65) Prior Publication Data

US 2002/0123468 A1 Sep. 5, 2002

Related U.S. Application Data

(60) Provisional application No. 60/168,998, filed on Dec. 3, 1999.

(51) Int. Cl.$^7$ .................................................. C07K 5/08
(52) U.S. Cl. ........................ 530/331; 530/330; 514/17; 514/18; 514/19
(58) Field of Search ................................ 530/328–331; 514/16–19

(56) References Cited

U.S. PATENT DOCUMENTS

| | | | | |
|---|---|---|---|---|
| 5,162,500 A | * | 11/1992 | Takeuchi et al. | ............ 530/330 |
| 5,541,290 A | * | 7/1996 | Harbeson et al. | ........... 530/330 |
| 6,291,640 B1 | * | 9/2001 | Bailey et al. | ................ 530/330 |

FOREIGN PATENT DOCUMENTS

| | | |
|---|---|---|
| EP | 0423358 | 4/1991 |
| EP | 0445467 | 9/1991 |
| WO | WO 92/12140 | 7/1992 |
| WO | WO 95/00535 | 1/1995 |
| WO | 96/16079 | * 5/1996 |
| WO | WO 98/17679 | 4/1998 |
| WO | WO 98/29435 | 7/1998 |
| WO | WO 98/50420 | 11/1998 |
| WO | WO 99/07733 | 2/1999 |
| WO | WO 99/07734 | 2/1999 |
| WO | WO 99/17790 | 4/1999 |

OTHER PUBLICATIONS

Bastos, Margarita (Proceedings of the National Academy of Sciences 92(15), 6738–42, 1995).*
Han, W. et al, Bioorg. Med. Chem. Lett., 10, 711–713, 2000.
Poynard, T. et al, Lancet 1998, 352, 1426–1432.

Myers, A. G. et al, J. Am. Chem. Soc. 1997, 119, 656–673.
Steinkuhler C. et al, Journal of Virology, 70, 6694–6700, 1996.
Steinkuhler C. et al, Journal of Biological Chemistry, 271, 6367–6373, 1996.
Sharpless, K. B. et al; Angew. Chem. Int. Ed. Engl. 1996, 34, 451.
Sharpless, K. B. et al, Angew. Chem. Int. Ed. Engl. 1996, 35, 2813.
Steven D. Young et al, Antimicrobial Agents and Chemotheraphy 1995, 2602–2605.
Andrew S. Thompson et al, Tet. Lett. 1995, 36, 8937–8940.
Bieth, Methods Enzymol., 248, 59–85, 1995.
Kaneko, S. K. et al, J. Org. Chem. 1993, 58, 2302.
Almeida, P. S. et al, Tetrahedron Lett. 1991, 23, 2671.
Angelastro, M. R., J. Med. Chem. 1990, 33, 13.
Chou and Talalay, Adv. Enzyme Regul. 1984, 22, 27–55.
The Peptides, vol. 3, 3–88 (1981).

* cited by examiner

Primary Examiner—Robert A. Wax
Assistant Examiner—David Lukton
(74) Attorney, Agent, or Firm—James Epperson; Scott K. Larsen

(57) ABSTRACT

The present invention relates to ketoamide and ketoester compounds of Formula (I):

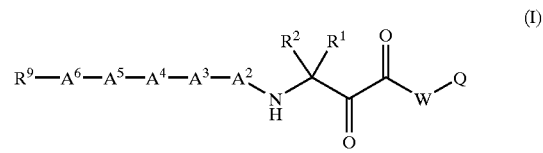

wherein W is —NH— or —O—, or stereoisomeric forms, stereoisomeric mixtures, or pharmaceutically acceptable salt forms thereof, which are useful as inhibitors of HCV NS3 protease, and to pharmaceutical compositions and diagnostic kits comprising the same, and methods of using the same for treating viral infection or as an assay standard or reagent.

6 Claims, No Drawings

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

<400> SEQUENCE: 1

Met Gly Ala Gln His
1               5

<210> SEQ ID NO 2
<211> LENGTH: 15
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

```
<400> SEQUENCE: 2

Met Arg Gly Ser His His His His His His Met Gly Ala Gln His
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Peptide ester substrate synthesized by methods
      disclosed in Taliani et al., Anal. Biochem., 240, 60-67, 1996.
<220> FEATURE:
<221> NAME/KEY: ACETYLATION
<222> LOCATION: (1)..(1)
<223> OTHER INFORMATION: acetyl group
<220> FEATURE:
<221> NAME/KEY: MOD_RES
<222> LOCATION: (3)..(3)
<223> OTHER INFORMATION: Aspartic acid modified with EDANS, 5-[(2'-
      aminoethyl)amino]naphthylene sulfonic acid
<220> FEATURE:
<221> NAME/KEY: MISC_FEATURE
<222> LOCATION: (6)..(6)
<223> OTHER INFORMATION: 2-amino butyric acid bonded through an ester
      group
<220> FEATURE:
<221> NAME/KEY: MOD_RES
<222> LOCATION: (9)..(9)
<223> OTHER INFORMATION: Lysine modified by Dabcyl; 4-[[4'(dimethyl-
      amino)phenyl]azo]benzoic acid

<400> SEQUENCE: 3

Asp Glu Asp Glu Glu Xaa Ala Ser Lys
1               5

<210> SEQ ID NO 4
<211> LENGTH: 4
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans
<220> FEATURE:
<221> NAME/KEY: ACETYLATION
<222> LOCATION: (1)..(1)
<223> OTHER INFORMATION: Acetylation
<220> FEATURE:
<221> NAME/KEY: AMIDATION
<222> LOCATION: (4)..(4)
<223> OTHER INFORMATION: para-nitroanaline

<400> SEQUENCE: 4

Glu Glu Ala Cys
1

<210> SEQ ID NO 5
<211> LENGTH: 6
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MISC_FEATURE
<222> LOCATION: (6)..(6)
<223> OTHER INFORMATION: Boro-allylglycine

<400> SEQUENCE: 5

Asp Glu Val Val Pro Xaa
1               5
```

```
<210> SEQ ID NO 6
<211> LENGTH: 23
<212> TYPE: PRT
<213> ORGANISM: Artificial Sequence
<220> FEATURE:
<223> OTHER INFORMATION: The synthesis of this peptide may be performed
      on an ABI 43A peptide synthesizer using readily available
      materials well known to ordinarily skilled artisans

<400> SEQUENCE: 6

Lys Lys Gly Ser Val Val Ile Val Gly Arg Ile Val Leu Ser Gly Lys
1               5                   10                  15

Pro Ala Ile Ile Pro Lys Lys
            20

<210> SEQ ID NO 7
<211> LENGTH: 6
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MISC_FEATURE
<222> LOCATION: (6)..(6)
<223> OTHER INFORMATION: Boro-allylglycine pinanediol ester

<400> SEQUENCE: 7

Asp Glu Val Val Pro Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: N-terminal Protecting Group: t-Butoxycarbonyl
      Delta-Carboxy Ester: t-Butyl
<220> FEATURE:
<221> NAME/KEY: MOD_RES
<222> LOCATION: (2)..(2)
<223> OTHER INFORMATION: Gamma-Carboxy Ester: t-Butyl

<400> SEQUENCE: 8

Asp Glu Val Val Pro
1               5

<210> SEQ ID NO 9
<211> LENGTH: 4
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: N-terminal Protecting Group: benzyloxycarbonyl
      Gamma-Carboxy Ester: t-Butyl
<220> FEATURE:
<221> NAME/KEY: MOD_RES
<222> LOCATION: (4)..(4)
<223> OTHER INFORMATION: Benzyl Esterfication

<400> SEQUENCE: 9
```

```
Glu Val Val Pro
1

<210> SEQ ID NO 10
<211> LENGTH: 4
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: Gamma-Carboxy Ester: t-Butyl

<400> SEQUENCE: 10

Glu Val Val Pro
1

<210> SEQ ID NO 11
<211> LENGTH: 6
<212> TYPE: PRT
<213> ORGANISM: Artificial Sequence
<220> FEATURE:
<223> OTHER INFORMATION: Synthesized by standard organic chemistry
      laboratory methods.
<220> FEATURE:
<221> NAME/KEY: MOD_RES
<222> LOCATION: (1)..(1)
<223> OTHER INFORMATION: N-terminal Protecting Group: t-Butoxycarbonyl
      Delta-Carboxy Ester: t-Butyl
<220> FEATURE:
<221> NAME/KEY: MOD_RES
<222> LOCATION: (2)..(2)
<223> OTHER INFORMATION: Gamma-Carboxy Ester: t-Butyl
<220> FEATURE:
<221> NAME/KEY: MISC_FEATURE
<222> LOCATION: (6)..(6)
<223> OTHER INFORMATION: Boro-allylglycine pinanediol ester

<400> SEQUENCE: 11

Asp Glu Val Val Pro Xaa
1               5
```

ALPHA-KETOAMIDE INHIBITORS OF HEPATITIS C VIRUS NS3 PROTEASE

This application claims the benefit of provisional application No. 60/168,998 filed on Dec. 3, 1999.

FIELD OF THE INVENTION

The present invention relates generally to a novel class of alpha-ketoamides which are useful as serine protease inhibitors, and more particularly as Hepatitis C virus NS3 protease inhibitors. This invention also relates to pharmaceutical compositions comprising these compounds and methods of using the same.

BACKGROUND OF THE INVENTION

Hepatitis C virus (HCV) is the major cause of transfusion and community-acquired non-A, non-B hepatitis worldwide. Approximately 2% of the world's population are infected with the virus. In the Unites States, hepatitis C represents approximately 20% of cases of acute hepatitis. Unfortunately, self-limited hepatitis is not the most common course of acute HCV infection. In the majority of patients, symptoms of acute hepatitis resolve, but alanine aminotransferase (a liver enzyme diagnostic for liver damage) levels often remain elevated and HCV RNA persists. Indeed, a propensity to chroninicity is the most distinguishing characteristic of hepatitis C, occurring in at least 85% of patients with acute HCV infection. The factors that lead to chronicity in hepatitis C are not well defined. Chronic HCV infection is associated with increased incidence of liver cirrhosis and liver cancer. No vaccines are available for this virus, and current treatment is restricted to the use of alpha interferon, which is effective in only 15–20% of patients. Recent clinical studies have shown that combination therapy of alpha interferon and ribavirin leads to sustained efficacy in 40% of patients (Poynard, T. et al. *Lancet* 1998, 352, 1426–1432.). However, a majority of patients still either fail to respond or relapse after completion of therapy. Thus, there is a clear need to develop more effective therapeutics for treatment of HCV-associated hepatitis.

HCV is a positive-stranded RNA virus. Based on comparison of deduced amino acid sequence and the extensive similarity in the 5' untranslated region, HCV has been classified as a separate genus in the Flaviviridae family, which also includes flaviviruses such as yellow fever virus and animal pestiviruses like bovine viral diarrhea virus and swine fever virus. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The RNA genome is about 9.6 Kb in length, and encodes a single polypeptide of about 3000 amino acids. The 5' untranslated region contains an internal ribosome entry site (IRES), which directs cellular ribosomes to the correct AUG for initiation of translation. As was determined by transient expression of cloned HCV cDNAs, the precursor protein is cotranslationally and posttranslationally processed into at least 10 viral structural and nonstructural (NS) proteins by the action of a host signal peptidase and by two distinct viral proteinase activities. The translated product contains the following proteins: core-E1-E2-p7-NS2-NS3-NS4A-NS4B-NS5A-NS5B.

The N-terminal portion of NS3 functions as a proteolytic enzyme that is responsible for the cleavage of sites liberating the nonstructural proteins NS4A, NS4B, NS5A, and NS5B. NS3 has further been shown to be a serine protease. Although the functions of the NS proteins are not completely defined, it is known that NS4A is a protease cofactor and NS5B is an RNA polymerase involved in viral replication. Thus agents that inhibit NS3 proteolytic processing of the viral polyprotein are expected to have antiviral activity.

There are several patents which disclose HCV NS3 protease inhibitors. WO98/17679 describes peptide and peptidomimetic ihibitors with the following formula: U-$E^8$-$E^7$-$E^6$-$E^5$-$E^4$—NH—CH($CH_2G^1$)-$W^1$, where W is one of a variety of electrophilic groups, including boronic acid or ester. E4 represents either an amino acid or one of a series of peptidomimetic groups, the sythesis of which are not exemplified. HCV protease inhibitors described in the present case are not covered.

Based on the large number of persons currently infected with HCV and the limited treatments available, it is desirable to discover new inhibitors of HCV NS3 protease.

SUMMARY OF THE INVENTION

Accordingly, one object of the present invention is to provide novel HCV NS3 protease inhibitors.

It is another object of the present invention to provide a novel method of treating HCV infection which comprises administering to a host in need of such treatment a therapeutically effective amount of at least one of the compounds of the present invention or a pharmaceutically acceptable salt form thereof.

It is another object of the present invention to provide pharmaceutical compositions with HCV NS3 protease inhibiting activity comprising a pharmaceutically acceptable carrier and a therapeutically effective amount of at least one of the compounds of the present invention or a pharmaceutically acceptable salt form thereof. It is another object of the present invention to provide a method of inhibiting HCV present in a body fluid sample which comprises treating the body fluid sample with an effective amount of a compound of the present invention. It is another object of the present invention to provide a kit or container containing at least one of the compounds of the present invention in an amount effective for use as a standard or reagent in a test or assay for determining the ability of a potential pharmaceutical to inhibit HCV NS3 protease, HCV growth, or both.

It is another object of the present invention to provide novel compounds for use in therapy.

It is another object of the present invention to provide the use of novel compounds for the manufacture of a medicament for the treatment of HCV.

These and other objects, which will become apparent during the following detailed description, have been achieved by the inventors' discovery that compounds of Formula (I):

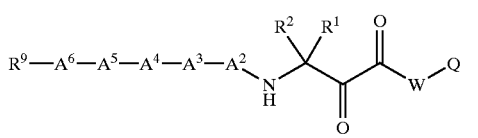

wherein W, Q, $R^1$, $R^2$, $A^2$, $A^3$, $A^4$, $A^5$, $A^6$, and $R^9$, are defined below, stereoisomeric forms, mixtures of stereoisomeric forms, or pharmaceutically acceptable salt forms thereof, are effective HCV NS3 protease inhibitors.

DETAILED DESCRIPTION OF PREFERRED EMBODIMENTS

[1] Thus, in a first embodiment, the present invention provides a novel compound of Formula I:

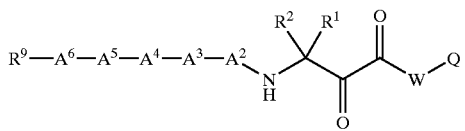

or a stereoisomer or pharmaceutically acceptable salt form thereof, wherein;

W is —NH— or —O—;
Q is selected from: —$(CR^{10}R^{10c})_n$—$Q^1$, —$(CR^{10}R^{10c})_n$—$Q^2$,
  $C_1$–$C_4$ alkyl substituted with $Q^1$,
  $C_2$–$C_4$ alkenyl substituted with $Q^1$,
  $C_2$–$C_4$ alkynyl substituted with $Q^1$, and
  an amino acid residue;
$Q^1$ is selected from:
  —$CO_2R^{11}$, —$SO_2R^{11}$, —$SO_3R^{11}$, —$P(O)_2R^{11}$, —$P(O)_3R^{11}$,
  aryl substituted with 0–4 $Q^{1a}$, and
  5–6 membered heterocyclic group consisting of carbon atoms and 1–4 heteroatoms selected from the group: O, S, and N, said heterocyclic group substituted with 0–4 $Q^{1a}$;
$Q^{1a}$ is H, F, Cl, Br, I, —$NO_2$, —CN, —NCS, —$CF_3$, —$OCF_3$, —$CH_3$, —$OCH_3$, —$CO_2R^{19}$, —$C(=O)NR^{19}R^{19}$, —$NHC(=O)R^{19}$, —$SO_2R^{19}$, —$SO_2NR^{19}R^{19}$, —$NR^{19}R^{19}$, —$OR^{19}$, —$SR^{19}$, $C_1$–$C_4$ alkyl, $C_1$–$C_4$ alkoxy, $C_1$–$C_4$ haloalkyl, or $C_1$–$C_4$ haloalkoxy;
$R^{19}$ is $C_1$–$C_4$ alkyl, $C_1$–$C_4$ haloalkyl, aryl, aryl($C_1$–$C_4$ alkyl), $C_3$–$C_6$ cycloalkyl, or $C_3$–$C_6$ cycloalkyl($C_1$–$C_4$ alkyl);
alternatively, $NR^{19}R^{19}$ may form a 5–6 membered heterocyclic group consisting of carbon atoms, a nitrogen atom, and optionally a second heteroatom selected from the group: O, S, and N;
$R^{10}$ is selected from the group: —$CO_2R^{11}$, —$NR^{11}R^{11}$, and $C_1$–$C_6$ alkyl substituted with 0–1 $R_{10a}$;
$R^{10a}$ is selected from the group: halo, —$NO_2$, —CN, —$CF_3$, —$CO_2R^{11}$, —$NR_{11}R^{11}$, —$OR^{11}$, —$SR^{11}$, —$C(=NH)NH_2$, and aryl substituted with 0–1 $R^{10b}$;
$R^{10b}$ is selected from the group: —$CO_2H$, —$NH_2$, —OH, —SH, and —$C(=NH)NH_2$;
$R^{10c}$ is H or $C_1$–$C_4$ alkyl;
alternatively, $R^{10}$ and $R^{10c}$ can be combined to form a $C_3$–$C_6$ cycloalkyl group substituted with 0–1 $R_{10a}$;

$R^{11}$ is, at each occurrence, independently H or $C_1$–$C_4$ alkyl;
$R^{11a}$ is H, $C_1$–$C_4$ alkyl, $C_1$–$C_4$ haloalkyl, $C_2$–$C_4$ alkenyl, $C_2$–$C_4$ alkynyl, aryl, aryl($C_1$–$C_4$ alkyl)-, $C_3$–$C_6$ cycloalkyl, or $C_3$–$C_6$ cycloalkyl($C_1$–$C_4$ alkyl)-;
$Q^2$ is —X—$NR^{12}$—Z, —$NR^{12}$—Y—Z, or —X—$NR^{12}$—Y—Z;
X is selected from the group: —C(=O)—, —S—, —S(=O)—, —S(=O)$_2$—, —P(O)—, —P(O)$_2$—, and —P(O)$_3$—; Y is selected from the group: —C(=O)—, —S—, —S(=O)—, —S(=O)$_2$—, —P(O)—, —P(O)$_2$—, and —P(O)$_3$—;
$R^{12}$ is H or $C_1$–$C_4$ alkyl;
Z is $C_1$–$C_4$ haloalkyl,
  $C_1$–$C_4$ alkyl substituted with 0–3 $Z^a$,
  $C_2$–$C_4$ alkenyl substituted with 0–3 $Z^a$,
  $C_2$–$C_4$ alkynyl substituted with 0–3 $Z^a$,
  $C_3$–$C_{10}$ cycloalkyl substituted with 0–5 $Z^b$,
  $C_3$–$C_{10}$ carbocyle substituted with 0–5 $Z^b$,
  aryl substituted with 0–5 $Z^b$,
  5–10 membered heterocyclic group consisting of carbon atoms and 1–4 heteroatoms selected from the group: O, S, and N, said heterocyclic group substituted with 0–4 $Z^b$;
  an amino acid residue, or
  —$A^7$—$A^8$—$A^9$;
$Z^a$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$,
  —$NR^{20}R^{20}$, —$OR^{20}$, —$SR^{20}$, —$S(=O)R^{20}$, —$SO_2R^{20}$, —$SO_2NR^{20}R^{20}$,
  $C_1$–$C_4$ alkyl, $C_1$–$C_4$ alkoxy, $C_1$–$C_4$ haloalkyl,
  $C_1$–$C_4$ haloalkoxy,
  $C_3$–$C_{10}$ cycloalkyl substituted with 0–5 $Z^b$,
  $C_3$–$C_{10}$ carbocyle substituted with 0–5 $Z^b$,
  aryl substituted with 0–5 $Z^b$, or
  5–10 membered heterocyclic group consisting of carbon atoms and 1–4 heteroatoms selected from the group: O, S, and N, said heterocyclic group substituted with 0–4 $Z^b$;
$Z^b$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$,
  —$NR^{20}R^{20}$, —$OR^{20}$, —$SR^{20}$, —$S(=O)R^{20}$, —$SO_2R^{20}$, —$SO_2NR^{20}R^{20}$,
  $C_1$–$C_4$ alkyl, $C_1$–$C_4$ alkoxy, $C_1$–$C_4$ haloalkyl,
  $C_1$–$C_4$ haloalkoxy,
  $C_3$–$C_{10}$ cycloalkyl substituted with 0–5 $Z^c$,
  $C_3$–$C_{10}$ carbocyle substituted with 0–5 $Z^c$,
  aryl substituted with 0–5 $Z^c$, or
  5–10 membered heterocyclic group consisting of carbon atoms and 1–4 heteroatoms selected from the group: O, S, and N, said heterocyclic group substituted with 0–4 $Z^c$;
$Z^c$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$,
  —$NR^{20}R^{20}$, —$OR^{20}$, —$SR^{20}$, —$S(=O)R^{20}$, —$SO_2R^{20}$, —$SO_2NR^{20}R^{20}$,
  $C_1$–$C_4$ alkyl, $C_1$–$C_4$ alkoxy, $C_1$–$C_4$ haloalkyl, or $C_1$–$C_4$ haloalkoxy;
$R^{20}$ is H, $C_1$–$C_4$ alkyl, $C_1$–$C_4$ haloalkyl, aryl, aryl($C_1$–$C_4$ alkyl)-, $C_3$–$C_6$ cycloalkyl, or $C_3$–$C_6$ cycloalkyl($C_1$–$C_4$ alkyl)-;

alternatively, $NR^{20}R^{20}$ may form a 5–6 membered heterocyclic group consisting of carbon atoms, a nitrogen atom, and optionally a second heteroatom selected from the group: O, S, and N;

$A^2$ is a bond, —NH—$CR^3R^4$—C(=O)—, an amino acid residue,

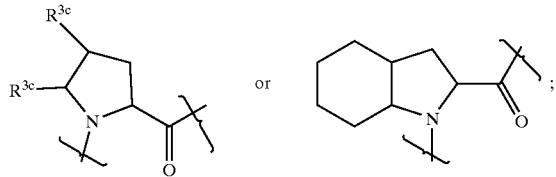

$A^3$ is a bond, —NH—$CR^5R^6$—C(=O)—, or an amino acid residue;

$A^4$ is a bond, —NH—$CR^7R^8$—C(=O)—, or an amino acid residue;

$A^5$ is a bond or an amino acid residue;

$A^6$ is a bond or an amino acid residue;

$A^7$ is a bond or an amino acid residue;

$A^8$ is an amino acid residue;

$A^9$ is an amino acid residue;

$R^1$ is selected from the group: H, F,
  $C_1$–$C_6$ alkyl substituted with 0–3 $R^{1a}$,
  $C_2$–$C_6$ alkenyl substituted with 0–3 $R^{1a}$,
  $C_2$–$C_6$ alkynyl substituted with 0–3 $R^{1a}$,
  aryl substituted with 0–5 $R^{1a}$, and
  $C_3$–$C_6$ cycloalkyl substituted with 0–3 $R^{1a}$;

$R^{1a}$ is selected at each occurrence from the group:
  Cl, F, Br, I, $CF_3$, $CHF_2$, OH, =O, SH, —$CO_2R^{1b}$, —$SO_2R^{1b}$,
  —$SO_3R^{1b}$, —$P(O)_2R^{1b}$, —$P(O)_3R^{1b}$, —C(=O)$NHR^{1b}$, —NHC(=O)$R^{1b}$,
  —$SO_2NHR^{1b}$, —$OR^{1b}$, —$SR^{1b}$, $C_1$–$C_3$ alkyl, $C_3$–$C_6$ cycloalkyl,
  $C_1$–$C_6$ alkoxy, —S—($C_1$–$C_6$ alkyl),
  aryl substituted with 0–5 $R^{1c}$,
  —O—$(CH_2)_q$-aryl substituted with 0–5 $R^{1c}$,
  —S—$(CH_2)_q$-aryl substituted with 0–5 $R^{1c}$, and
  5–10 membered heterocyclic group consisting of carbon atoms and 1–4 heteroatoms selected from the group: O, S, and N, and substituted with 0–3 $R^{1c}$;

$R^{1b}$ is H,
  $C_1$–$C_4$ alkyl substituted with 0–3 $R^{1c}$,
  $C_2$–$C_4$ alkenyl substituted with 0–3 $R^{1c}$,
  $C_2$–$C_4$ alkynyl substituted with 0–3 $R^{1c}$,
  $C_3$–$C_6$ cycloalkyl substituted with 0–5 $R^{1c}$,
  $C_3$–$C_6$ carbocyle substituted with 0–5 $R^{1c}$,
  aryl substituted with 0–5 $R^{1c}$, or
  5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from: $C_1$–$C_4$ alkyl, Cl, F, Br, I, OH, $C_1$–$C_4$ alkoxy, —CN, —$NO_2$, C(O)$OR^{1d}$, $NR^{1d}R^{1d}$, $CF_3$, and $OCF_3$;

$R^{1d}$ is H or $C_1$–$C_4$ alkyl;

$R^2$ is H, F, or $C_1$–$C_4$ alkyl;

$R^3$ is selected from the group: H,
  $C_1$–$C_6$ alkyl substituted with 0–4 $R^{3a}$,
  $C_2$–$C_6$ alkenyl substituted with 0–4 $R^{3a}$,
  $C_2$–$C_6$ alkynyl substituted with 0–4 $R^{3a}$,
  —$(CH_2)_q$—$C_3$–$C_6$ cycloalkyl substituted with 0–4 $R^{3b}$,
  —$(CH_2)_q$-aryl substituted with 0–5 $R^{3b}$, or
  —$(CH_2)_q$-5–10 membered heterocyclic group consisting of carbon atoms and 1–4 heteroatoms selected from the group: O, S, and N, and said heterocyclic group is substituted with 0–2 $R^{3b}$;

$R^{3a}$ is selected from the group: —$CO_2R^{11}$, —$NR^{11}R^{11}$, —$OR^{11}$, —$SR^{11}$, —C(=NH)$NH_2$, and aryl substituted with $R^{10b}$;

$R^{3b}$ is selected from the group: —$CO_2H$, —$NH_2$, —OH, —SH, and —C(=NH)$NH_2$;

$R^{3c}$ is, at each occurrence, independently selected from: H, $C_1$–$C_6$ alkyl, —OH, and $OR^{3d}$;

$R^{3d}$ is $C_1$–$C_6$ alkyl, $C_2$–$C_6$ alkenyl, $C_2$–$C_6$ alkynyl,
  —$(CH_2)_q$—$C_3$–$C_6$ cycloalkyl, —$(CH_2)_q$-aryl, or
  —$(CH_2)_q$-(5–10 membered heterocyclic group), wherein said heterocyclic group consists of carbon atoms and 1–4 heteroatoms selected from the group: O, S, and N;

$R^4$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^5$ and $R^7$ are independently H or $R^3$;

$R^6$ and $R^8$ are independently H or $R^4$;

$R^9$ is selected from the group: —S(=O)$R^{9a}$, —S(=O)$_2R^{9a}$, —C(=O)$R^{9a}$, —C(=O)$OR^{9a}$, —C(=O)$NHR^{9a}$, $C_1$–$C_3$ alkyl-$R^{9a}$,
  $C_2$–$C_6$ alkenyl-$R^{9a}$, and $C_2$–$C_6$ alkynyl-$R^{9a}$;

$R^{9a}$ is selected from the group:
  $C_1$–$C_6$ alkyl substituted with 0–3 $R^{9b}$,
  $C_3$–$C_6$ cycloalkyl substituted with 0–3 $R^{9c}$,
  aryl substituted with 0–3 $R^{9c}$, and
  5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group: phenyl, naphthyl, benzyl, and 5–10 membered heterocyclic group consisting of carbon atoms and 1–4 heteroatoms selected from the group: O, S, and N, and $R^{9b}$ is substituted with 0–3 $R^{9c}$;

$R^{9c}$ is selected at each occurrence from the group:
  $CF_3$, $OCF_3$, Cl, F, Br, I, =O, OH, phenyl, C(O)$OR^{11}$, $NH_2$, NH($CH_3$), N($CH_3$)$_2$, —CN, $NO_2$;
  $C_1$–$C_4$ alkyl substituted with 0–3 $R^{9d}$,
  $C_1$–$C_4$ alkoxy substituted with 0–3 $R^{9d}$,
  $C_3$–$C_6$ cycloalkyl substituted with 0–3 $R^{9d}$,
  aryl substituted with 0–5 $R^{9d}$, and
  5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:
  $C_1$–$C_4$ alkyl, $C_1$–$C_4$ alkoxy, $CF_3$, $OCF_3$, Cl, F, Br, I, =O, OH, phenyl, C(O)$OR^{11}$, $NH_2$, NH($CH_3$), N($CH_3$)$_2$, —CN, and $NO_2$;

an amino acid residue, at each occurence, independently comprises a natural amino acid, a modified amino acid or an unnatural amino acid wherein said natural, modified or unnatural amino acid is of either D or L configuration;

n is 1, 2, 3, or 4; and p is 1 or 2; and q, at each occurence, is independently 0, 1 or 2.

[2] In a preferred embodiment, the present invention provides novel compounds of Formula I, wherein:
Q is —$(CR^{10}R^{10c})_n$—$Q^2$ or
an amino acid residue, wherein the amino acid residue comprises a natural, a modified or an unnatural amino acid.

[3] In a more preferred embodiment, the present invention provides novel compounds of Formula II, wherein:

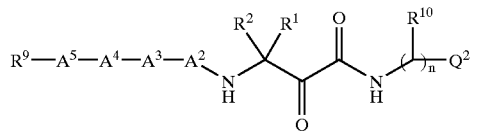

(II)

or a stereoisomer or pharmaceutically acceptable salt form thereof, wherein;

$R^{10}$ is selected from the group: —$CO_2R^{11}$, —$NR^{11}R^{11}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, —$NR^{11}R^{11}$, —$OR^{11}$, —$SR^{11}$, —C(=NH)$NH_2$, and aryl substituted with 0–1 $R^{10b}$;

$R^{10b}$ is selected from the group: —$CO_2H$, —$NH_2$, —OH, —SH, and —C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ is, at each occurrence, independently H or $C_1$–$C_4$ alkyl;

$R^{11a}$ is H, $C_1$–$C_4$ alkyl, $C_1$–$C_4$ haloalkyl, $C_2$–$C_4$ alkenyl, $C_2$–$C_4$ alkynyl, aryl, aryl($C_1$–$C_4$ alkyl)-, $C_3$–$C_6$ cycloalkyl, or $C_3$–$C_6$ cycloalkyl($C_1$–$C_4$ alkyl)-;

$Q^2$ is —X—$NR^{12}$—Z, —$NR^{12}$—Y—Z, or —X—$NR^{12}$—Y—Z;

X is selected from the group: —C(=O)—, —S—, —S(=O)—, —S(=O)$_2$—, —P(O)—, —P(O)$_2$—, and —P(O)$_3$—;

Y is selected from the group: —C(=O)—, —S—, —S(=O)—, —S(=O)$_2$—, —P(O)—, —P(O)$_2$—, and —P(O)$_3$—;

$R^{12}$ is H or $C_1$–$C_4$ alkyl;

Z is $C_1$–$C_4$ haloalkyl,
$C_1$–$C_4$ alkyl substituted with 0–3 $Z^a$,
$C_2$–$C_4$ alkenyl substituted with 0–3 $Z^a$,
$C_2$–$C_4$ alkynyl substituted with 0–3 $Z^a$,
$C_3$–$C_{10}$ cycloalkyl substituted with 0–5 $Z^b$,
$C_3$–$C_{10}$ carbocyle substituted with 0–5 $Z^b$,
aryl substituted with 0–5 $Z^b$,
5–10 membered heterocyclic group consisting of carbon atoms and 1–4 heteroatoms selected from the group: O, S, and N, said heterocyclic group substituted with 0–4 $Z^b$;
an amino acid residue, or
—$A^7$—$A^8$—$A^9$;

$Z^a$ is H, F, Cl, Br, I, —$NO_2$, —CN, —NCS, —$CF_3$, —$OCF_3$, —$CH_3$, —$OCH_3$, —$CO_2R^{20}$, —C(=O)$NR^{20}R^{20}$, —NHC(=O)$R^{20}$,
—$NR^{20}R^{20}$, —$OR^{20}$, —$SR^{20}$, —S(=O)$R^{20}$, —$SO_2R^{20}$, —$SO_2NR^{20}R^{20}$,
$C_1$–$C_4$ alkyl, $C_1$–$C_4$ alkoxy, $C_1$–$C_4$ haloalkyl,
$C_1$–$C_4$ haloalkoxy,
$C_3$–$C_{10}$ cycloalkyl substituted with 0–5 $Z^b$,
$C_3$–$C_{10}$ carbocyle substituted with 0–5 $Z^b$,
aryl substituted with 0–5 $Z^b$, or
5–10 membered heterocyclic group consisting of carbon atoms and 1–4 heteroatoms selected from the group: O, S, and N, said heterocyclic group substituted with 0–4 $Z^b$;

$Z^b$ is H, F, Cl, Br, I, —$NO_2$, —CN, —NCS, —$CF_3$, —$OCF_3$, —$CH_3$, —$OCH_3$, —$CO_2R^{20}$, —C(=O)$NR^{20}R^{20}$, —NHC(=O)$R^{20}$,
—$NR^{20}R^{20}$, —$OR^{20}$, —$SR^{20}$, —S(=O)$R^{20}$, —$SO_2R^{20}$, —$SO_2NR^{20}R^{20}$,
$C_1$–$C_4$ alkyl, $C_1$–$C_4$ alkoxy, $C_1$–$C_4$ haloalkyl,
$C_1$–$C_4$ haloalkoxy,
$C_3$–$C_{10}$ cycloalkyl substituted with 0–5 $Z^c$,
$C_3$–$C_{10}$ carbocyle substituted with 0–5 $Z^c$,
aryl substituted with 0–5 $Z^c$, or
5–10 membered heterocyclic group consisting of carbon atoms and 1–4 heteroatoms selected from the group: O, S, and N, said heterocyclic group substituted with 0–4 $Z^c$;

$Z^c$ is H, F, Cl, Br, I, —$NO_2$, —CN, —NCS, —$CF_3$, —$OCF_3$, —$CH_3$, —$OCH_3$, —$CO_2R^{20}$, —C(=O)$NR^{20}OR^{20}$, —NHC(=O)$R^{20}$,
—$NR^{20}R^{20}$, —$OR^{20}$, —$SR^{20}$, —S(=O)$R^{20}$, —$SO_2R^{20}$, —$SO_2NR^{20}R^{20}$,
$C_1$–$C_4$ alkyl, $C_1$–$C_4$ alkoxy, $C_1$–$C_4$ haloalkyl, or $C_1$–$C_4$ haloalkoxy;

$R^{20}$ is H, $C_1$–$C_4$ alkyl, $C_1$–$C_4$ haloalkyl, aryl, aryl($C_1$–$C_4$ alkyl)-, $C_3$–$C_6$ cycloalkyl, or
$C_3$–$C_6$ cycloalkyl($C_1$–$C_4$ alkyl)-;

alternatively, $NR^{20}R^{20}$ may form a 5–6 membered heterocyclic group consisting of carbon atoms, a nitrogen atom, and optionally a second heteroatom selected from the group: O, S, and N;

$A^2$ is a bond, —NH—$CR^3R^4$—C(=O)—, an amino acid residue,

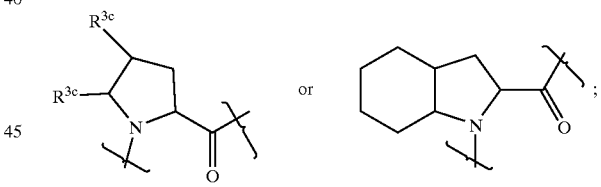

$A^3$ is a bond, —NH—$CR^5R^6$—C(=O)—, or an amino acid residue;
$A^4$ is a bond, —NH—$CR^7R^8$—C(=O)—, or an amino acid residue;
$A^5$ is a bond or an amino acid residue;
$A^7$ is a bond or an amino acid residue;
$A^8$ is an amino acid residue;
$A^9$ is an amino acid residue;
$R^1$ is selected from the group: H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH, —$CO_2R^{1b}$, —$SO_2R^{1b}$,
—$SO_3R^{1b}$, —P(O)$_2R^{1b}$, —P(O)$_3R^{1b}$, —C(=O)$NHR^{1b}$, —NHC(=O)$R^{1b}$, —$SO_2NHR^{1b}$, —$OR^{1b}$, —$SR^{1b}$, $C_1$–$C_3$ alkyl, $C_3$–$C_6$ cycloalkyl, $C_1$–$C_6$ alkoxy, —S—($C_1$–$C_6$ alkyl), aryl substituted with 0–5 $R^{1c}$, —O—$(CH_2)_q$-aryl substituted with 0–5 $R^{1c}$, —S—$(CH_2)_q$-aryl substituted with 0–5 $R^{1c}$, and 5–10 membered heterocyclic group consisting of carbon atoms and 1–4 heteroatoms selected from the group: O, S, and N, and substituted with 0–3 $R^{1c}$;

$R^{1b}$ is H, $C_1$–$C_4$ alkyl substituted with 0–3 $R^{1c}$, $C_2$–$C_4$ alkenyl substituted with 0–3 $R^{1c}$, $C_2$–$C_4$ alkynyl substituted with 0–3 $R^{1c}$, $C_3$–$C_6$ cycloalkyl substituted with 0–5 $R^{1c}$, $C_3$–$C_6$ carbocyle substituted with 0–5 $R^{1c}$, aryl substituted with 0–5 $R^{1c}$, or 5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from: $C_1$–$C_4$ alkyl, Cl, F, Br, I, OH, $C_1$–$C_4$ alkoxy, —CN, —$NO_2$, $C(O)OR^{1d}$, $NR^{1d}R^{1d}$, $CF_3$, and $OCF_3$;

$R^{1d}$ is H or $C_1$–$C_4$ alkyl;

$R^2$ is H, F, or $C_1$–$C_4$ alkyl;

$R^3$ is selected from the group: H, $C_1$–$C_6$ alkyl substituted with 0–4 $R^{3a}$, $C_2$–$C_6$ alkenyl substituted with 0–4 $R^{3a}$, $C_2$–$C_6$ alkynyl substituted with 0–4 $R^{3a}$, —$(CH_2)_q$—$C_3$–$C_6$ cycloalkyl substituted with 0–4 $R^{3b}$, —$(CH_2)_q$-aryl substituted with 0–5 $R^{3b}$, and —$(CH_2)_q$-5–10 membered heterocyclic group consisting of carbon atoms and 1–4 heteroatoms selected from the group: O, S, and N, and said heterocyclic group is substituted with 0–2 $R^{3b}$;

$R^{3a}$ is selected from the group: —$CO_2R^{11}$, —$NR^{11}R^{11}$, —$OR^{11}$, —$SR^{11}$, —C(=NH)$NH_2$, and aryl substituted with $R^{10b}$;

$R^{3b}$ is selected from the group: —$CO_2H$, —$NH_2$, —OH, —SH, and —C(=NH)$NH_2$;

$R^{3c}$ is, at each occurrence, independently selected from: H, $C_1$–$C_6$ alkyl, —OH, and $OR^{3d}$;

$R^{3d}$ is $C_1$–$C_6$ alkyl, $C_2$–$C_6$ alkenyl, $C_2$–$C_6$ alkynyl,

—$(CH_2)_q$—$C_3$–$C_6$ cycloalkyl, —$(CH_2)_q$-aryl, or

—$(CH_2)_q$-(5–10 membered heterocyclic group), wherein said heterocyclic group consists of carbon atoms and 1–4 heteroatoms selected from the group: O, S, and N;

$R^4$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^5$ and $R^7$ are independently H or $R^3$;

$R^6$ and $R^8$ are independently H or $R^4$;

$R^9$ is selected from the group: —S(=O)$R^{9a}$, —S(=O)$_2R^{9a}$, —C(=O)$R^{9a}$, —C(=O)$OR^{9a}$, —C(=O)$NHR^{9a}$, $C_1$–$C_3$ alkyl-$R^{9a}$, $C_2$–$C_6$ alkenyl-$R^{9a}$, and $C_2$–$C_6$ alkynyl-$R^{9a}$;

$R^{9a}$ is selected from the group:

$C_1$–$C_6$ alkyl substituted with 0–3 $R^{9b}$, $C_3$–$C_6$ cycloalkyl substituted with 0–3 $R^{9c}$, aryl substituted with 0–3 $R^{9c}$, and 5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group: phenyl, naphthyl, benzyl, and 5–10 membered heterocyclic group consisting of carbon atoms and 1–4 heteroatoms selected from the group: O, S, and N, and $R^{9b}$ is substituted with 0–3 $R^{9c}$;

$R^{9c}$ is selected at each occurrence from the group:

$CF_3$, $OCF_3$, Cl, F, Br, I, =O, OH, phenyl, C(O)$OR^{11}$, $NH_2$, NH($CH_3$), N($CH_3$)$_2$, —CN, $NO_2$;

$C_1$–$C_4$ alkyl substituted with 0–3 $R^{9d}$, $C_1$–$C_4$ alkoxy substituted with 0–3 $R^{9d}$, $C_3$–$C_6$ cycloalkyl substituted with 0–3 $R^{9d}$, aryl substituted with 0–5 $R^{9d}$, and 5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:

$C_1$–$C_4$ alkyl, $C_1$–$C_4$ alkoxy, $CF_3$, $OCF_3$, Cl, F, Br, I, =O, OH, phenyl, C(O)$OR^{11}$, $NB_2$, NH($CH_3$), N($CH_3$)$_2$, —CN, and $NO_2$;

n is 1, 2, or 3; and p is 1 or 2; and q, at each occurence, is independently 0, 1 or 2.

[4] In a further more preferred embodiment, the present invention provides novel compounds of Formula II, wherein:

$R^{10}$ is selected from the group: —$CO_2R^{11}$, —$NR^{11}R^{11}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, —$NR^{11}R^{11}$, —$OR^{11}$, —$SR^{11}$, —C(=NH)$NH_2$, and aryl substituted with 0–1 $R^{10b}$;

$R^{10b}$ is selected from the group: —$CO_2H$, —$NH_2$, —OH, —SH, and —C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ is, at each occurrence, independently H or $C_1$–$C_4$ alkyl;

$R^{11a}$ is H, $C_1$–$C_4$ alkyl, $C_1$–$C_4$ haloalkyl, $C_2$–$C_4$ alkenyl, $C_2$–$C_4$ alkynyl, aryl, aryl($C_1$–$C_4$ alkyl)-, $C_3$–$C_6$ cycloalkyl, or $C_3$–$C_6$ cycloalkyl($C_1$–$C_4$ alkyl)-;

$Q^2$ is —X—$NR^{12}$—Z, —$NR^{12}$—Y—Z, or —X—$NR^{12}$—Y—Z;

X is selected from the group: —C(=O)—, —S—, —S(=O)—, and —S(=O)$_2$—;

Y is selected from the group: —C(=O)—, —S—, —S(=O)—, and —S(=O)$_2$—;

$R^{12}$ is H or $C_1$–$C_4$ alkyl;

Z is $C_1$–$C_4$ haloalkyl, $C_1$–$C_4$ alkyl substituted with 0–3 $Z^a$, $C_2$–$C_4$ alkenyl substituted with 0–3 $Z^a$, $C_2$–$C_4$ alkynyl substituted with 0–3 $Z^a$, $C_3$–$C_{10}$ cycloalkyl substituted with 0–5 $Z^b$, $C_3$–$C_{10}$ carbocyle substituted with 0–5 $Z^b$, aryl substituted with 0–5 $Z^b$, 5–10 membered heterocyclic group consisting of carbon atoms and 1–4 heteroatoms selected from the group: O, S, and N, said heterocyclic group substituted with 0–4 $Z^b$;

an amino acid residue, or

—$A^7$—$A^8$—$A^9$;

$Z^a$ is H, F, Cl, Br, I, —$NO_2$, —CN, —NCS, —$CF_3$, —$OCF_3$, —$CH_3$, —$OCH_3$, —$CO_2R^{20}$, —C(=O)$NR^{20}R^{20}$, —NHC(=O)$R^{20}$,

—NR²⁰R²⁰, —OR²⁰, —SR²⁰, —S(=O)R²⁰, —SO₂R²⁰, —SO₂NR²⁰R²⁰, $C_1$–$C_4$ alkyl, $C_1$–$C_4$ alkoxy, $C_1$–$C_4$ haloalkyl, $C_1$–$C_4$ haloalkoxy, $C_3$–$C_{10}$ cycloalkyl substituted with 0–5 $Z^b$, $C_3$–$C_{10}$ carbocyle substituted with 0–5 $Z^b$, aryl substituted with 0–5 $Z^b$, or 5–10 membered heterocyclic group consisting of carbon atoms and 1–4 heteroatoms selected from the group: O, S, and N, said heterocyclic group substituted with 0–4 $Z^b$;

$Z^b$ is H, F, $C_1$, Br, I, —NO₂, —CN, —NCS, —CF₃, —OCF₃,

—CH₃, —OCH₃, —CO₂R²⁰, —C(=O)NR²⁰R²⁰, —NHC(=O)R²⁰,

—NR²⁰R²⁰, —OR²⁰, —SR²⁰, —S(=O)R²⁰, —SO₂R²⁰, —SO₂NR²⁰R²⁰, $C_1$–$C_4$ alkyl, $C_1$–$C_4$ alkoxy, $C_1$–$C_4$ haloalkyl, $C_1$–$C_4$ haloalkoxy, $C_3$–$C_{10}$ cycloalkyl substituted with 0–5 $Z^c$, $C_3$–$C_{10}$ carbocyle substituted with 0–5 $Z^c$, aryl substituted with 0–5 $Z^c$, or 5–10 membered heterocyclic group consisting of carbon atoms and 1–4 heteroatoms selected from the group: O, S, and N, said heterocyclic group substituted with 0–4 $Z^c$;

$Z^c$ is H, F, Cl, Br, I, —NO₂, —CN, —NCS, —CF₃, —OCF₃, —CH₃, —OCH₃, —CO₂R²⁰, —C(=O)NR²⁰R²⁰, —NHC(=O)R²⁰,

—NR²⁰R²⁰, —OR²⁰, —SR²⁰, —S(=O)R²⁰, —SO₂R²⁰, —SO₂NR²⁰R²⁰, $C_1$–$C_4$ alkyl, $C_1$–$C_4$ alkoxy, $C_1$–$C_4$ haloalkyl, or $C_1$–$C_4$ haloalkoxy;

R²⁰ is H, $C_1$–$C_4$ alkyl, $C_1$–$C_4$ haloalkyl, aryl, aryl($C_1$–$C_4$ alkyl)-, $C_3$–$C_6$ cycloalkyl, or $C_3$–$C_6$ cycloalkyl($C_1$–$C_4$ alkyl)-;

alternatively, NR²⁰R²⁰ may form a piperidinyl, piperazinyl, or morpholinyl group;

A² is a bond, —NH—CR³R⁴—C(=O)—, an amino acid residue,

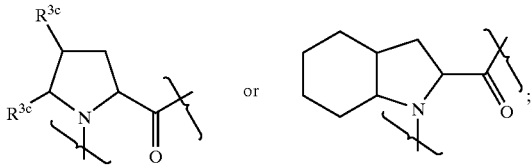

A³ is a bond or an amino acid residue;

A⁴ is a bond or an amino acid residue;

A⁵ is a bond;

R¹ is selected from the group: H, $C_1$–$C_6$ alkyl substituted with 0–3 $R^{1a}$, $C_2$–$C_6$ alkenyl substituted with 0–3 $R^{1a}$, $C_2$–$C_6$ alkynyl substituted with 0–3 $R^{1a}$, and $C_3$–$C_6$ cycloalkyl substituted with 0–3 $R^{1a}$;

$R^{1a}$ is selected at each occurrence from the group:

Cl, F, Br, I, CF₃, CHF₂, OH, =O, SH, —CO₂$R^{1b}$, —SO₂$R^{1b}$,

—SO₃$R^{1b}$, —P(O)₂$R^{1b}$, —P(O)₃$R^{1b}$, —C(=O)NHR$^{1b}$, —NHC(=O)R$^{1b}$,

—SO₂NHR$^{1b}$, —OR$^{1b}$, —SR$^{1b}$, $C_1$–$C_3$ alkyl, $C_3$–$C_6$ cycloalkyl, $C_1$–$C_6$ alkoxy, —S—($C_1$–$C_6$ alkyl), aryl substituted with 0–5 $R^{1c}$, —O—(CH₂)$_q$-aryl substituted with 0–5 $R^{1c}$, —S—(CH₂)$_q$-aryl substituted with 0–5 $R^{1c}$, and 5–10 membered heterocyclic group consisting of carbon atoms and 1–4 heteroatoms selected from the group: O, S, and N, and substituted with 0–3 $R^{1c}$;

$R^{1b}$ is H, $C_1$–$C_4$ alkyl substituted with 0–3 $R^{1c}$, $C_2$–$C_4$ alkenyl substituted with 0–3 $R^{1c}$, $C_2$–$C_4$ alkynyl substituted with 0–3 $R^{1c}$, $C_3$–$C_6$ cycloalkyl substituted with 0–5 $R^{1c}$, $C_3$–$C_6$ carbocyle substituted with 0–5 $R^{1c}$, aryl substituted with 0–5 $R^{1c}$, or 5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from: $C_1$–$C_4$ alkyl, Cl, F, Br, I, OH, $C_1$–$C_4$ alkoxy, —CN, —NO₂, C(O)OR$^{1d}$, NR$^{1d}$R$^{1d}$, CF₃, and OCF₃;

$R^{1d}$ is H or $C_1$–$C_4$ alkyl;

R² is H or $C_1$–$C_4$ alkyl;

R³ is selected from the group: H, $C_1$–$C_6$ alkyl substituted with 0–4 $R^{3a}$, $C_2$–$C_6$ alkenyl substituted with 0–4 $R^{3a}$, $C_2$–$C_6$ alkynyl substituted with 0–4 $R^{3a}$, —(CH₂)$_q$—$C_3$–$C_6$ cycloalkyl substituted with 0–4 $R^{3b}$, —(CH₂)$_q$-aryl substituted with 0–5 $R^{3b}$, and —(CH₂)$_q$-5–10 membered heterocyclic group consisting of carbon atoms and 1–4 heteroatoms selected from the group: O, S, and N, and said heterocyclic group is substituted with 0–2 $R^{3b}$;

$R^{3a}$ is selected from the group: —CO₂R¹¹, —NR¹¹R¹¹, —OR¹¹,

—SR¹¹, —C(=NH)NH₂, and aryl substituted with $R^{10b}$;

$R^{3b}$ is selected from the group: —CO₂H, —NH₂, —OH, —SH, and

—C(=NH)NH₂;

$R^{3c}$ is, at each occurrence, independently selected from: H, $C_1$–$C_6$ alkyl, —OH, and OR$^{3d}$;

$R^{3d}$ is $C_1$–$C_6$ alkyl, $C_2$–$C_6$ alkenyl, $C_2$–$C_6$ alkynyl,

—(CH₂)$_q$—$C_3$–$C_6$ cycloalkyl, —(CH₂)$_q$-aryl, or

—(CH₂)$_q$-(5–10 membered heterocyclic group), wherein said heterocyclic group consists of carbon atoms and 1–4 heteroatoms selected from the group: O, S, and N;

R⁴ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

R⁹ is selected from the group: —S(=O)₂R$^{9a}$, —C(=O)R$^{9a}$, $C_1$–$C_3$ alkyl-R$^{9a}$, $C_2$–$C_6$ alkenyl-R$^{9a}$, and $C_2$–$C_6$ alkynyl-R$^{9a}$;

$R^{9a}$ is selected from the group:

$C_1$–$C_6$ alkyl substituted with 0–3 $R^{9b}$, $C_3$–$C_6$ cycloalkyl substituted with 0–3 $R^{9c}$, aryl substituted with 0–3 $R^{9c}$, and 5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group: phenyl, naphthyl, benzyl, and 5–10 membered heterocyclic group consisting of carbon atoms and 1–4 heteroatoms selected from the group: O, S, and N, and $R^{9b}$ is substituted with 0–3 $R^{9c}$;

$R^{9c}$ is selected at each occurrence from the group:
$CF_3$, $OCF_3$, Cl, F, Br, I, =O, OH, phenyl, $C(O)OR^{11}$, $NH_2$, $NH(CH_3)$, $N(CH_3)_2$, —CN, $NO_2$;
$C_1$–$C_4$ alkyl substituted with 0–3 $R^{9d}$,
$C_1$–$C_4$ alkoxy substituted with 0–3 $R^{9d}$,
$C_3$–$C_6$ cycloalkyl substituted with 0–3 $R^{9d}$,
aryl substituted with 0–5 $R^{9d}$, and
5–6 membered heterocyclic group consisting of carbon atoms and 1–4 heteroatoms selected from the group: O, S, and N, and said heterocyclic group is substituted with 0–4 $R^{9d}$;

$R^{9d}$ is selected at each occurrence from the group:
$C_1$–$C_4$ alkyl, $C_1$–$C_4$ alkoxy, $CF_3$, $OCF_3$, Cl, F, Br, I, =O, OH, phenyl, $C(O)OR^{11}$, $NH_2$, $NH(CH_3)$, $N(CH_3)_2$, —CN, and $NO_2$;

n is 1 or 2; and
p is 1 or 2; and
q, at each occurence, is independently 0, 1 or 2.

[5] In an even more preferred embodiment, the present invention provides novel compounds of Formula III, wherein:

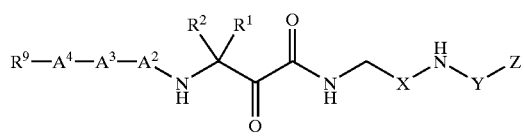

(III)

or a stereoisomer or pharmaceutically acceptable salt form thereof, wherein;
$R^{11}$ is, at each occurrence, independently H or $C_1$–$C_4$ alkyl;
X is —C(=O)—, —S—, —S(=O)—, or —S(=O)$_2$—;
Y is —C(=O)—or —S(=O)$_2$—;
Z is $C_1$–$C_4$ haloalkyl,
$C_1$–$C_4$ alkyl substituted with 0–3 $Z^a$,
$C_2$–$C_4$ alkenyl substituted with 0–3 $Z^a$,
$C_2$–$C_4$ alkynyl substituted with 0–3 $Z^a$,
$C_3$–$C_{10}$ cycloalkyl substituted with 0–5 $Z^b$,
$C_3$–$C_{10}$ carbocyle substituted with 0–5 $Z^b$,
aryl substituted with 0–5 $Z^b$, or
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; said heterocyclic group substituted with 0–4 $Z^b$;

$Z^a$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$,
—$NR^{20}R^{20}$, —$OR^{20}$, —$SR^{20}$, —$S(=O)R^{20}$, —$SO_2R^{20}$, —$SO_2NR^{20}R^{20}$,
$C_1$–$C_4$ alkyl, $C_1$–$C_4$ alkoxy, $C_1$–$C_4$ haloalkyl,
$C_1$–$C_4$ haloalkoxy,
$C_3$–$C_{10}$ cycloalkyl substituted with 0–5 $Z^b$,
$C_3$–$C_{10}$ carbocyle substituted with 0–5 $Z^b$,
aryl substituted with 0–5 $Z^b$, or
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; said heterocyclic group substituted with 0–4 $Z^b$;

$Z^b$ is H, F, Cl, Br, I, —$NO_2$, —CN, —NCS, —$CF_3$, —$OCF_3$, —$CH_3$, —$OCH_3$, —$CO_2R^{20}$, —$C(=O)NR^{20}R^{20}$, —$NHC(=O)R^{20}$,
—$NR^{20}R^{20}$, —$OR^{20}$, —$SR^{20}$, —$S(=O)R^{20}$, —$SO_2R^{20}$, —$SO_2NR^{20}R^{20}$,
$C_1$–$C_4$ alkyl, $C_1$–$C_4$ alkoxy, $C_1$–$C_4$ haloalkyl,
$C_1$–$C_4$ haloalkoxy,
$C_3$–$C_{10}$ cycloalkyl substituted with 0–5 $Z^c$,
$C_3$–$C_{10}$ carbocyle substituted with 0–5 $Z^c$,
aryl substituted with 0–5 $Z^c$, or
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; said heterocyclic group substituted with 0–4 $Z^c$;

$Z^c$ is H, F, Cl, Br, I, —$NO_2$, —CN, —NCS, —$CF_3$, —$OCF_3$, —$CH_3$, —$OCH_3$, —$CO_2R^{20}$, —$C(=o)NR^2OR^{20}$, —$NHC(=O)R^{20}$,
—$NR^{20}R^{20}$, —$OR^{20}$, —$SR^{20}$, —$S(=O)R^{20}$, —$SO_2R^{20}$, —$SO_2NR^{20}R^{20}$,
$C_1$–$C_4$ alkyl, $C_1$–$C_4$ alkoxy, $C_1$–$C_4$ haloalkyl, or $C_1$–$C_4$ haloalkoxy;

$R^{20}$ is H, $C_1$–$C_4$ alkyl, $C_1$–$C_4$ haloalkyl, aryl, aryl($C_1$–$C_4$ alkyl)-, $C_3$–$C_6$ cycloalkyl, or $C_3$–$C_6$ cycloalkyl($C_1$–$C_4$ alkyl)-;

alternatively, $NR^{20}R^{20}$ may form a piperidinyl, piperazinyl, or morpholinyl group;

$A^2$ is a bond, —NH—$CR^3R^4$—C(=O)—, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, Val,

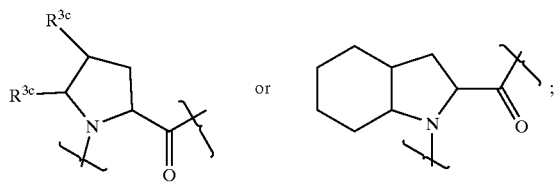

$A^3$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

$A^4$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

$R^1$ is selected from the group: H,
  $C_1$–$C_6$ alkyl substituted with 0–3 $R^{1a}$,
  $C_2$–$C_6$ alkenyl substituted with 0–3 $R^{1a}$,
  $C_2$–$C_6$ alkynyl substituted with 0–3 $R^{1a}$, and
  $C_3$–$C_6$ cycloalkyl substituted with 0–3 $R^{1a}$;

$R^{1a}$ is selected at each occurrence from the group:
  Cl, F, Br, I, $CF_3$, $CHF_2$, OH, =O, SH, —$CO_2R^{1b}$, —$SO_2R^{1b}$,
  —$SO_3R^{1b}$, —$P(O)_2R^{1b}$, —$P(O)_3R^{1b}$, —C(=O)$NHR^{1b}$, —NHC(=O)$R^{1b}$,
  —$SO_2NHR^{1b}$, —$OR^{1b}$, —$SR^{1b}$, $C_1$–$C_3$ alkyl, $C_3$–$C_6$ cycloalkyl,
  $C_1$–$C_6$ alkoxy, —S—($C_1$–$C_6$ alkyl),
  aryl substituted with 0–5 $R^{1c}$,
  —O—$(CH_2)_q$-aryl substituted with 0–5 $R^{1c}$,
  —S—$(CH_2)_q$-aryl substituted with 0–5 $R^{1c}$, and
  5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and substituted with 0–3 $R^{1c}$;

$R^{1b}$ is H,
  $C_1$–$C_4$ alkyl substituted with 0–3 $R^{1c}$,
  $C_2$–$C_4$ alkenyl substituted with 0–3 $R^{1c}$,
  $C_2$–$C_4$ alkynyl substituted with 0–3 $R^{1c}$,
  $C_3$–$C_6$ cycloalkyl substituted with 0–5 $R^{1c}$,
  $C_3$–$C_6$ carbocyle substituted with 0–5 $R^{1c}$,
  aryl substituted with 0–5 $R^{1c}$, or
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 $R^{1c}$;

$R^{1c}$ is selected at each occurrence from: $C_1$–$C_4$ alkyl, Cl, F, Br, I, OH, $C_1$–$C_4$ alkoxy, —CN, —$NO_2$, $C(O)OR^{1d}$, $NR^{1d}R^1$, $CF_3$, and $OCF_3$;

$R^{1d}$ is H or $C_1$–$C_4$ alkyl;

$R^2$ is H or $C_1$–$C_4$ alkyl;

$R^3$ is selected from the group: H,
  $C_1$–$C_6$ alkyl substituted with 0–4 $R^{3a}$,
  $C_2$–$C_6$ alkenyl substituted with 0–4 $R^{3a}$,
  $C_2$–$C_6$ alkynyl substituted with 0–4 $R^{3a}$,
  —$(CH_2)_q$—$C_3$–$C_6$ cycloalkyl substituted with 0–4 $R^{3b}$,
  —$(CH_2)_q$-aryl substituted with 0–5 $R^{3b}$, and
  —$(CH_2)_q$-5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and said heterocyclic group is substituted with 0–2 $R^{3b}$;

$R^{3a}$ is selected from the group: —$CO_2R^{11}$, —$NR^{11}R^{11}$, —$OR^{11}$, —$SR^{11}$, —C(=NH)$NH_2$, and aryl substituted with $R^{10b}$;

$R^{3b}$ is selected from the group: —$CO_2H$, —$NH_2$, —OH, —SH, and —C(=NH)$NH_2$;

$R^{3c}$ is, at each occurrence, independently selected from: H, $C_1$–$C_6$ alkyl, —OH, and $OR^{3d}$;

$R^{3d}$ is $C_1$–$C_6$ alkyl, $C_2$–$C_6$ alkenyl, $C_2$–$C_6$ alkynyl, —$(CH_2)_q$—$C_3$–$C_6$ cycloalkyl, —$(CH_2)_q$-aryl, or —$(CH_2)_q$-(5–10 membered heterocyclic group), wherein said heterocyclic group consists of carbon atoms and 1–4 heteroatoms selected from the group: O, S, and N;

$R^4$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^9$ is selected from —S(=O)$_2R^{9a}$ and —C(=O)$R^{9a}$;

$R^{9a}$ is selected from the group:
  phenyl substituted with 0–3 $R^{9c}$,
  naphthyl substituted with 0–3 $R^{9c}$, and
  5–14 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and said heterocyclic group is substituted with 0–3 $R^{9c}$;

$R^{9c}$ is selected at each occurrence from the group:
$CF_3$, $OCF_3$, Cl, F, Br, I, =O, OH, phenyl, $C(O)OR^{11}$, $NH_2$, $NH(CH_3)$, $N(CH_3)_2$, —CN, $NO_2$;
$C_1$–$C_4$ alkyl substituted with 0–3 $R^{9d}$,
$C_1$–$C_4$ alkoxy substituted with 0–3 $R^{9d}$,
$C_3$–$C_6$ cycloalkyl substituted with 0–3 $R^{9d}$,
aryl substituted with 0–5 $R^{9d}$, and
5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group is substituted with 0–4 $R^{9d}$;

$R^{9d}$ is selected at each occurrence from the group:
$C_1$–$C_4$ alkyl, $C_1$–$C_4$ alkoxy, $CF_3$, $OCF_3$, Cl, F, Br, I, =O, OH, phenyl, $C(O)OR^{11}$, $NH_2$, $NH(CH_3)$, $N(CH_3)_2$, —CN, and $NO_2$;

p is 1 or 2; and
q, at each occurence, is independently 0, 1 or 2.

[6] In a further even more preferred embodiment, the present invention provides novel compounds of Formula III, wherein:
X is —C(=O)—;
Y is —S(=O)$_2$—;
Z is selected from the group:
methyl, ethyl, propyl, trifluoromethyl, phenyl, benzyl, 4-phenyl-phenyl, 4-NCS-phenyl, 2-fluorophenyl-, 3-fluorophenyl-, 4-fluorophenyl-, 2-chlorophenyl-, 3-chlorophenyl-, 4-chlorophenyl-, 2-cyanophenyl-, 3-cyanophenyl-, 4-cyanophenyl-, 2-nitrophenyl-, 3-nitrophenyl-, 4-nitrophenyl-, 2-$CF_3SO_2$-phenyl-, 3-$CF_3SO_2$-phenyl-, 4-$CF_3SO_2$-phenyl-, 2-$CF_3$-phenyl-, 3-$CF_3$-phenyl-, 4-$CF_3$-phenyl-, 3-$NO_2$-4-Cl-phenyl-, 3-Cl-4-$CH_3$-phenyl-, 2-Cl-5-$CF_3$-phenyl-, 2-Cl-5-$CO_2$H-phenyl-, 3-$NO_2$-4-$CH_3$-phenyl-, 3-Cl-5-$NH_2SO_2$-phenyl-, 3,5-di$CF_3$-phenyl-, 3,4-di$CF_3$-phenyl-, 3,5-diCl-phenyl-, 2,5-diCl-phenyl-, 3,4-diCl-phenyl-, 3,5-diF-phenyl-, 2,5-diF-phenyl-, 3,4-diF-phenyl-, 2-F-4-Cl-5-$CO_2$H-phenyl-, 2,4-diCl-5-$CO_2$H-phenyl-, 2,4-diCl-5-$CH_3CO_2$-phenyl-, 2,4-diCl-5-$CH_3$-phenyl-, 2-OH-3,5-diCl-phenyl-, 2,4,5-triCl-phenyl-, 3,5-diCl-4-(4-$NO_2$phenyl)phenyl-, 2-Cl-5-benzylNHCO-phenyl-, 2-Cl-5-$CF_3CH_2$NHCO-phenyl-, 2-Cl-5-cyclopropylmethylNHCO-phenyl-, 2-Cl-4-$CH_3$CONH-phenyl-, 3-Cl-5-(phenylCONHSO$_2$)-phenyl-, 3-Cl-5-$CH_3$CONH-phenyl-, 5-ethoxy-benzothiazol-2-yl, naphth-2-yl, ($CH_3$CONH)thiadiazolyl-, (s-butylCONH) thiadiazolyl-, (n-pentylCONH)thiadiazolyl-, (phenylCONH)thiadiazolyl-, and (3-ClphenylCONH) thiadiazolyl-;
$A^2$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, Val;

$A^3$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;
$A^3$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;
$R^1$ is selected from the group:
—$CH_2CH_3$, —$CH_2CH_2CH_3$, —$CH(CH_3)_2$, —$CH_2CH_2CH_2CH_3$, —$CH_2CH(CH_3)_2$, —$CH_2C(CH_3)_3$, —$CH_2CH_2C(CH_3)_3$, —$CH_2CH_2CH_2C(CH_3)_3$, —$CH_2CH_2CH_2CH(CH_3)_2$, —$CH_2CH_2CH_2CH(CH_2CH_3)_2$, —$CH_2CH_2CH_2CH_2CH_3$, —$CH_2CH_2CH(CH_3)_2$, —$CH_2CH_2CH_2CH_2CH_3$, —$CH_2CF_3$, —$CH_2CH_2CF_3$, —$CH_2CH_2CH_2CF_3$, —$CH_2CHF_2$, —$CH_2CH_2CHF_2$, —$CH_2CH_2CH_2CHF_2$, —CH=$CH_2$, —$CH_2$CH=$CH_2$, —CH=CH$CH_3$, cis—$CH_2$CH=CH($CH_3$), trans—$CH_2$CH=CH($CH_3$), —$CH_2CH_2$CH=CH, —$CH_2$CH=C($CH_3$)$_2$, —$CH_2CH_2$CH=C($CH_3$)$_2$, —$CH_2CO_2$H, —$CH_2CH_2CO_2$H, —$CH_2CO_2C(CH_3)_3$, —$CH_2CH_2CO_2C(CH_3)_3$, —$CH_2CH_2CH_2CH_2NH_2$, phenyl, benzyl, phenethyl, phenpropyl, phenbutyl, (2-methylphenyl) ethyl-, (3-methylphenyl) ethyl-, (4-methylphenyl)ethyl-, (4-ethylphenyl)ethyl-, (4-i-propylphenyl)ethyl-, (4-t-butylphenyl)ethyl-, (4-hydroxyphenyl)ethyl-, (4-phenyl-phenyl)ethyl-, (4-phenoxy-phenyl) ethyl-, (4-cyclohexyl-phenyl) ethyl-, (4-cyclopropyl-phenyl)ethyl-, (2,5-dimethylphenyl)ethyl-, (2,4-dimethylphenyl)ethyl-, (2,6-difluorophenyl)ethyl-, (4-cyclopentyl-phenyl) ethyl-, (4-cyclobutyl-phenyl)ethyl-, (2-trifluoromethylphenyl)ethyl-, (3-trifluoromethylphenyl)ethyl-, (4-trifluoromethylphenyl)ethyl-, (2-fluorophenyl) ethyl-, (3-fluorophenyl)ethyl-, (4-fluorophenyl) ethyl-, (2-chlorophenyl) ethyl-, (3-chlorophenyl)ethyl-, (4-chlorophenyl)ethyl-, (2-bromophenyl) ethyl-, (3-bromophenyl) ethyl-, (4-bromophenyl)ethyl-, (2,3,4,5,6-pentafluorophenyl)ethyl-(naphth-2-yl)ethyl, (cyclobutyl)methyl, (cyclobutyl)ethyl, (cyclobutyl) propyl, cyclopropyl, cyclobutyl, cyclopentyl, and cyclohexyl;
$R^2$ is H, methyl or ethyl;
$R^{3c}$ is H, methyl, ethyl, —OH, methoxy, ethoxy, propoxy, phenoxy, or benzyloxy; and
$R^9$ is selected from:
2-pyrazinyl-carbonyl-, 4-(N-pyrrolyl)phenyl-carbonyl-, 5-(4-chlorophenyl)furan-2-yl-carbonyl-, 1-anthracenyl-carbonyl-, 7-nitro-anthracen-1-yl-carbonyl-, (3-phenyl-2-cyanomethoxyphenyl) carbonyl-, 5-(2-Cl-3—$CF_3$-phenyl)-furan-2-yl-carbonyl-, 5-(4-Cl-phenyl)-furan-2-yl-carbonyl-, 5-(pyrid-2-yl)-thiophen-2-yl-carbonyl-, (2-methoxyphenyl)ethylcarbonyl-, (3-benzopyrrolyl) ethylcarbonyl-, (N-phenyl-5-propyl-imidazol-4-yl)-carbonyl-, 1-naphthyl-sulphonyl-, and 5-(isoxazol-2-yl)thiophen-2-yl-sulphonyl-.

[7] In most preferred embodiment, the compound of Formula (I) is selected from the group:

N-(2-pyrazinylcarbonyl)-L-leucyl-L-isoleucyl-3-cyclohexyl-L-alanyl-2-oxo-(3 S)-3-amino pentanoylglycine;

(3S)-2-oxo-3-{[N-(2-pyrazinylcarbonyl)-L-leucyl-L-isoleucyl-3-cyclohexyl-L-alanyl]amino}-N-(2H-tetrazol-5-ylmethyl) pentanamide;

2-oxo-3-[[N-(2-pyrazinylcarbonyl)-L-leucyl-L-isoleucyl-3-cyclohexylalanyl]amino]-N-(sulfomethyl)pentanamide;

N-(2-pyrazinylcarbonyl)-L-leucyl-L-isoleucyl-3-cyclohexylalanyl-2-oxo-3-aminopentanoyl-N-[(2-nitrophenyl) sulfonyl]glycinamide;

N-(2-pyrazinylcarbonyl)-L-leucyl-L-isoleucyl-3-cyclohexylalanyl-2-oxo-3-aminopentanoyl-N-(methylsulfonyl) glycinamide;

N-(2-pyrazinylcarbonyl)-L-leucyl-L-isoleucyl-3-cyclohexylalanyl-2-oxo-3-aminopentanoyl-N-[(phenylmethyl) sulfonyl]glycinamide;

N-(2-pyrazinylcarbonyl)-L-leucyl-L-isoleucyl-3-cyclohexylalanyl-2-oxo-3-aminopentanoyl-N-(phenylsulfonyl) glycinamide;

N-(2-pyrazinylcarbonyl)-L-leucyl-L-isoleucyl-3-cyclohexylalanyl-2-oxo-3-aminopentanoyl-N-[(trifluoromethyl)sulfonyl]glycinamide;

N-(2-pyrazinylcarbonyl)-L-leucyl-L-isoleucyl-3-cyclohexylalanyl-2-oxo-3-aminopentanoyl-N-[(2-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[(4-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[(4-fluorophenyl)sulfonyl]glycinamide;

N-(2-pyrazinylcarbonyl)-L-leucyl-L-isoleucyl-3-cyclohexyl-L-alanyl-2-oxo-(3 S)-3-amino pentanoyl-N-[(3-fluorophenyl)sulfonyl]glycinamide;

N-(2-pyrazinylcarbonyl)-L-leucyl-L-isoleucyl-3-cyclohexylalanyl-2-oxo-3-aminopentanoyl-N-[(2-fluorophenyl) sulfonyl]glycinamide;

N-(2-pyrazinylcarbonyl)-L-leucyl-L-isoleucyl-3-cyclohexylalanyl-2-oxo-3-aminopentanoyl-N-[(4-chlorophenyl) sulfonyl]glycinamide;

N-(2-pyrazinylcarbonyl)-L-leucyl-L-isoleucyl-3-cyclohexylalanyl-2-oxo-3-aminopentano yl-N-[(3-chlorophenyl) sulfonyl]glycinamide;

N-(2-pyrazinylcarbonyl)-L-leucyl-L-isoleucyl-3-cyclohexylalanyl-2-oxo-3-aminopentanoyl-N-[[4-(thionitroso) phenyl]sulfonyl]glycinamide;

N-(2-pyrazinylcarbonyl)-L-leucyl-L-isoleucyl-3-cyclohexylalanyl-2-oxo-3-aminopentanoyl-N-[[4-[(trifluoromethyl)sulfonyl]phenyl]sulfonyl]glycinamide;

N-(2-pyrazinylcarbonyl)-L-leucyl-L-isoleucyl-3-cyclohexylalanyl-2-oxo-3-aminopentanoyl-N-[[4-(trifluoromethyl)phenyl]sulfonyl]glycinamide;

N-(2-pyrazinylcarbonyl)-L-leucyl-L-isoleucyl-3-cyclohexylalanyl-2-oxo-3-aminopentanoyl-N-[(4-cyanophenyl)sulfonyl]glycinamide;

N-(2-pyrazinylcarbonyl)-L-leucyl-L-isoleucyl-3-cyclohexylalanyl-2-oxo-3-aminopentanoyl-N-[(3-chloro-4-methylphenyl)sulfonyl]glycinamide;

N-(2-pyrazinylcarbonyl)-L-leucyl-L-isoleucyl-3-cyclohexylalanyl-2-oxo-3-aminopentanoyl-N-[(4-chloro-3-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[(3,5-dichlorophenyl)sulfonyl]glycinamide;

N-(2-pyrazinylcarbonyl)-L-leucyl-L-isoleucyl-3-cyclohexylalanyl-2-oxo-3-aminopentanoyl-N-[(4-methyl-3-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[[2-chloro-5-(trifluoromethyl)phenyl]sulfonyl]glycinamide;

N-(2-pyrazinylcarbonyl)-L-leucyl-L-isoleucyl-3-cyclohexylalanyl-2-oxo-3-aminopentanoyl-N-[(5-carboxy-2-chlorophenyl)sulfonyl]glycinamide;

N-(2-pyrazinylcarbonyl)-L-leucyl-L-isoleucyl-3-cyclohexylalanyl-2-oxo-3-aminopentanoyl-N-[(2,5-dichlorophenyl)sulfonyl]glycinamide;

N-(2-pyrazinylcarbonyl)-L-leucyl-L-isoleucyl-3-cyclohexylalanyl-2-oxo-3-aminopentanoyl-N-[(3,4-difluorophenyl)sulfonyl]glycinamide;

N-(2-pyrazinylcarbonyl)-L-leucyl-L-isoleucyl-3-cyclohexylalanyl-2-oxo-3-aminopentanoyl-N-[(3,5-dichloro-2-hydroxyphenyl)sulfonyl]glycinamide;

N-(2-pyrazinylcarbonyl)-L-leucyl-L-isoleucyl-3-cyclohexyl-L-alanyl-2-oxo-(3S)-3-amino pentanoyl-N-[(2,4,,5-trichlorophenyl)-sulfonyl]glycinamide;

N-(2-pyrazinylcarbonyl)-L-leucyl-L-isoleucyl-3-cyclohexylalanyl-2-oxo-3-aminopentanoyl-N-[(5-carboxy-4-chloro-2-fluorophenyl)sulfonyl]glycinamide;

N-(2-pyrazinylcarbonyl)-L-leucyl-L-isoleucyl-3-cyclohexylalanyl-2-oxo-3-aminopentanoyl-N-[[5-(dimethylamino)-1-naphthalenyl]sulfonyl]glycinamide;

N-(2-pyrazinylcarbonyl)-L-leucyl-L-isoleucyl-3-cyclohexylalanyl-2-oxo-3-aminopentanoyl-N-(2-naphthalenylsulfonyl)glycinamide;

N-(2-pyrazinylcarbonyl)-L-leucyl-L-isoleucyl-3-cyclohexyl-L-alanyl-2-oxo-(3S)-3-aminopentanoyl-N-[(4-(phenyl)phenyl)-sulfonyl]glycinamide;

N-(2-pyrazinylcarbonyl)-L-leucyl-L-isoleucyl-3-cyclohexylalanyl-2-oxo-3-aminopentanoyl-N-[(6-ethoxy-2-benzothiazolyl)sulfonyl]glycinamide;

N-(2-pyrazinylcarbonyl)-L-leucyl-L-isoleucyl-3-cyclohexylalanyl-2-oxo-3-aminopentanoyl-N-[[2-chloro-5-[[(phenylmethyl)amino]carbonyl]phenyl]sulfonyl] glycinamide;

N-(2-pyrazinylcarbonyl)-L-leucyl-L-isoleucyl-3-cyclohexyl-L-alanyl-2-oxo-(3S)-3-aminopentanoyl-N-[[2-chloro-5-[[(2-trifluoroethyl)amino]carbonyl]phenyl] sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[2-chloro-5-[[(cyclopropylmethyl)amino]carbonyl] phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-nitro-4-(2-pyrimidinylthio)phenyl]sulfonyl] glycinamide;

N-(2-pyrazinylcarbonyl)-L-leucyl-L-isoleucyl-3-cyclohexyl-L-alanyl-2-oxo-(3S)-3-aminopentanoyl-N-[[2-chloro-4-(acetylamino)phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-chloro-4-(2-benzoxazolylthio)phenyl]sulfonyl] glycinamide;

N-(2-pyrazinylcarbonyl)-L-leucyl-L-isoleucyl-3-cyclohexyl-L-alanyl-2-oxo-(3 S)-3-amino pentanoyl-N-[[3,5-dichloro-4-(4-nitrophenoxy)phenyl]sulfonyl] glycinamide;

N-(2-pyrazinylcarbonyl)-L-leucyl-L-isoleucyl-3-cyclohexyl-L-alanyl-2-oxo-(3 S)-3-amino pentanoyl-N-[[5-(acetylamino)-1,3,4-thiadiazol-2-yl]sulfonyl] glycinamide;

N-(2-pyrazinylcarbonyl)-L-leucyl-L-isoleucyl-3-cyclohexyl-L-alanyl-2-oxo-(3 S)-3-amino pentanoyl-N-[(3-cyanophenyl)sulfonyl]glycinamide;

N-(2-pyrazinylcarbonyl)-L-leucyl-L-isoleucyl-3-cyclohexyl-L-alanyl-2-oxo-(3 S)-3-amino pentanoyl-N-[[3-(aminosulfonyl)-5-chlorophenyl]sulfonyl]glycinamide;

N-(2-pyrazinylcarbonyl)-L-leucyl-L-isoleucyl-3-cyclohexyl-L-alanyl-2-oxo-(3S)-3-amino pentanoyl-N-[[3,5-bis(trifluoromethyl)phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[4-[5-[3-(4-chlorophenyl)-3-oxo-1-propenyl]-2-furanyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-[[(phenylmethyl)amino]carbonyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-[[(2,2,2-trifluoroethyl)amino]carbonyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-[(benzoylamino)sulfonyl]-5-chlorophenyl]sulfonyl]glycinamide;

N-(2-pyrazinylcarbonyl)-L-leucyl-L-isoleucyl-3-cyclohexyl-L-alanyl-5,5-difluoro-2-oxo-(3S)-3-aminopentanoylglycine;

(3S)-5,5-difluoro-2-oxo-3-[[N-(2-pyrazinylcarbonyl)-L-leucyl-L-isoleucyl-3-cyclohexyl-L-alanyl]amino]-N-(2H-tetrazol-5-ylmethyl)pentanamide;

N-(2-pyrazinylcarbonyl)-L-leucyl-L-isoleucyl-3-cyclohexyl-L-alanyl-5,5-difluoro-2-oxo-(3S)-3-aminopentanoyl-N-[(3,5-dichlorophenyl)sulfonyl]glycinamide;

N-(2-pyrazinylcarbonyl)-L-leucyl-L-isoleucyl-3-cyclohexyl-L-alanyl-5,5-difluoro-2-oxo-(3S)-3-aminopentanoyl-N-[(3-chlorophenyl)sulfonyl]glycinamide;

N-(2-pyrazinylcarbonyl)-L-leucyl-L-isoleucyl-3-cyclohexyl-L-alanyl-5,5-difluoro-2-oxo-(3S)-3-aminopentanoyl-N-[5-(acetylamino)-1,3,4-thiadiazol-2-yl]sulfonyl]-glycinamide;

N-(2-pyrazinylcarbonyl)-L-leucyl-L-isoleucyl-3-cyclohexyl-L-alanyl-5,5-difluoro-2-oxo-(3S)-3-aminopentanoyl-N-(3-aminosulfonyl-5-chlorophenyl)sulfonyl]glycinamide;

(3S)-5,5,5-trifluoro-2-oxo-3-[[N-(2-pyrazinylcarbonyl)-L-leucyl-L-isoleucyl-3-cyclohexyl-L-alanyl]amino]-N-(2H-tetrazol-5-ylmethyl)pentanamide;

N-[4-sec-butyl-15-{[(3-chloro-5-{[(3,3,3-trifluoropropanoyl)amino]sulfonyl}phenyl)sulfonyl]amino}-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-15-[({3-chloro-5-[(hexanoylamino)sulfonyl]phenyl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[15-[([1,1'-biphenyl]-3-ylsulfonyl)amino]-4-sec-butyl-7-(cyclohexylmethyl)-10-ethyl-1-isobutyl-2,5,8,11,12,15-hexaoxo-3,6,9,13-tetraazapentadec-1-yl]-2-pyrazinecarboxamide;

N-(4-sec-butyl-7-(cyclohexylmethyl)-10-ethyl-1-isobutyl-15-{[(4'-methoxy[1,1'-biphenyl]-4-yl)sulfonyl]amino}-2,5,8,11,12,15-hexaoxo-3,6,9,13-tetraazapentadec-1-yl)-2-pyrazinecarboxamide;

N-(4-sec-butyl-7-(cyclohexylmethyl)-15-{[(3',5'-dichloro[1,1'-biphenyl]-4-yl)sulfonyl]amino}-10-ethyl-1-isobutyl-2,5,8,11,12,15-hexaoxo-3,6,9,13-tetraazapentadec-1-yl)-2-pyrazinecarboxamide;

N-[4-sec-butyl-15-{[(4'-chloro[1,1'-biphenyl]-3-yl)sulfonyl]amino}-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-7-(cyclohexylmethyl)-10-(2,2-difluoroethyl)-1-isobutyl-15-({[3-(2-methylphenoxy)phenyl]sulfonyl}amino)-2,5,8,11,12,15-hexaoxo-3,6,9,13-tetraazapentadec-1-yl]-2-pyrazinecarboxamide;

N-[4-sec-butyl-15-({[3-(2-chlorophenoxy)phenyl]sulfonyl}amino)-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

(3S,6S,9S,12S)-9-(cyclohexylmethyl)-12-(2,2-difluoroethyl)-3-isobutyl-6-[(1R)-1-methylpropyl]-1,4,7,10,13-pentaoxo-1-(2-pyrazinyl)-2,5,8,11-tetraazatetradecan-14-oic acid;

N-(4-sec-butyl-7-(cyclohexylmethyl)-10-(2,2-difluoroethyl)-1-isobutyl-15-{[(4'-methyl[1,1'-biphenyl]-3-yl)sulfonyl]amino}-2,5,8,11,12,15-hexaoxo-3,6,9,13-tetraazapentadec-1-yl)-2-pyrazinecarboxamide;

N-[15-({[3',5'-bis(trifluoromethyl)[1,1'-biphenyl]-3-yl]sulfonyl}amino)-4-sec-butyl-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-15-[({5-[(4-cyanobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-15-[({5-[(2-chlorobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-{4-sec-butyl-7-(cyclohexylmethyl)-10-(2,2-difluoroethyl)-1-isobutyl-15-[({5-[(4-methoxybenzoyl)amino]-1,3,4-thiadiazol-2-yl}sulfonyl)amino]-2,5,8,11,12,15-hexaoxo-3,6,9,13-tetraazapentadec-1-yl}-2-pyrazinecarboxamide;

N-{4-sec-butyl-7-(cyclohexylmethyl)-10-(2,2-difluoroethyl)-1-isobutyl-15-[({5-[(3-methoxybenzoyl)amino]-1,3,4-thiadiazol-2-yl}sulfonyl)amino]-2,5,8,11,12,15-hexaoxo-3,6,9,13-tetraazapentadec-1-yl}-2-pyrazinecarboxamide;

N-{4-sec-butyl-7-(cyclohexylmethyl)-10-(2,2-difluoroethyl)-15-[({5-[(3,5-dimethylbenzoyl)amino]-1,3,4-thiadiazol-2-yl}sulfonyl)amino]-1-isobutyl-2,5,8,11,12,15-hexaoxo-3,6,9,13-tetraazapentadec-1-yl}-2-pyrazinecarboxamide;

N-(4-sec-butyl-7-(cyclohexylmethyl)-10-(2,2-difluoroethyl)-1-isobutyl-2,5,8,11,12,15-hexaoxo-15-{[(3-phenoxyphenyl)sulfonyl]amino}-3,6,9,13-tetraazapentadec-1-yl)-2-pyrazinecarboxamide;

6-sec-butyl-9-(cyclohexylmethyl)-12-ethyl-3-isobutyl-1,4,7,10,13-pentaoxo-1-(2-pyrazinyl)-2,5,8,11-tetraazatetradecan-14-oic acid;

N-{4-sec-butyl-7-(cyclohexylmethyl)-10-(2,2-difluoroethyl)-1-isobutyl-15-[({5-[(3-methylbutanoyl)amino]-1,3,4-thiadiazol-2-yl}sulfonyl)amino]-2,5,8,11,12,15-hexaoxo-3,6,9,13-tetraazapentadec-1-yl}-2-pyrazinecarboxamide;

N-[4-sec-butyl-7-(cyclohexylmethyl)-10-(2,2-difluoroethyl)-15-({[5-(hexanoylamino)-1,3,4-thiadiazol- 2-yl]sulfonyl}amino)-1-isobutyl-2,5,8,11,12,15-hexaoxo-3,6,9,13-tetraazapentadec-1-yl]-2-pyrazinecarboxamide;

methyl (3S,6S,9S,12S)-9-(cyclohexylmethyl)-12-(2,2-difluoroethyl)-3-isobutyl-6-[(1R)-1-methylpropyl]-1,4,7,10,13,14-hexaoxo-1-(2-pyrazinyl)-2,5,8,11,15-pentaazaheptadecan-17-oate;

N-[4-sec-butyl-15-{[(3-chloro-5-{[(3-chlorobenzoyl)amino]sulfonyl}phenyl)sulfonyl]amino}-7-(cyclohexylmethyl)-10-ethyl-1-isobutyl-2,5,8,11,12,15-hexaoxo-3,6,9,13-tetraazapentadec-1-yl]-2-pyrazinecarboxamide;

N-[4-sec-butyl-7-(cyclohexylmethyl)-10-(2,2-difluoroethyl)-1-isobutyl-2,5,8,11,12,15-hexaoxo-15-({[4'-(trifluoromethyl)[1,1'-biphenyl]-3-yl]sulfonyl}amino)-3,6,9,13-tetraazapentadec-1-yl]-2-pyrazinecarboxamide;

N-[15-[([1,1'-biphenyl]-3-ylsulfonyl)amino]-4-sec-butyl-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-15-[({5-[(4-tert-butylbenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-15-{[(3-chloro-5-{[(3-methylbutanoyl)amino]sulfonyl}phenyl)sulfonyl]amino}-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-{(1S,4S,7S,10S)-7-(cyclohexylmethyl)-10-(2,2-difluoroethyl)-1-isobutyl-14-[4-(4-methoxyphenyl)-5-(trifluoromethyl)-4H-1,2,4-triazol-3-yl]-4-[(1R)-1-methylpropyl]-2,5,8,11,12-pentaoxo-3,6,9,13-tetraazatetradec-1-yl}-2-pyrazinecarboxamide;

N-{4-sec-butyl-7-(cyclohexylmethyl)-10-(2,2-difluoroethyl)-15-[({5-[(4-ethylbenzoyl)amino]-1,3,4-thiadiazol-2-yl}sulfonyl)amino]-1-isobutyl-2,5,8,11,12,15-hexaoxo-3,6,9,13-tetraazapentadec-1-yl}-2-pyrazinecarboxamide;

N-[4-sec-butyl-15-[({5-[(4-chlorobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-7-(cyclohexylmethyl)-15-[({5-[(3,5-difluorobenzoyl)amino]-1,3,4-thiadiazol-2-yl}sulfonyl)amino]-10-(2,2-difluoroethyl)-1-isobutyl-2,5,8,11,12,15-hexaoxo-3,6,9,13-tetraazapentadec-1-yl]-2-pyrazinecarboxamide;

N-[4-sec-butyl-15-[({5-[(3-chlorobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide;

N-{(1S,4S,7S,10S)-7-(cyclohexylmethyl)-10-ethyl-1-isobutyl-4-[(1R)-1-methylpropyl]-2,5,8,11,12-pentaoxo-3,6,9,13-tetraazahexadec-15-en-1-yl}-2-pyrazinecarboxamide;

N-{(1S,4S,7S,10S)-7-(cyclohexylmethyl)-10-ethyl-1-isobutyl-4-[(1R)-1-methylpropyl]-2,5,8,11,12-pentaoxo-3,6,9,13-tetraazahexadec-15-yn-1-yl}-2-pyrazinecarboxamide;

tert-butyl (3S,6S,9S,12S)-9-(cyclohexylmethyl)-12-ethyl-3-isobutyl-6-[(1R)-1-methylpropyl]-1,4,7,10,13,14-hexaoxo-1-(2-pyrazinyl)-2,5,8,11,15-pentaazaheptadecan-17-oate;

N-{(1S,4S,7S,10S)-7-(cyclohexylmethyl)-10-ethyl-1-isobutyl-4-[(1R)-1-methylpropyl]-2,5,8,11,12-pentaoxo-14-phenyl-3,6,9,13-tetraazatetradec-1-yl}-2-pyrazinecarboxamide N-((1S)-1-{[(((1S,2R)-1-{[(((1S)-1-(cyclohexylmethyl)-2-{[(1S)-1-ethyl-2,3-dioxo-3-(1-pyrrolidinyl)propyl]amino}-2-oxoethyl) amino]carbonyl}-2-methylbutyl)amino]carbonyl}-3-methylbutyl)-2-pyrazinecarboxamide;

N-{(1S,4S,7S,10S)-7-(cyclohexylmethyl)-10-ethyl-15,15,15-trifluoro-1-isobutyl-4-[(1R)-1-methylpropyl]-2,5,8,11,12-pentaoxo-3,6,9,13-tetraazapentadec-1-yl}-2-pyrazinecarboxamide;

N-{(1S,4S,7S,10S)-15-amino-7-(cyclohexylmethyl)-10-ethyl-1-isobutyl-4-[(1R)-1-methylpropyl]-2,5,8,11,12,15-hexaoxo-3,6,9,13-tetraazapentadec-1-yl}-2-pyrazinecarboxamide;

(3S, 6S,9S, 12S, 16S)-9-(cyclohexylmethyl)-12-ethyl-3-isobutyl-16-methyl-6-[(1R)-1-methylpropyl]-1,4,7,10,13,14-hexaoxo-1-(2-pyrazinyl)-2,5,8,11,15-pentaazaheptadecan-17-oic acid;

N-[9-sec-butyl-6-(cyclohexylmethyl)-3-ethyl-12-isobutyl-2,5,8,11,14-pentaoxo-14-(2-pyrazinyl)-4,7,10,13-tetraazatetradec-1-anoyl]aspartic acid; (3S,6S,9S,12S)-9-(cyclohexylmethyl)-12-ethyl-3-isobutyl-6-[(1R)-1-methylpropyl]-1,4,7,10,13,14-hexaoxo-1-(2-pyrazinyl)-2,5,8,11,15-pentaazaoctadecan-18-oic acid;

1,1-dimethylethyl N-(2-pyrazinylcarbonyl)-L-leucyl-L-isoleucyl-(4R)-4-(phenylmethoxy)-L-prolyl-5,5-difluoro-2-oxo-(3S)-3-aminopentanoylglycine;

N-(2-pyrazinylcarbonyl)-L-leucyl-L-isoleucyl-(4R)-4-(phenylmethoxy)-L-prolyl-5,5-di fluoro-2-oxo-(3S)-3-aminopentanoylglycine;

(4R)-1-[N-(2-pyrazinylcarbonyl)-L-leucyl-L-isoleucyl]-N-[(1S)-1-(2,2-difluoroethyl)-2,3-dioxo-3-[(2H)-tetrazol-5-yl methyl)amino]propyl]-4-(phenylmethoxy)-L-prolinamide;

(4R)-N-(2-pyrazinylcarbonyl)-L-leucyl-L-isoleucyl-N-[(1S)-1-(2,2-difluoroethyl)-3-methoxy-2,3-dioxopropyl]-4-(phenylmethoxy)-L-prolinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(3-chlorophenyl)sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(5-carboxy-2-chlorophenyl)sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(5-acetylamino)1,3,4-thiadiazol-2-yl)sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[3,5-dichorophenyl)sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-(4-methyl-3-nitrophenyl)sulfonyl]-glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-(3-carboxyl-4-chloro-2-fluorophenyl)sulfonyl]-glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-[(3-chloro-4-acetylamino)phenyl]sulfonyl]-glycinamide;

N-((1S)-1-{[((1S,2R)-1-{[(2S,4R)-2-({[(1S)-3-({2-[({3-[(benzoylamino)sulfonyl]-5-chlorophenyl}sulfonyl)amino]-2-oxoethyl}amino)-1-(2,2-difluoroethyl)-2,3-dioxopropyl]amino}carbonyl)-4-(benzyloxy)pyrrolidinyl]carbonyl}-2-methylbutyl)amino]carbonyl}-3-methylbutyl)-2-pyrazinecarboxamide;

tert-butyl ({(3S)-3-[({(2S,4R)-4-(benzyloxy)-1-[(2S)-3-methyl-2-({(2S)-3-methyl-2-[(2-pyrazinylcarbonyl)amino]butanoyl}amino)butanoyl]pyrrolidinyl}carbonyl)amino]-5,5-difluoro-2-oxopentanoyl}amino)acetate;

N-((1S)-1-{[((1S,2R)-1-{[(2S,4R)-4-(benzyloxy)-2-({[(1S)-3-[(2-{[(3-chloro-4-methylphenyl)sulfonyl]amino}-2-oxoethyl)amino]-1-(2,2-difluoroethyl)-2,3-dioxopropyl]amino}carbonyl)pyrrolidinyl]carbonyl}-2-methylbutyl)amino]carbonyl}-3-methylbutyl)-2-pyrazinecarboxamide;

N-((1S)-1-{[((1S,2R)-1-{[(2S,4R)-4-(benzyloxy)-2-({[(1S)-3-({2-[({5-[(3-chlorobenzoyl)amino]-1,3,4-thiadiazol-2-yl}sulfonyl)amino]-2-oxoethyl}amino)-1-(2,2-difluoroethyl)-2,3-dioxopropyl]amino}carbonyl)pyrrolidinyl]carbonyl}-2-methylbutyl)amino]carbonyl}-3-methylbutyl)-2-pyrazinecarboxamide;

methyl ({(3S)-3-[({(2S,4R)-4-(benzyloxy)-1-[(2S,3R)-3-methyl-2-({(2S)-4-methyl-2-[(2-pyrazinylcarbonyl)amino]pentanoyl}amino)pentanoyl]pyrrolidinyl}carbonyl)amino]-5,5-difluoro-2-oxopentanoyl}amino)acetate;

N-((1S)-1-{[((1S,2R)-1-([(2S, 4R)-4-(benzyloxy)-2-({[(1S)-3-[(2-{[(2,4-dichloro-5-methylphenyl)sulfonyl]amino}-2-oxoethyl)amino]-1-(2,2-difluoroethyl)-2,3-dioxopropyl]amino}carbonyl)pyrrolidinyl]carbonyl)-2-methylbutyl)amino]carbonyl}-3-methylbutyl)-2-pyrazinecarboxamide;

N-[(1S)-1-({[(1S,2R)-1-({(2S,4R)-4-(benzyloxy)-2-[({(1S)-1-(2,2-difluoroethyl)-3-[(2-{[(3,4-difluorophenyl)sulfonyl]amino}-2-oxoethyl)amino]-2,3-dioxopropyl}amino)carbonyl]pyrrolidinyl}carbonyl)-2-methylbutyl]amino}carbonyl)-3-methylbutyl]-2-pyrazinecarboxamide; methyl 5-([{[({(3S)-3-[({(2S,4R)-4-(benzyloxy)-1-[(2S,3R)-3-methyl-2-({(2S)-4-methyl-2-[(2-pyrazinylcarbonyl)amino]pentanoyl}amino)pentanoyl]pyrrolidinyl}carbonyl)amino]-5,5-difluoro-2-oxopentanoyl}amino)acetyl]amino}sulfonyl)-2,4-dichlorobenzoate;

N-{(1S)-1-[({{(1S,2R)-1-[((2S,4R)-4-(benzyloxy)-2-{[((1S)-1-(2,2-difluoroethyl)-3-{[2-({[4-(3,5-dimethyl-1-piperidinyl)-3-nitrophenyl]sulfonyl}amino)-2-oxoethyl]amino}-2,3-dioxopropyl)amino]carbonyl]pyrrolidinyl)carbonyl]-2-methylbutyl}amino)carbonyl]-3-methylbutyl}-2-pyrazinecarboxamide;

N-[(1S)-1-({[(1S,2R)-1-({(2S,4R)-4-(benzyloxy)-2-[({(1S)-1-(2,2-difluoroethyl)-3-[(2-([(3-nitrophenyl)sulfonyl]amino}-2-oxoethyl)amino]-2,3-dioxopropyl}amino)carbonyl]pyrrolidinyl}carbonyl)-2-methylbutyl]amino}carbonyl)-3-methylbutyl]-2-pyrazinecarboxamide;

N-{(1S)-1-[({(1S, 2R)-1-[((2S, 4R)-4-(benzyloxy)-2-{[((1S)-1-(2,2-difluoroethyl)-3-{[2-({[5-(hexanoylamino)-1,3,4-thiadiazol-2-yl]sulfonyl}amino)-2-oxoethyl]amino}-2,3-dioxopropyl)amino]carbonyl}pyrrolidinyl)carbonyl]-2-methylbutyl}amino)carbonyl]-3-methylbutyl}-2-pyrazinecarboxamide;

5-({[({(3S)-3-[({(2S,4R)-4-(benzyloxy)-1-[(2S,3R)-3-methyl-2-({(2S)-4-methyl-2-[(2-pyrazinylcarbonyl)amino]pentanoyl}amino)pentanoyl]pyrrolidinyl}carbonyl)amino]-5,5-difluoro-2-oxopentanoyl}amino)acetyl]amino}sulfonyl)-2,4-dichlorobenzoic acid;

N-[[5-(4-chlorophenyl)-2-furanyl]carbonyl]-L-isoleucyl-3-cyclohexylalanyl-2-oxo-3-aminopentanoylglycine;

N-[[5-(4-chlorophenyl)-2-furanyl]carbonyl]-Lisoleucyl-3-cyclohexylalanyl-2-oxo-3-aminopentanoyl-N-[(trifluoromethyl)sulfonyl]glycinamide;

N-[[5-(4-chlorophenyl)-2-furanyl]carbonyl]-Lisoleucyl-3-cyclohexylalanyl-2-oxo-3-aminopentanoyl-N-[(3,5-dichlorophenyl)sulfonyl]glycinamide;

N-[[5-(4-chlorophenyl)-2-furanyl]carbonyl]-Lisoleucyl-3-cyclohexylalanyl-2-oxo-3-aminopentanoyl-N-[(3-nitrophenyl)sulfonyl]glycinamide;

(4R)-1-[[5-(4-chlorophenyl)-2-furanyl]carbonyl-L-isoleucyl-N-[(1S)-1-(2,2-difluoroethyl)-2,3-dioxo-3-[(2H-tetrazol-5-ylmethyl)amino]propyl]-4-(phenylmethoxy)-L-prolinamide;

(2S,4R)-4-(benzyloxy)-N-{(1S)-1-(2,2-difluoroethyl)-2,3-dioxo-3-[(2H-tetraazol-5-ylmethyl)amino]propyl}-1-((2S,3R)-3-methyl-2-{[(9-oxo-9H-fluoren-1-yl)carbonyl]amino}pentanoyl)-2-pyrrolidinecarboxamide;

tert-butyl {[(3S)-3-({[(2S,4R)-4-(benzyloxy)-1-((2S,3R)-3-methyl-2-{[(9-oxo-9H-fluoren-1-yl)carbonyl]amino}pentanoyl)pyrrolidinyl]carbonyl}amino)-5,5-difluoro-2-oxopentanoyl]amino}acetate;

{[(3S)-3-({[(2S,4R)-4-(benzyloxy)-1-((2S,3R)-3-methyl-2-{[(9-oxo-9H-fluoren-1-yl)carbonyl]amino}pentanoyl)pyrrolidinyl]carbonyl}amino)-5,5-difluoro-2-oxopentanoyl]amino}acetic acid;

(2S,4R)-N-[(1S)-3-{[2-({[5-(acetylamino)-1,3,4-thiadiazol-2-yl]sulfonyl}amino)-2-oxoethyl]amino}-1-(2,2-difluoroethyl)-2,3-dioxopropyl]-4-(benzyloxy)-1-((2S,3R)-3-methyl-2-{[(9-oxo-9H-fluoren-1-yl)carbonyl]amino}pentanoyl)-2-pyrrolidinecarboxamide;

(2S,4R)-4-(benzyloxy)-N-((1S)-1-(2,2-difluoroethyl)-3-{[2-({[5-(hexanoylamino)-1,3,4-thiadiazol-2-yl]sulfonyl}amino)-2-oxoethyl]amino}-2,3-dioxopropyl)-1-((2S,3R)-3-methyl-2-{[(9-oxo-9H-fluoren-1-yl)carbonyl]amino}pentanoyl)-2-pyrrolidinecarboxamide;

((2S,4R)-4-(benzyloxy)-N-[(1S)-3-({2-[({5-[(4-chlorobenzoyl)amino]-1,3,4-thiadiazol-2-ylsulfonyl)amino]-2-oxoethyl}amino)-1-(2,2-difluoroethyl)-2,3-dioxopropyl]-1-((2S,3R)-3-methyl-2-{[(9-oxo-9H-fluoren-1-yl)carbonyl]amino}pentanoyl)-2-pyrrolidinecarboxamide;

(2S,4R)-4-(benzyloxy)-N-[(1S)-1-(2,2-difluoroethyl)-3-({2-[({5-[(4-ethylbenzoyl)amino]-1,3,4-thiadiazol-2-yl}sulfonyl)amino]-2-oxoethyl}amino)-2,3-dioxopropyl]-1-((2S,3R)-3-methyl-2-{[(9-oxo-9H-fluoren-1-yl)carbonyl]amino}pentanoyl)-2-pyrrolidinecarboxamide;

tert-butyl {[(3S)-3-({[(2S,4R)-4-(benzyloxy)-1-((2S,3R)-2-{[5-(4-chlorophenyl)-2-furoyl]amino}-3-methylpentanoyl)pyrrolidinyl]carbonyl}amino)-5,5-difluoro-2-oxopentanoyl]amino}acetate;

{[(3S)-3-({[(2S,4R)-4-(benzyloxy)-1-((2S,3R)-2-{[5-(4-chlorophenyl)-2-furoyl]amino}-3-methylpentanoyl)pyrrolidinyl]carbonyl}amino)-5,5-difluoro-2-oxopentanoyl]amino}acetic acid;

(2S,4R)-N-[(1S)-3-{[2-({[5-(acetylamino)-1,3,4-thiadiazol-2-yl]sulfonyl}amino)-2-oxoethyl]amino)-1-(2,2-difluoroethyl)-2,3-dioxopropyl]-4-(benzyloxy)-1-((2S,3R)-2-{[5-(4-chlorophenyl)-2-furoyl]amino}-3-methylpentanoyl)-2-pyrrolidinecarboxamide;

(2S,4R)-4-(benzyloxy)-N-[(1S)-3-({2-[({5-[(3-chlorobenzoyl)amino]-1,3,4-thiadiazol-2-yl}sulfonyl)amino]-2-oxoethyl}amino)-1-(2,2-difluoroethyl)-2,3-dioxopropyl]-1-((2S,3R)-2-{[5-(4-chlorophenyl)-2-furoyl]amino}-3-methylpentanoyl)-2-pyrrolidinecarboxamide;

(2S,4R)-4-(benzyloxy)-N-[(1S)-3-({2-[([1,1'-biphenyl]-3-ylsulfonyl)amino]-2-oxoethyl}amino)-1-(2,2-difluoroethyl)-2,3-dioxopropyl]-1-((2S,3R)-2-{[5-(4-chlorophenyl)-2-furoyl]amino}-3-methylpentanoyl)-2-pyrrolidinecarboxamide;

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}-2-pyrazinecarboxamide;

(6S, 9S, 12S)-N,3-diallyl-6-(cyclohexylmethyl)-12-isobutyl-9-[(1R)-1-methylpropyl]-2,5,8,11,14-pentaoxo-16,16-diphenyl-4,7,10,13-tetraazahexadecan-1-amide;

(4S,7S,10S)-N,13-diallyl-10-(cyclohexylmethyl)-4-isobutyl-7-[(1R)-1-methylpropyl]-2,5,8,11,14-pentaoxo-3,6,9,12-tetraazapentadecan-15-amide;

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}-2-pyridinecarboxamide;

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}nicotinamide;

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}-4-nitro-1H-pyrazole-3-carboxamide;

2-{(3S,6S,9S)-12-allyl-9-(cyclohexylmethyl)-3-isobutyl-6-[(1R)-1-methylpropyl]-4,7,10,13,14-pentaoxo-2,5,8,11,15-pentaazaoctadec-17-en-1-anoyl}benzoic acid;

N-[4-sec-butyl-7-(cyclohexylmethyl)-10-ethyl-1-isobutyl-2,5,8,11,12-pentaoxo-3,6,9,13-tetraazahexadec-15-en-1-yl]nicotinamide;

N-allyl-9-sec-butyl-6-(cyclohexylmethyl)-3-ethyl-12-isobutyl-2,5,8,11,14-pentaoxo-16,16-diphenyl-4,7,10,13-tetraazahexadecan-1-amide;

({3-[({1-[3-methyl-2-({4-methyl-2-[(2-pyrazinylcarbonyl)amino]pentanoyl}amino)pentanoyl]-octahydro-1H-indol-2-yl}carbonyl)amino]-2-oxopentanoyl}amino)acetic acid;

tert-butyl ({3-[({1-[3-methyl-2-({4-methyl-2-[(2-pyrazinylcarbonyl)amino]pentanoyl}amino)-pentanoyl]octahydro-1H-indol-2-yl}carbonyl)amino]-2-oxopentanoyl}amino)acetate; and (3S,6S,9S,12S)-6-(cyclohexylmethyl)-3-ethyl-12-isobutyl-9-[(1R)-1-methylpropyl]-2,5,8,11,14-pentaoxo-16,16-diphenyl-4,7,10,13-tetraazahexadecan-1-oic acid;

or a pharmaceutically acceptable salt form thereof.

[8] In another preferred embodiment, the present invention provides novel compounds of Formula I, wherein:
Q is —$(CR^{10}R^{10c})_n$—$Q^1$ or
an amino acid residue, wherein the amino acid residue comprises a natural, a modified or an unnatural amino acid.

[9] In a more preferred embodiment, the present invention provides novel compounds of Formula IIb, wherein:

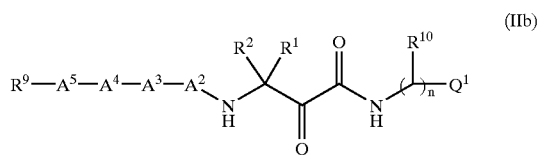

(IIb)

or a stereoisomer or pharmaceutically acceptable salt form thereof, wherein;

$R^{10}$ is selected from the group: —$CO_2R^{11}$, —$NR^{11}R^{11}$, and $C_1$–$C_6$ alkyl substituted with 0–1 $R^{10a}$;

$R^{10a}$ is selected from the group: halo, —$NO_2$, —CN, —$CF_3$, —$CO_2R^{11}$, —$NR^{11}R^{11}$, —$OR^{11}$, —$SR^{11}$, —C(=NH)$NH_2$, and aryl substituted with 0–1 $R^{10b}$;

$R^{10b}$ is selected from the group: —$CO_2H$, —$NH_2$, —OH, —SH, and
—C(=NH)$NH_2$;

$R^{10c}$ is H or $C_1$–$C_4$ alkyl;

alternatively, $R^{10}$ and $R^{10c}$ can be combined to form a $C_3$–$C_6$ cycloalkyl group substituted with 0–1 $R^{10a}$;

$R^{11}$ is, at each occurrence, independently H or $C_1$–$C_4$ alkyl;

$R^{11a}$ is H, $C_1$–$C_4$ alkyl, $C_1$–$C_4$ haloalkyl, $C_2$–$C_4$ alkenyl, $C_2$–$C_4$ alkynyl, aryl, aryl($C_1$–$C_4$ alkyl)-, $C_3$–$C_6$ cycloalkyl, or $C_3$–$C_6$ cycloalkyl($C_1$–$C_4$ alkyl)-;

$Q^1$ is selected from:
—$CO_2R^{11}$, —$SO_2R^{11}$, —$SO_3R^{11}$, —$P(O)_2R^{11}$, —$P(O)_3R^{11}$,
aryl substituted with 0–4 $Q^{1a}$, and
5–6 membered heterocyclic group consisting of carbon atoms and 1–4 heteroatoms selected from the group: O, S, and N, said heterocyclic group substituted with 0–4 $Q^{1a}$;

$Q^{1a}$ is H, F, Cl, Br, I, —$NO_2$, —CN, —NCS, —$CF_3$,
—$OCF_3$, —$CH_3$,
—$OCH_3$, —$CO_2R^{19}$, —C(=O)$NR^{19}R^{19}$, —NHC(=O)$R^{19}$, —$SO_2R^{19}$,
—$SO_2NR^{19}R^{19}$, —$NR^{19}R^{19}$, —$OR^{19}$, —$SR^{19}$, $C_1$–$C_4$ alkyl, $C_1$–$C_4$ alkoxy, $C_1$–$C_4$ haloalkyl, or $C_1$–$C_4$ haloalkoxy;

$R^{19}$ is $C_1$–$C_4$ alkyl, $C_1$–$C_4$ haloalkyl, aryl, aryl($C_1$–$C_4$ alkyl), $C_3$–$C_6$ cycloalkyl, or $C_3$–$C_6$ cycloalkyl($C_1$–$C_4$ alkyl);

alternatively, $NR^{19}R^{19}$ may form a 5–6 membered heterocyclic group consisting of carbon atoms, a nitrogen atom, and optionally a second heteroatom selected from the group: O, S, and N;

$A^2$ is a bond, —NH—$CR^3R^4$—C(=O)—, an amino acid residue,

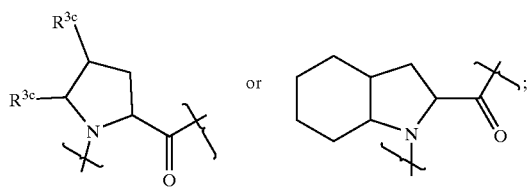

$A^3$ is a bond, —NH—$CR^5R^6$—C(=O)—, or an amino acid residue;

$A^4$ is a bond, —NH—$CR^7R^8$—C(=O)—, or an amino acid residue;

$A^5$ is a bond or an amino acid residue;

$A^7$ is a bond or an amino acid residue;

$A^8$ is an amino acid residue;

$A^9$ is an amino acid residue;

$R^1$ is selected from the group: H, F,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH,
—$CO_2R^{1b}$, —$SO_2R^{1b}$, —$SO_3R^{1b}$, —$P(O)_2R^{1b}$,
—$P(O)_3R^{1b}$,
—C(=O)$NHR^{1b}$, —NHC(=O)$R^{1b}$, —$SO_2NHR^{1b}$,
—$OR^{1b}$, —$SR^{1b}$,
$C_1$–$C_3$ alkyl, $C_3$–$C_6$ cycloalkyl, $C_1$–$C_6$ alkoxy,
—S—($C_1$–$C_6$ alkyl), aryl substituted with 0–5 $R^{1c}$,
—O—$(CH_2)_q$-aryl substituted with 0–5 $R^{1c}$,
—S—$(CH_2)_q$-aryl substituted with 0–5 $R^{1c}$, and
5–10 membered heterocyclic group consisting of carbon atoms and 1–4 heteroatoms selected from the group: O, S, and N, and substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocyle substituted with 0–5 $R^{1c}$,
aryl substituted with 0–5 $R^{1C}$, or
5–6 membered heterocyclic group consisting of carbon atoms and 1–4 heteroatoms selected from the group: O, S, and N, said heterocyclic group substituted with 0–4 $R^{1c}$;

$R^{1c}$ is selected at each occurrence from: $C_1$–$C_4$ alkyl, Cl, F, Br, I, OH, $C_1$–$C_4$ alkoxy, —CN, —$NO_2$, $C(O)OR^{1d}$, $NR^{1d}R^{1d}$, $CF_3$, and $OCF_3$;

$R^1$ is H or $C_1$–$C_4$ alkyl;
$R^2$ is H, F, or $C_1$–$C_4$ alkyl;
$R^3$ is selected from the group: H,
$C_1$–$C_6$ alkyl substituted with 0–4 $R^{3a}$,
$C_2$–$C_6$ alkenyl substituted with 0–4 $R^{3a}$,
$C_2$–$C_6$ alkynyl substituted with 0–4 $R^{3a}$,
—$(CH_2)_q$—$C_3$–$C_6$ cycloalkyl substituted with 0–4 $R^{3b}$,
—$(CH_2)_q$-aryl substituted with 0–5 $R^{3b}$, and
—$(CH_2)_q$-5–10 membered heterocyclic group consisting of carbon atoms and 1–4 heteroatoms selected from the group: O, S, and N, and said heterocyclic group is substituted with 0–2 $R^{3b}$;

$R^{3a}$ is selected from the group: —$CO_2R^{11}$, —$NR^{11}R^{11}$, —$OR^{11}$,
—$SR^{11}$, —$C(=NH)NH_2$, and aryl substituted with $R^{10b}$;
$R^{3b}$ is selected from the group: —$CO_2H$, —$NH_2$, —OH, —SH, and —$C(=NH)NH_2$;
$R^{3c}$ is, at each occurrence, independently selected from: H, $C_1$–$C_6$ alkyl, —OH, and $OR^{3d}$;
$R^{3d}$ is $C_1$–$C_6$ alkyl, $C_2$–$C_6$ alkenyl, $C_2$–$C_6$ alkynyl,
—$(CH_2)_q$—$C_3$–$C_6$ cycloalkyl, —$(CH_2)_q$-aryl, or
—$(CH_2)_q$-(5–10 membered heterocyclic group), wherein said heterocyclic group consists of carbon atoms and 1–4 heteroatoms selected from the group: O, S, and N;

$R^4$ is selected from the group: H, $C_1$–$C_6$ alkyl, phenyl, phenylmethyl-, phenylethyl-, $C_3$–$C_6$ cycloalkyl,
$C_3$–$C_6$ cycloalkylmethyl-, and $C_3$–$C_6$ cycloalkylethyl-;
$R^5$ and $R^7$ are independently H or $R^3$;
$R^6$ and $R^8$ are independently H or $R^4$;
$R^9$ is selected from the group: —$S(=O)R^{9a}$, —$S(=O)_2R^{9a}$,
—$C(=O)R^{9a}$, —$C(=O)OR^{9a}$,
—$C(=O)NHR^{9a}$, $C_1$–$C_3$ alkyl-$R^{9a}$,
$C_2$–$C_6$ alkenyl-$R^{9a}$, and $C_2$–$C_6$ alkynyl-$R^{9a}$;
$R^{9a}$ is selected from the group:
$C_1$–$C_6$ alkyl substituted with 0–3 $R^{9b}$,
$C_3$–$C_6$ cycloalkyl substituted with 0–3 $R^{9c}$,
aryl substituted with 0–3 $R^{9c}$, and
5–14 membered heterocyclic group consisting of carbon atoms and 1–4 heteroatoms selected from the group: O, S, and N, and said heterocyclic group is substituted with 0–3 $R^{9c}$;

$R^{9b}$ is selected from the group: phenyl, naphthyl, benzyl, and 5–10 membered heterocyclic group consisting of carbon atoms and 1–4 heteroatoms selected from the group: O, S, and N, and $R^{9b}$ is substituted with 0–3 $R^{9c}$;
$R^{9c}$ is selected at each occurrence from the group:
$CF_3$, $OCF_3$, Cl, F, Br, I, =O, OH, phenyl, $C(O)OR^{11}$, $NH_2$, $NH(CH_3)$, $N(CH_3)_2$, —CN, $NO_2$;
$C_1$–$C_4$ alkyl substituted with 0–3 $R^{9d}$,
$C_1$–$C_4$ alkoxy substituted with 0–3 $R^{9d}$,
$C_3$–$C_6$ cycloalkyl substituted with 0–3 $R^{9d}$,
aryl substituted with 0–5 $R^{9d}$, and
5–6 membered heterocyclic group consisting of carbon atoms and 1–4 heteroatoms selected from the group: O, S, and N, and said heterocyclic group is substituted with 0–4 $R^{9d}$;
$R^{9d}$ is selected at each occurrence from the group:
$C_1$–$C_4$ alkyl, $C_1$–$C_4$ alkoxy, $CF_3$, $OCF_3$, Cl, F, Br, I, =O, OH, phenyl, $C(O)OR^{11}$, $NB_2$, $NH(CH_3)$, $N(CH_3)_2$, —CN, and $NO_2$;
n is 1, 2, or 3; and
p is 1 or 2; and
q, at each occurence, is independently 0, 1 or 2.

[10] In a further more preferred embodiment, the present invention provides novel compounds of Formula IIb, wherein:
$R^{10}$ is selected from the group: —$CO_2R^{11}$, —$NR^{11}R^{11}$, and $C_1$–$C_6$ alkyl substituted with 0–1 $R^{10a}$;
$R^{10a}$ is selected from the group: halo, —$NO_2$, —CN, —$CF_3$, —$CO_2R^{11}$, —$NR^{11}R^{11}$, —$OR^{11}$, —$SR^{11}$, —$C(=NH)NH_2$, and aryl substituted with 0–1 $R^{10b}$;
$R^{10b}$ is selected from the group: —$CO_2H$, —$NH_2$, —OH, —SH, and —$C(=NH)NH_2$;
$R^{10c}$ is H or $C_1$–$C_4$ alkyl;
alternatively, $R^{10}$ and $R^{10c}$ can be combined to form a $C_3$–$C_6$ cycloalkyl group substituted with 0–1 $R^{10a}$;
$R^{11}$ is, at each occurrence, independently H or $C_1$–$C_4$ alkyl;
$R^{11a}$ is H, $C_1$–$C_4$ alkyl, $C_1$–$C_4$ haloalkyl, $C_2$–$C_4$ alkenyl,
$C_2$–$C_4$ alkynyl, aryl, aryl($C_1$–$C_4$ alkyl)-,
$C_3$–$C_6$ cycloalkyl, or $C_3$–$C_6$ cycloalkyl($C_1$–$C_4$ alkyl)-;
$Q^1$ is selected from:
—$CO_2R^{11}$, —$SO_2R^{11}$, —$SO_3R^{11}$, —$P(O)_2R^{11}$,
—$P(O)_3R^{11}$,
aryl substituted with 0–4 $Q^{1a}$, and
5–6 membered heterocyclic group consisting of carbon atoms and 1–4 heteroatoms selected from the group: O, S, and N, said heterocyclic group substituted with 0–4 $Q^{1a}$;
$Q^{1a}$ is H, F, $C_1$, Br, I, —$NO_2$, —CN, —NCS, —$CF_3$,
—$OCF_3$, —$CH_3$,
—$OCH_3$, —$CO_2R^{19}$, —$C(=O)NR^{19}R^{19}$, —$NHC(=O)R^{19}$, —$SO_2R^{19}$,
—$SO_2NR^{19}R^{19}$, —$NR^{19}R^{19}$, —$OR^{19}$, —$SR^{19}$, $C_1$–$C_4$ alkyl, $C_1$–$C_4$ alkoxy, $C_1$–$C_4$ haloalkyl, or $C_1$–$C_4$ haloalkoxy;
$R^{19}$ is $C_1$–$C_4$ alkyl, $C_1$–$C_4$ haloalkyl, aryl, aryl($C_1$–$C_4$ alkyl), $C_3$–$C_6$ cycloalkyl, or $C_3$–$C_6$ cycloalkyl($C_1$–$C_4$ alkyl);
alternatively, $NR^{19}R^{19}$ may form a piperidinyl, piperazinyl, or morpholinyl group;
$A^2$ is a bond, —NH—$CR^3R^4$—$C(=O)$—, an amino acid residue,

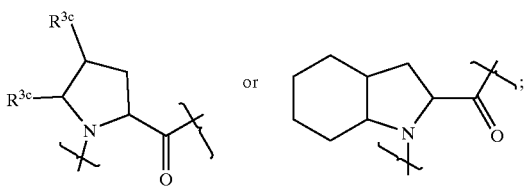

$A^3$ is a bond or an amino acid residue;
$A^4$ is a bond or an amino acid residue;
$A^5$ is a bond;
$R^1$ is selected from the group: H,
  $C_1$–$C_6$ alkyl substituted with 0–3 $R^{1a}$,
  $C_2$–$C_6$ alkenyl substituted with 0–3 $R^{1a}$,
  $C_2$–$C_6$ alkynyl substituted with 0–3 $R^{1a}$, and
  $C_3$–$C_6$ cycloalkyl substituted with 0–3 $R^{1a}$;
$R^{1a}$ is selected at each occurrence from the group:
  Cl, F, Br, I, $CF_3$, $CHF_2$, OH, =O, SH,
  —$CO_2R^{1b}$, —$SO_2R^{1b}$, —$SO_3R^{1b}$, —$P(O)_2R^{1b}$,
    —$P(O)_3R^{1b}$,
  —$C(=O)NHR^{1b}$, —$NHC(=O)R^{1b}$, —$SO_2NHR^{1b}$,
    —$OR^{1b}$, —$SR^{1b}$,
  $C_1$–$C_3$ alkyl, $C_3$–$C_6$ cycloalkyl, $C_1$–$C_6$ alkoxy,
  —S—($C_1$–$C_6$ alkyl), aryl substituted with 0–5 $R^{1c}$,
  —O—$(CH_2)_q$-aryl substituted with 0–5 $R^{1c}$,
  —S—$(CH_2)_q$-aryl substituted with 0–5 $R^{1c}$, and
  5–10 membered heterocyclic group consisting of carbon atoms and 1–4 heteroatoms selected from the group: O, S, and N, and substituted with 0–3 $R^{1c}$;
$R^{1b}$ is H,
  $C_1$–$C_4$ alkyl substituted with 0–3 $R^{1c}$,
  $C_2$–$C_4$ alkenyl substituted with 0–3 $R^{1c}$,
  $C_2$–$C_4$ alkynyl substituted with 0–3 $R^{1c}$,
  $C_3$–$C_6$ cycloalkyl substituted with 0–5 $R^{1c}$,
  $C_3$–$C_6$ carbocycle substituted with 0–5 $R^{1c}$,
  aryl substituted with 0–5 $R^{1c}$, or
  5–6 membered heterocyclic group consisting of carbon atoms and 1–4 heteroatoms selected from the group: O, S, and N, said heterocyclic group substituted with 0–4 $R^{1c}$;
$R^{1c}$ is selected at each occurrence from: $C_1$–$C_4$ alkyl, Cl, F, Br, I, OH, $C_1$–$C_4$ alkoxy, —CN, —$NO_2$, $C(O)OR^{1d}$, $NR^{1d}R_{1d}$, $CF_3$, and $OCF_3$;
$R^{1d}$ is H or $C_1$–$C_4$ alkyl;
$R^2$ is H or $C_1$–$C_4$ alkyl;
$R^3$ is selected from the group: H,
  $C_1$–$C_6$ alkyl substituted with 0–4 $R^{3a}$,
  $C_2$–$C_6$ alkenyl substituted with 0–4 $R^{3a}$,
  $C_2$–$C_6$ alkynyl substituted with 0–4 $R^{3a}$,
  —$(CH_2)_q$—$C_3$–$C_6$ cycloalkyl substituted with 0–4 $R^{3b}$,
  —$(CH_2)_q$-aryl substituted with 0–5 $R^{3b}$, and
  —$(CH_2)_q$-5–10 membered heterocyclic group consisting of carbon atoms and 1–4 heteroatoms selected from the group: O, S, and N, and said heterocyclic group is substituted with 0–2 $R^{3b}$;
$R^{3a}$ is selected from the group: —$CO_2R^{11}$, —$NR^{11}R^{11}$, —$OR^{11}$,
  —$SR^{11}$, —$C(=NH)NH_2$, and aryl substituted with $R^{10b}$;
$R^{3b}$ is selected from the group: —$CO_2H$, —$NH_2$, —OH, —SH, and —$C(=NH)NH_2$;
$R^{3c}$ is, at each occurrence, independently selected from: H, $C_1$–$C_6$ alkyl, —OH, and $OR^{3d}$;
$R^{3d}$ is $C_1$–$C_6$ alkyl, $C_2$–$C_6$ alkenyl, $C_2$–$C_6$ alkynyl,
  —$(CH_2)_q$—$C_3$–$C_6$ cycloalkyl, —$(CH_2)_q$-aryl, or
  —$(CH_2)_q$-(5–10 membered heterocyclic group), wherein said heterocyclic group consists of carbon atoms and 1–4 heteroatoms selected from the group: O, S, and N;
$R^4$ is selected from the group: H, $C_1$–$C_6$ alkyl, phenyl, phenylmethyl-, phenylethyl-, $C_3$–$C_6$ cycloalkyl,
  $C_3$–$C_6$ cycloalkylmethyl-, and $C_3$–$C_6$ cycloalkylethyl-;
$R^9$ is selected from the group: —$S(=O)_2R^{9a}$, —$C(=O)R^{9a}$,
  $C_1$–$C_3$ alkyl-$R^{9a}$, $C_2$–$C_6$ alkenyl-$R^{9a}$, and
  $C_2$–$C_6$ alkynyl-$R^{9a}$;
$R^{9a}$ is selected from the group:
  $C_1$–$C_6$ alkyl substituted with 0–3 $R^{9b}$,
  $C_3$–$C_6$ cycloalkyl substituted with 0–3 $R^{9c}$,
  aryl substituted with 0–3 $R^{9c}$, and
  5–14 membered heterocyclic group consisting of carbon atoms and 1–4 heteroatoms selected from the group: O, S, and N, and said heterocyclic group is substituted with 0–3 $R^{9c}$;
$R^{9b}$ is selected from the group: phenyl, naphthyl, benzyl, and 5–10 membered heterocyclic group consisting of carbon atoms and 1–4 heteroatoms selected from the group: O, S, and N, and $R^{9b}$ is substituted with 0–3 $R^{9c}$;
$R^{9c}$ is selected at each occurrence from the group:
  $CF_3$, $OCF_3$, Cl, F, Br, I, =O, OH, phenyl, $C(O)OR^{11}$,
  $NH_2$, $NH(CH_3)$, $N(CH_3)_2$, —CN, $NO_2$;
  $C_1$–$C_4$ alkyl substituted with 0–3 $R^{9d}$,
  $C_1$–$C_4$ alkoxy substituted with 0–3 $R^{9d}$,
  $C_3$–$C_6$ cycloalkyl substituted with 0–3 $R^{9d}$,
  aryl substituted with 0–5 $R^{9d}$, and
  5–6 membered heterocyclic group consisting of carbon atoms and 1–4 heteroatoms selected from the group: O, S, and N, and said heterocyclic group is substituted with 0–4 $R^{9d}$;
$R^{9d}$ is selected at each occurrence from the group:
  $C_1$–$C_4$ alkyl, $C_1$–$C_4$ alkoxy, $CF_3$, $OCF_3$, Cl, F, Br, I, =O, OH, phenyl, $C(O)OR^{11}$, $NH_2$, $NH(CH_3)$, $N(CH_3)_2$, —CN, and $NO_2$;
n is 1 or 2; and
p is 1 or 2; and
q, at each occurence, is independently 0, 1 or 2.

[11] In an even more preferred embodiment, the present invention provides novel compounds of Formula IIIb, wherein:

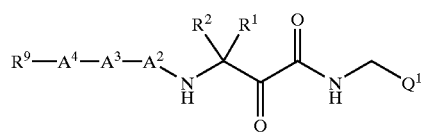

(IIIb)

or a stereoisomer or pharmaceutically acceptable salt form thereof, wherein;
$Q^1$ is selected from:
  —$C_2R^{11}$, —$SO_2R^{11}$, —$SO_3R^{11}$, —$P(O)_2R^{11}$,
    —$P(O)_3R^{11}$,
  aryl substituted with 0–4 $Q^{1a}$, and
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–4 $Q^{1a}$;

$Q^{1a}$ is H, F, Cl, Br, I, —$NO_2$, —CN, —NCS, —$CF_3$, —$OCF_3$, —$CH_3$,
—$OCH_3$, —$CO_2R^{19}$, —C(=O)$NR^{19}R^{19}$, —NHC(=O)$R^{19}$, —$SO_2R^{19}$,
—$SO_2NR^{19}R^{19}$, —$NR^{19}R^{19}$, —$OR^{19}$, —$SR^{19}$, $C_1$–$C_4$ alkyl, $C_1$–$C_4$ alkoxy, $C_1$–$C_4$ haloalkyl, or $C_1$–$C_4$ haloalkoxy;

$R^{19}$ is $C_1$–$C_4$ alkyl, $C_1$–$C_4$ haloalkyl, aryl, aryl($C_1$–$C_4$ alkyl), $C_3$–$C_6$ cycloalkyl, or $C_3$–$C_6$ cycloalkyl($C_1$–$C_4$ alkyl);

alternatively, $NR^{19}R^{19}$ may form a piperidinyl, piperazinyl, or morpholinyl group;

$A^2$ is a bond, —NH—$CR^3R^4$—C (=O)—, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, Val,

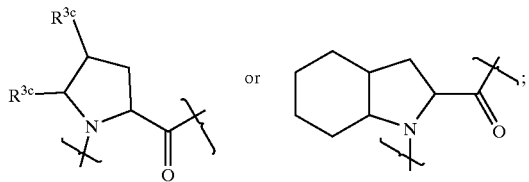

$A^3$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

$A^4$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

$R^1$ is selected from the group: H,
$C_1$–$C_6$ alkyl substituted with 0–3 $R^{1a}$,
$C_2$–$C_6$ alkenyl substituted with 0–3 $R^{1a}$,
$C_2$–$C_6$ alkynyl substituted with 0–3 $R^{1a}$, and
$C_3$–$C_6$ cycloalkyl substituted with 0–3 $R^{1a}$;

$R^{1a}$ is selected at each occurrence from the group:
Cl, F, Br, I, $CF_3$, $CHF_2$, OH, =O, SH,
—$CO_2R^{1b}$, —$SO_2R^{1b}$, —$SO_3R^{1b}$, —$P(O)_2R^{1b}$, —$P(O)_3R^{1b}$,
—C(=O)$NHR^{1b}$, —NHC(=O)$R^{1b}$, —$SO_2NHR^{1b}$, —$OR^{1b}$, —$SR^{1b}$,
$C_1$–$C_3$ alkyl, $C_3$–$C_6$ cycloalkyl, $C_1$–$C_6$ alkoxy,
—S—($C_1$–$C_6$ alkyl),
aryl substituted with 0–5 $R^{1c}$,
—O—$(CH_2)_q$-aryl substituted with 0–5 $R_{1c}$,
—S—$(CH_2)_q$-aryl substituted with 0–5 $R^{1c}$, and
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and substituted with 0–3 $R^{1c}$;

$R^{1b}$ is H,
$C_1$–$C_4$ alkyl substituted with 0–3 $R^{1c}$,
$C_2$–$C_4$ alkenyl substituted with 0–3 $R^{1c}$,
$C_2$–$C_4$ alkynyl substituted with 0–3 $R^{1c}$,
$C_3$–$C_6$ cycloalkyl substituted with 0–5 $R^{1c}$,
$C_3$–$C_6$ carbocyle substituted with 0–5 $R^{1c}$,
aryl substituted with 0–5 $R^{1c}$, or
5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–4 $R^{1c}$;

$R^{1c}$ is selected at each occurrence from: $C_1$–$C_4$ alkyl, Cl, F, Br, I, OH, $C_1$–$C_4$ alkoxy, —CN, —$NO_2$, C(O)$OR^{1d}$, $NR^{1d}R^{1d}$, $CF_3$, and $OCF_3$;

$R^{1d}$ is H or $C_1$–$C_4$ alkyl;

$R^2$ is H or $C_1$–$C_4$ alkyl;

$R^3$ is selected from the group: H,
$C_1$–$C_6$ alkyl substituted with 0–4 $R^{3a}$,
$C_2$–$C_6$ alkenyl substituted with 0–4 $R^{3a}$,
$C_2$–$C_6$ alkynyl substituted with 0–4 $R^{3a}$,
—$(CH_2)_q$—$C_3$–$C_6$ cycloalkyl substituted with 0–4 $R^{3b}$,
—$(CH_2)_q$-aryl substituted with 0–5 $R^{3b}$, and
—$(CH_2)_q$-5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and said heterocyclic group is substituted with 0–2 $R^{3b}$;

$R^{3a}$ is selected from the group: —$CO_2R^{11}$, —$NR^{11}R^{11}$, —$OR^{11}$, —SR l, —C(=NH)$NH_2$, and aryl substituted with $R^{10b}$;

$R^{3b}$ is selected from the group: —$CO_2H$, —$NH_2$, —OH, —SH, and —C(=NH)$NH_2$;

$R^{3c}$ is, at each occurrence, independently selected from: H, $C_1$–$C_6$ alkyl, —OH, and $OR^{3d}$;

$R^{3d}$ is $C_1$–$C_6$ alkyl, $C_2$–$C_6$ alkenyl, $C_2$–$C_6$ alkynyl, —$(CH_2)_q$—$C_3$–$C_6$ cycloalkyl, —$(CH_2)_q$-aryl, or —$(CH_2)_q$-(5–10 membered heterocyclic group), wherein said heterocyclic group consists of carbon atoms and 1–4 heteroatoms selected from the group: 0, S, and N;

$R^4$ is selected from the group: H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^9$ is selected from —S(=O)$_2$R$^{9a}$ and —C(=O)R$^{9a}$;
R$^{9a}$ is selected from the group:
- phenyl substituted with 0–3 R$^{9c}$,
- naphthyl substituted with 0–3 R$^{9c}$, and
- 5–14 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and said heterocyclic group is substituted with 0–3 R$^{9c}$;

R$^{9c}$ is selected at each occurrence from the group:
- CF$_3$, OCF$_3$, Cl, F, Br, I, =O, OH, phenyl, C(O)OR$^{11}$, NH$_2$, NH(CH$_3$), N(CH$_3$)$_2$, —CN, NO$_2$;
- C$_1$–C$_4$ alkyl substituted with 0–3 R$^{9d}$,
- C$_1$–C$_4$ alkoxy substituted with 0–3 R$^{9d}$,
- C$_3$–C$_6$ cycloalkyl substituted with 0–3 R$^{9d}$,
- aryl substituted with 0–5 R$^{9d}$, and
- 5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; and said heterocyclic group is substituted with 0–4 R$^{9d}$;

R$^{9d}$ is selected at each occurrence from the group:
- C$_1$–C$_4$ alkyl, C$_1$–C$_4$ alkoxy, CF$_3$, OCF$_3$, Cl, F, Br, I, =O, OH, phenyl, C(O)OR$^{11}$, NB$_2$, NH(CH$_3$), N(CH$_3$)$_2$, —CN, and NO$_2$;

p is 1 or 2; and
q, at each occurence, is independently 0, 1 or 2.

In another embodiment, the present invention provides a novel pharmaceutical composition comprising a pharmaceutically acceptable carrier and a therapeutically effective amount of a compound of Formula (I), (II), (III), (IIb), (IIIb) or pharmaceutically acceptable salt form thereof.

In another embodiment, the present invention provides a novel method of treating HCV infection which comprises administering to a host in need of such treatment a therapeutically effective amount of a compound of Formula (I), (IIb), (IIIb) or pharmaceutically acceptable salt form thereof.

In another embodiment, the present invention provides novel compounds of Formula (I), (II), (III), (IIb), (IIIb) or pharmaceutically acceptable salt forms thereof for use in therapy.

In another embodiment, the present invention provides the use of novel compounds of Formula (I), (II), (III), (IIb), (IIIb) or pharmaceutically acceptable salt forms thereof for the manufacture of a medicament for the treatment of HCV.

Definitions

The compounds herein described have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Geometric isomers of double bonds such as olefins and C=N double bonds can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., R$^{1a}$) occurs more than one time in any constituent or formula for a compound, its definition at each occurrence is independent of its definition at every other occurrence. Thus, for example, if a group is shown to be substituted with 0–3 R$^{1a}$, then said group may optionally be substituted with up to three R$^{1a}$ groups and R$^{1a}$ at each occurrence is selected independently from the definition of R$^{1a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms. For example, "C$_1$–C$_{10}$ alkyl" (or alkylene), is intended to include C$_1$, C$_2$, C$_3$, C$_4$, C$_5$, C$_6$, C$_7$, C$_8$, C$_9$, and C$_{10}$ alkyl groups. Additionally, for example, "C$_1$–C$_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. For example, "$C_2$–$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain. For example, "$C_2$–$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. For example, "$C_1$–$C_6$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

As used herein, "carbocycle" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated partially unsaturated or unsaturated (ie. aromatic or "heteroaryl"), and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized to —NO—, —SO—, or —$SO_2$—. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 2-pyrrolidonyl, 2H,6H-1,5,2-dithiazinyl, 2H-pyrrolyl, 3H-indolyl, 4-piperidonyl, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aryl", "$C_6$–$C_{10}$ aryl" or "aromatic residue", is intended to mean an aromatic moiety containing, if specified, the specified number of carbon atoms. For example, aryl is phenyl, pyridinyl or naphthyl. Unless otherwise specified, "aryl", "$C_6$–$C_{10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. "Natural amino acids" include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-CBZ-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used throughout the specification, the following abbreviations for amino acid residues or amino acids apply:

Abu is L-aminobutyric acid;
Ala is L-alanine;
Alg is L-2-amino-4-pentenoic acid;
Ape is L-2-aminopentanoic acid;
Arg is L-arginine;
Asn is L-asparagine;
Asp is L-aspartic acid;
Aze is azedine-2-carboxlic acid;
Cha is L-2-amino-3-cyclohexylpropionic acid;
Cpa is L-2-amino-3-cyclopropylpropionic acid
Cpg is L-2-amino-2-cyclopropylacetic acid;
Cys is L-cysteine;
Dfb is L-4,4'-difluoro-1-amino-butyric acid;
Dpa is L-2-amino-3,3-diphenylpropionic acid
Gln is L-glutamine;
Glu is L-glutamic acid;
Gly is glycine;
His is L-histidine;
HomoLys is L-homolysine;
Hyp is L-4-hydroxyproline;
Ile is L-isoleucine;
Irg is isothiouronium analog of L-Arg;
Leu is L-leucine;
Lys is L-lysine;
Met is L-methionine;
Orn is L-ornithine;
Phe is L-phenylalanine;
Phe(4-fluoro) is para-fluorophenylalanine;
Pro is L-proline;
Sar is L-sarcosine;
Ser is L-serine;
Thr is L-threonine;
Tpa is L-2-amino-5,5,5-trifluoropentanoic acid;
Trp is L-tryptophan;
Tyr is L-tyrosine;
Val is L-valine; and
HyPOBn: O-benzyl hydroxylproline.

"Amino acid residue" as used herein, refers to natural, modified or unnatural amino acids of either D- or L-configuration and means an organic compound containing both a basic amino group and an acidic carboxyl group. Natural amino acids residues are Ala, Arg, Asn, Asp, Aze, Cys, Gln, Glu, Gly, His, Hyp, Ile, Irg Leu, Lys, Met, Orn, Phe, Phe(4-fluoro), Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose. Additionally, said reference describes, but does not extensively list, acylic N-alkyl and acyclic α,α-disubstituted amino acids. Included in the scope of the present invention are N-alkyl, aryl, and alkylaryl analogs of both in chain and N-terminal amino acid residues. Similarly, alkyl, aryl, and alkylaryl maybe substituted for the alpha hydrogen. Illustrated below are examples of N-alkyl and alpha alkyl amino acid residues, respectively.

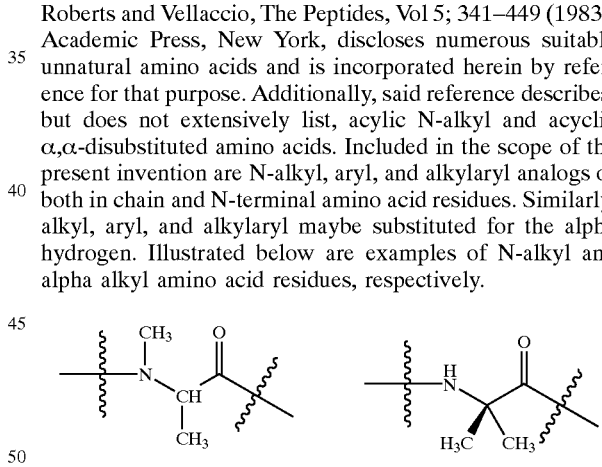

Unnatural amino acids that fall within the scope of this invention are by way of example and without limitation: 2-aminobutanoicacid, 2-aminopentanoic acid, 2-aminohexanoic acid, 2-aminoheptanoicacid, 2-aminooctanoic acid, 2-aminononanoic acid, 2-aminodecanoic acid, 2-aminoundecanoic acid, 2-amino-3,3-dimethylbutanoic acid, 2-amino-4,4-dimethylpentanoic acid, 2-amino-3-methylhexanoic acid, 2-amino-3-methylheptanoic acid, 2-amino-3-methyloctanoic acid, 2-amino-3-methylnonanoic acid, 2-amino-4-methylhexanoic acid, 2-amino-3-ethylpentanoic acid, 2-amino-3,4-dimethylpentanoic acid, 2-amino-3,5-dimethylhexanoic acid, 2-amino-3,3-dimethylpentanoic acid, 2-amino-3-ethyl-3-methylpentanoic acid, 2-amino-3,3-diethylpentanoic acid, 2-amino-5-methylhexanoic acid, 2-amino-6- methylheptanoic, 2-amino-7-methyloctanoic, 2-amino-2-cyclopentylacetic, 2-amino-2-cylcohexylacetic acid, 2-amino-2-(1-methylcylcohexyl)acetic acid, 2-amino-2-(2-methyl-1-methylcylcohexyl)acetic acid, 2-amino-2-(3-methyl-1-methylcylcohexyl)acetic acid, 2-amino-2-(4-methyl-methylcylcohexyl)acetic acid, 2-amino-2-(1-ethylcycolhexyl)acetic acid, 2-amino-3-(cyclohexyl) propanoic acid, 2-amino-4-(cyclohexyl)butanoic acid, 2-amino-3-(l-adamantyl)propanoic acid, 2-amino-3-butenoic acid, 2-amino-3-methyl-3-butenoic acid, 2-amino-4-pentenoic acid, 2-amino-4-hexenoic acid, 2-amino-5-heptenoic acid, 2-amino-4-methyl-4-hexenoic acid, 2-amino-5-methyl-4-hexenoic acid, 2-amino-4-methy-5-hexenoic acid, 2-amino-6-heptenoic acid, 2-amino-3,3,4-trimethyl-4-pentenoic acid, 2-amino-4-chloro-4-pentenoic, 2-amino-4,4-dichloro-3-butenoic acid, 2-amino-3-(2-methylenecyclopropyl)-propanoic acid, 2-amino-2-(2-cyclopentenyl)acetic acid, 2-amino-2-(cyclohexenyl)acetic acid, 2-amino-3-(2-cyclopentenyl) propanoic acid, 2-amino-3-(3-cyclopentenyl)propanoic acid, 2-amino-3-(1-cyclohexyl)propanoic acid, 2-amino-2-(1-cyclopentenyl)acetic acid, 2-amino-2-(1-cylcohexyl) acetic acid, 2-amino-2-(1-cylcoheptenyl)acetic acid, 2-amino-2-(1-cyclooctenyl)acetic acid, 2-amino-3-(1-cycloheptenyl)propanoic acid, 2-amino-3-(1,4-cyclohexadienyl)propanoic acid, 2-amino-3-(2,5-cyclohexadienyl)propanoic acid, 2-amino-2-(7-cycloheptatrienyl)acetic acid, 2-amino-4,5-hexadienoic acid, 2-amino-3-butynoic acid, 2-amino-4-pentyoic acid, 2-amino-4-hexynoic acid, 2-amino-4-hepten-6-ynoic acid, 2-amino-3-fluoropropanoic acid, 2-amino-3,3,3-trifluoropropanoic acid, 2-amino-3-fluorobutanoic acid, 2-amino-3-fluoropentanoic acid, 2-amino-3-fluorohexanoic acid, 2-amino-3,3-difluorobutanoic acid, 2-amino-3,3-difluoro-3-phenylpropanoic acid, 2-amino-3-perfluoroethylpropanoic acid, 2-amino-3-perfluoropropylpropanoic acid, 2-amino-3-fluoro-3-methylbutanoic acid, 2-amino-5,5,5-trifluoropentanoic acid, 2-amino-3-methyl-4,4,4-trifluorobutanoic acid, 2-amino-3-trifluoromethyl-4,4,4-trifluorobutanoic acid, 2-amino-3,3,4,4,5,5-heptafluoropentanoic acid, 2-amino-3-methyl-5-fluoropentanoic acid, 2-amino-3-methyl-4-fluoropentanoic acid, 2-amino-5,5-difluorohexanoic acid, 2-amino-4-(fluoromethyl)-5-fluoropentanoic acid, 2-amino-4-trifluoromethyl-5,5,5-trifluoropentanoic acid, 2-amino-3-fluoro-3-methylbutanoic acid, 2-amino-3-fluoro-3-phenylpentanoic acid, 2-amino-2-(1-fluorocyclopentyl)acetic acid, 2-amino-2-(1-fluorocyclohexyl)acetic acid, 2-amino-3-chloropropanoic acid acid, 2-amino-3-chlorobutanoic acid acid, 2-amino-4,4-dichlorobutanoic acid acid, 2-amino4,4,4-trichlorobutanoic acid, 2-amino-3,4,4-trichlorobutanoic acid, 2-amino-6-chlorohexanoic acid, 2-amino-4-bromobutanoic acid, 2-amino-3-bromobutanoic acid, 2-amino-3-mercaptobutanoic acid, 2-amino-4-mercaptobutanoic acid, 2-amino-3-mercapto-3,3-dimethylpropanoic acid, 2-amino-3-mercapto-3-methylpentanoic acid, 2-amino-3-mercaptopentanoic acid, 2-amino-3-mercapto-4-methylpentanoic acid, 2-amino-3-methyl-4-mercaptopentanoic acid, 2-amino-5-mercapto-5-methylhexanoic acid, 2-amino-2-(1-mercaptocyclobutyl)acetic acid, 2-amino-2-(1-mercaptocyclopentyl)acetic acid, 2-amino-2-(1-mercaptocyclohexyl)acetic acid, 2-amino-5-(methylthio) pentanoic acid, 2-amino-6-(methylthio)hexanoic acid, 2-amino-4-methylthio-3-phenylbutanoic acid, 2-amino-5-ethylthio-5-methylpentanoic acid, 2-amino-5-ethylthio-3,5,5-trimethylpentanoic acid, 2-amino-5-ethylthio-5-phenylpentanoic acid, 2-amino-5-ethylthio-5-pentanoic acid, 2-amino-5-butylthio-5-methylpentanoic acid, 2-amino-5-butylthio-3,5,5-trimethylpentanoic acid, 2-amino-5-butylthio-5-phenylpentanoic acid, 2-amino-5-(butylthio)pentanoic acid, 2-amino-3-methy4-hydroselenopentanoic acid, 2-amino-4-methylselenobutanoic acid, 2-amino-4-ethylselenobutanoic acid, 2-amino-4-benzylselenobutanoic acid, 2-amino-3-methyl-4-(methylseleno)butanoic acid, 2-amino-3-(aminomethylseleno)propanoic acid, 2-amino-3-(3-aminopropylseleno)propanoic acid, 2-amino-4-methyltellurobutanoic acid, 2-amino-4-hydroxybutanoic acid, 2-amino-4-hydroxyhexanoic acid, 2-amino-3-hydroxypentanoic acid, 2-amino-3-hydroxyhexanoic acid, 2-amino-3methyl-4-hydroxybutanoic acid, 2-amino-3-hydroxy-3-methylbutanoic acid, 2-amino-6-hydroxyhexanoic acid, 2-amino-4-hydroxyhexanoic acid, 2-amino-3-hydroxy-4-methylpentanoic acid, 2-amino-3-hydroxy-3-methylpentanoic acid, 2-amino4-hydroxy-3,3-dimethylbutanoic acid, 2-amino-3-hydroxy4-methylpentanoic acid, 2-amino-3-hydroybutanedioic acid, 2-amino-3-hydroxy-3-phenyl-propanoic acid, 2-amino-3-hydroxy-3-(4-nitrophenyl)propanoic acid, 2-amino-3-hydroxy-3-(3-pyridyl)propanoic acid, 2-amino-2-(1-hydroxycyclopropyl) acetic acid, 2-amino-3-(1-hydroxycyclohexyl)propanoic acid, 2-amino-3-hydroxy-3-phenylpropanoic acid, 2-amino-3-hydroxy-3-[3-bis (2-chloroethyl)aminophenyl]propanoic acid, 2-amino-3-hydroxy-3-(3,4-dihydroxyphenyl)propanoic acid, 2-amino-3-hydroxy-3-(3,4-methylenedioxyphenyl) propanoic acid, 2-amino-4-fluoro-3-hydroxybutanoic acid, 2-amino-4,4,4-trichloro-3-hydroxybutanoic acid, 2-amino-3-hydroxy-4-hexynoic acid, 2-amino-3,4-dihydroxybutanoic acid, 2-amino-3,4,5,6-tetrahydroxyhexanoic acid, 2-amino-4,5-dihydroxy-3-methylpentanoic acid, 2-amino-5,6-dihydroxyhexanoic acid, 2-amino-5-hydroxy-4-(hydroxymethyl)pentanoic acid, 2-amino-4,5-dihydroxy-4-(hydroxymethyl)pentanoic acid, 2-amino-3-hydroxy-5-benzyloxypentanoic acid, 2-amino-3-(2-aminoethoxy)propanoic acid, 2-amino-4-(2-aminoethoxy)butanoic acid, 2-amino-4-oxobutanoic acid, 2-amino-3-oxobutanoic acid, 2-amino-4-methyl-3-oxopentanoic acid, 2-amino-3-phenyl-3-oxopropanoic acid, 2-amino-4-phenyl-3-oxobutanoic acid, 2-amino-3-methyl-4-oxopentanoic acid, 2-amino-4-oxo-4-(4-hydroxyphenyl)butanoic acid, 2-amino-4-oxo-4-(2-furyl)butanoic acid, 2-amino-4-oxo-4-(2-nitrophenyl)butanoic acid, 2-amino-4-oxo-4-(2-amino-4-chlorophenyl)butanoic acid, 2-amino-3-(4-oxo-1-cyclohexenyl)propanoic acid, 2-amino-3-(4-oxocyclohexanyl)propanoic acid, 2-amino-3-(2,5-dimethyl-3,6-dioxo-1,4-cyclohexadienyl) propanoic acid, 2-amino-3-(1-hydroxy-5-methyl-7-oxo-cyclohepta-1,3,5-trien-2-yl)propanoic acid, 2-amino-3-(1-hydroxy-7-oxo-cyclohepta-1,3,5-trien-3-yl)propanoic acid, 2-amino-3-(1-hydroxy-7-oxo-cyclohepta-1,3,5-trien-4-yl)propanoic acid, 2-amino-4-methoxy-3-butenoic acid, 2-amino-4-(2-aminoethoxy)-3-butenoic acid, 2-amino-4-(2-amino-3-hydroxypropyl)-3-butenoic acid, 2-amino-2-(4-methoxy-1,4-cyclohexadienyl)acetic acid, 2-amino-3,3-diethoxypropanoic acid, 2-amino-4,4-dimethylbutanoic acid, 2-amino-2-(2,3-epoxycyclohexyl) acetic acid, 2-amino-3-(2,3-epoxycyclohexy)propanoic acid, 2-amino-8-oxo-9,10-epoxydecanoic acid, 2-amino-propanedioic acid, 2-amino-3-methylbutanedioic acid, 2-amino-3,3-dimethylbutanedioic acid, 2-amino4-methylpentanedioic acid, 2-amino-3-methylpentanedioic acid, 2-amino-3-phenylpentanedioic acid, 2-amino-3-hydroxypentanedioic acid, 2-amino-3-carboxypentanedioic acid, 2-amino-4-ethylpentanedioic acid, 2-amino-4-propylpentanedioic acid, 2-amino-4-isoamylpentanedioic acid, 2-amino-4-phenylpentanedioic acid, 2-amino-hexanedioic acid, 2-amino-heptanedioic acid, 2-amino-decanedioic acid, 2-amino-octanedioic acid, 2-amino-dodecanedioic acid, 2-amino-3-methylenebutanedioic acid, 2-amino-4-methylenepentanedioic acid, 2-amino-3-fluorobutanedioic acid, 2-amino-4-fluoropentanedioic acid, 2-amino-3,3-difluorobutanedioic acid, 2-amino-3-chloropentanedioic acid, 2-amino-3-hydroxybutanedioic acid, 2-amino-4-hydroxypentanedioic acid, 2-amino-4-hydroxyhexanedioic acid, 2-amino-3,4-dihydroxypentanedioic acid, 2-amino-3-(3-hydroxypropyl)butanedioic acid, 2-amino-3-(1-carboxy-4-hydroxy-2-cyclodienyl)propanoic acid, 2-amino-3-(aceto)butanedioic acid, 2-amino-3-cyanobutanedioic acid, 2-amino-3-(2-carboxy-6-oxo-6H-pyranyl)propanoic acid, 2-amino-3-carboxybutanedioic acid, 2-amino-4-carboxypentanedioic acid, 3-amido-2-amino-3-hydroxypropanoic acid, 3-amido-2-amino-3-methylpropanoic acid, 3-amido-2-amino-3-phenylpropanoic acid, 3-amido-2,3-diaminopropanoic acid, 3-amido-2-amino-3-[N-(4-hydroxyphenyl)amino] propanoic acid, 2,3-diaminopropanoic acid, 2,3-diaminobutanoic acid, 2,4-diaminobutanoic acid, 2,4-diamino-3-methylbutanoic acid, 2,4-diamino-3-phenylbutanoic acid, 2-amino-3-(methylamino)butanoic acid, 2,5-diamino-3-methylpentanoic acid, 2,7-diaminoheptanoic acid, 2,4-diaminoheptanoic acid, 2-amino-2-(2-piperidyl)acetic acid, 2-amino-2-(1-aminocyclohexyl)acetic acid, 2,3-diamino-3-phenylpropanoic acid, 2,3-diamino-3-(4-hydroxyphenyl) propanoic acid, 2,3-diamino-3-(4-methoxyphenyl) propanoic acid, 2,3-diamino-3-[4-(N,N'-dimethyamino) phenyl]propanoic acid, 2,3-diamino-3-(3,4-dimethoxyphenyl)propanoic acid, 2,3-diamino-3-(3,4-methylenedioxyphenyl)propanoic acid, 2,3-diamino-3-(4-hydroxy-3-methoxyphenyl)propanoic acid, 2,3-diamino-3-(2-phenylethyl)propanoic acid, 2,3-diamino-3-propylpropanoic acid, 2,6-diamino-4-hexenoic acid, 2,5-diamino-4-fluoropentanoic acid, 2,6-diamino-5-fluorohexanoic acid, 2,6-diamino-4-hexynoic acid, 2,6-diamino-5,5-difluorohexanoic acid, 2,6-diamino-5,5-dimethylhexanoic acid, 2,5-diamino-3-hydroxypentanoic acid, 2,6-diamino-3-hydroxyhexanoic acid, 2,5-diamino-4-hydroxypentanoic acid, 2,6-diamino-4-hydroxyhexanoic acid, 2,6-diamino-4-oxohexanoic acid, 2,7-diaminooctanedioic acid, 2,6-diamino-3-carboxyhexanoic acid, 2,5-diamino-4-carboxypentanoic acid, 2-amino-4-(2-(N,N'-diethylamino)ethyl)pentandioic acid, 2-amino-4-(N,N'-diethylamino)pentandioic acid, 2-amino-4-(N-morpholino)pentandioic acid, 2-amino-4-(N,N'-bis(2-chloroethyl)amino)pentandioic acid, 2-amino-4-(N,N'-bis(2-hydroxyethyl)amino)pentandioic acid, 2,3,5-triaminopentanoic acid, 2-amino-3-(N-(2-aminethyl)amino)propanoic acid, 2-amino-3-((2-aminoethyl)seleno)propanoic acid, 2-amino-3-[(2-aminoethyl)thio]propanoic acid, 2-amino4-aminooxybutanoic acid, 2-amino-5-hydroxyaminopentanoic acid, 2-amino-5-[N-(5-nitro-2-pyrimidinyl)amino]pentanoic acid, 2-amino-4-[(7-nitro-2,1,3-benzoxadiazol-4-yl)amino]butanoic acid, 2-amino-3-guanidinopropanoic acid, 2-amino-3-guanidinobutanoic acid, 2-amino-4-guanidobutanoic acid, 2-amino-6-guanidohexanoic acid, 2-amino-6-ureidohexanoic acid, 2-amino-3-(2-iminoimidiazolin-4-yl)propanoic acid, 2-amino-2-(2-iminohexahydropyrimidin-4-yl)acetic acid, 2-amino-3-(2-iminohexahydropyrimidiny-4-yl)propanoic acid, 2-amino4-fluoro-5-guanidopentanoic acid, 2-amino-4-hydroxy-5-guanidopentanoic acid, 2-amino-4-guanidooxybutanoic acid, 2-amino-6-amidinohexanoic acid, 2-amino-5-(N-acetimidoylamino)pentanoic acid, 1-aminocyclopropanecarboxylic acid, 1-amino4-ethylcyclpropanecarboxylic acid, 1-aminocyclopentanecarboxylic acid, 1-aminocyclopentanecarboxylic acid, 1-amino-2,2,5,5-tetramethyl-cyclohexanecarboxylic acid, 1-aminocydoheptanecarboxylic acid, 1-aminocyclononanecarboxylic acid, 2-aminoindan-2-carboxylic acid, 2-aminonorbornane-2-carboxylic acid, 2-amino-3-phenylnorbornane-2-carboxylic acid, 3-aminotetrahydrothiophene-3-carboxylic acid, 1-amino-1,3-cyclohexanedicarboxylic acid, 3-aminopyrrolidine-3-carboxylic acid, 1,4-diaminocyclohexanecarboxylic acid, 6-alkoxy-3-amino-1,2,3,4-tetrahydrocarbazole-3-carboxylic acid, 2-aminobenzobicyclo[2,2,2]octane-2-carboxylic acid, 2-aminoindan-2-carboxylic acid, 1-amino-2-(3,4-dhydroxyphenyl)cyclopropanecarboxylic acid, 5,6-dialkoxy-2-aminoindane-2-carboxylic acid, 4,5-dihydroxy-2-aminoindan-2-caroxylic acid, 5,6-dihydroxy-2-aminotetralin-2-carboxylic acid, 2-amino-2-cyanoacetic acid, 2-amino-3-cyanopropanoic acid, 2-amino-4-cyanobutanoic acid, 2-amino-5-nitropentanoic acid, 2-amino-6-nitrohexanoic acid, 2-amino-4-aminooxybutanoic acid, 2-amino-3-(N-nitrosohydroxyamino)propanoic acid, 2-amino-3-ureidopropanoic acid, 2-amino-4-ureidobutanoic acid, 2-amino-3-phosphopropanoic acid, 2-amino-3-thiophosphopropanoic acid, 2-amino-4-methanephosphonylbutanoic acid, 2-amino-3-(trimethylsilyl)propanoic acid, 2-amino-3-(dimethyl(trimethylsilylmethylsilyl)propanoic acid, 2-amino-2-phenylacetic acid, 2-amino-2-(3-chlorophenyl)acetic acid, 2-amino-2-(4-chlorophenyl)acetic acid, 2-amino-2-(3-fluorophenyl)acetic acid, 2-amino-2-(3-methylphenyl) acetic acid, 2-amino-2-(4ofluorophenyl)acetic acid, 2-amino-2-(4-methylphenyl) acetic acid, 2-amino-2-(4-methoxyphenyl)acetic acid, 2-amino-2-(2-fluorophenyl) acetic acid, 2-amino-2-(2-methylphenyl)acetic acid, 2-amino-2-(4-choromethylphenyl)acetic acid, 2-amino-2-(4-hydroxymethylphenyl)acetic acid, 2-amino-2-[4-(methylthiomethyl)phenyl]acetic acid, 2-amino-2-(4-bromomethylphenyl)acetic acid, 2-amino-2-(4-(methoxymethy)phenyl)acetic acid, 2-amino-2-(4-((N-benzylamino)methyl)phenyl)acetic acid, 2-amino-2-(4-hydroxylphenyl)acetic acid, 2-amino-2-(3-hydroxylphenyl)acetic acid, 2-amino-2-(3-carboxyphenyl)acetic acid, 2-amino-2-(4-aminophenyl) acetic acid, 2-amino-2-(4-azidophenyl)acetic acid, 2-amino-2-(3-t-butyl-4-hydroxyphenyl)acetic acid, 2-amino-2-(3,5-difluoro-4-hydroxyphenyl)acetic acid, 2-amino-2-(3,5-dihydroxyphenyl)acetic acid, 2-amino-2-(3-carboxy-4-hydroxyphenyl)acetic acid, 2-amino-2-(3,5-di-t-butyl-4-hydroxyphenyl)acetic acid, 2-amino-3-(2-methylphenyl)propanoic acid, 2-amino-3-(4-ethylphenyl) propanoic acid, 2-amino-3-(4-phenylphenyl)propanoic acid, 2-amino-3-(4-benzylphenyl)propanoic acid, 2-amino-3-(3-fluorophenyl)propanoic acid, 2-amino-3-

(4-methylphenyl)propanoic acid, 2-amino-3-(4-fluorophenyl)propanoic acid, 2-amino-3-(4-chlorophenyl)propanoic acid, 2-amino-3-(2-chlorophenyl)propanoic acid, 2-amino-3-(4-bromophenyl)propanoic acid, 2-amino-3-(2-bromophenyl)propanoic acid, 2-amino-3-(3-hydroxyphenyl)propanoic acid, 2-amino-3-(2-hydroxyphenyl)propanoic acid, 2-amino-3-(4-mercaptophenyl)propanoic acid, 2-amino-3-(3-trifluoromethylphenyl)propanoic acid, 2-amino-3-(3-hydroxyphenyl)propanoic acid, 2-amino-3-(4-hydroxyphenyl)propanoic acid, 2-amino-3-[4-(hydroxymethy)phenyl]propanoic acid, 2-amino-3-[3-(hydroxymethyl)phenyl]propanoic acid, 2-amino-3-[3-(aminomethyl)phenyl]propanoic acid, 2-amino-3-(3-carboxyphenyl) propanoic acid, 2-amino-3-(4-nitrophenyl)propanoic acid, 2-amino-3-(4-aminophenyl)propanoic acid, 2-amino-3-(4-azidophenyl)propanoic acid, 2-amino-3-(4-cyanophenyl)propanoic acid, 2-amino-3-(4-acetophenyl)propanoic acid, 2-amino-3-(4-guanidinophenyl)propanoic acid, 2-amino-3-[4-(phenylazo)phenyl]propanoic acid, 2-amino-3-[4-(2-phenylethylenyl)phenyl]propanoic acid, 2-amino-3-(4-trialkylsilylphenyl)propanoic acid, 2-amino-3-(2,4-dimethylphenyl)propanoic acid, 2-amino-3-(2,3-dimethylphenyl)propanoic acid, 2-amino-3-(2,5-dimethylphenyl) propanoic acid, 2-amino-3-(3,5-dimethylphenyl)propanoic acid, 2-amino-3-(2,4,6-trimethylphenyl)propanoic acid, 2-amino-3-(3,4,5-trimethylphenyl)propanoic acid, 2-amino-3-(2,3,4,5,6-pentamethylphenyl)propanoic acid, 2-amino-3-(2,4,-difluorophenyl)propanoic acid, 2-amino-3-(3,4,6-difluorophenyl)propanoic acid, 2-amino-3-(2,5,difluorophenyl)propanoic acid, 2-amino-3-(2,6,-difluorophenyl)propanoic acid, 2-amino-3-(2,3,5,6-tetrafluorophenyl)propanoic acid, 2-amino-3-(3,5-dichloro-2,4,6-trifluorophenyl)propanoic acid, 2-amino-3-(2,3-difluorophenyl)propanoic acid, 2-amino-3-(2,3-bistrifluoromethylphenyl)propanoic acid, 2-amino-3-(2,4-bistrifluoromethylphenyl)propanoic acid, 2-amino-3-(2-chloro-5-trifluoromethylphenyl)propanoic acid, 2-amino-3-(2,5-difluorophenyl)propanoic acid, 2-amino-3-(2,3,4,5,6-pentafluorophenyl)propanoic acid, 2-amino-3-(2,3-dibromophenyl)propanoic acid, 2-amino-3-(2,5-dibromophenyl)propanoic acid, 2-amino-3-(3,4-dibromophenyl)propanoic acid, 2-amino-3-(3,4,5-triiodophenyl)propanoic acid, 2-amino-3-(2,3-dihydroxyphenyl)propanoic acid, 2-amino-3-(2,5-dihydroxyphenyl)propanoic acid, 2-amino-3-(2,6-dihydroxyphenyl)propanoic acid, 2-amino-3-(3-bromo-5-methoxyphenyl)propanoic acid, 2-amino-3-(2,5-dimethoxyphenyl)propanoic acid, 2-amino-3-(2,5-dimethoxy-4-methylphenyl)propanoic acid, 2-amino-3-(4-bromo-2,5-dimethoxyphenyl)propanoic acid, 2-amino-3-(3-carboxy-4-hydroxyphenyl)propanoic acid, 2-amino-3-(3-carboxy-4-aminophenyl)propanoic acid, 2-amino-3-(2-hydroxy-5-nitrophenyl)propanoic acid, 2-amino-3-(2-ethoxy-5-nitrophenyl)propanoic acid, 2-amino-3-(3,4,5-trimethoxyphenyl)propanoic acid, 2-amino-3-(4-azido-2-nitrophenyl)propanoic acid, 2-amino-3-(2-hydroxy-5-nitrophenyl)propanoic acid, 2-amino-3-(2, 4-bis-trimethylsilylphenyl)propanoic acid, 2-amino-3-(4-hydroxy-3,5-di-t-butylphenyl)propanoic acid, 2-amino-3-(4-hydroxy-3-benzylphenyl)propanoic acid, 2-amino-3-(4-hydroxy-3-fluorophenyl)propanoic acid, 2-amino-3-(4-hydroxy-2,3,5,6-tetrafluorophenyl)propanoic acid, 2-amino-3-(4-hydroxy-3,5-dichlorophenyl)propanoic acid, 2-amino-3-(4-hydroxy-3-iodophenyl)propanoic acid, 2-amino-3-(4-hydroxy-3,5-diiodophenyl)propanoic acid, 2-amino-3-(4-hydroxy-2-hydroxyphenyl)propanoic acid, 2-amino-3-(4-hydroxy-3-hydroxymethylphenyl) propanoic acid, 2-amino-3-(4-hydroxy-2hydroxy-6-methylphenyl)propanoic acid, 2-amino-3-(4-hydroxy-3-carboxyphenyl)propanoic acid, 2-amino-3-(4-hydroxy-3,5-dinitrophenyl)propanoic acid, substituted thyronines, 2-amino-3-(3,4-dihydroxy-2-chlorophenyl)propanoic acid, 2-amino-3-(3,4-dihydroxy-2-bromophenyl) propanoic acid, 2-amino-3-(3,4-dihydroxy-2-fluorophenyl)propanoic acid, 2-amino-3-(3,4-dihydroxy-2-nitrophenyl)propanoic acid, 2-amino-3-(3,4-dihydroxy-2-methylphenyl)propanoic acid, 2-amino-3-(3,4-dihydroxy-2-ethylphenyl)propanoic acid, 2-amino-3-(3, 4-dihydroxy-2-isopropylphenyl)propanoic acid, 2-amino-3-(2-t-butyl-4,5-dihydroxyphenyl)propanoic acid, 2-amino-3-(3-fluoro-4,5-dihydroxyphenyl)propanoic acid, 2-amino-3-(2-fluoro-4,5-dihydroxyphenyl) propanoic acid, 2-amino-3-(2,5,6-trifluoro-3,4-dihydroxyphenyl)propanoic acid, 2-amino-3-(2,6-dibromo-3,4-dihydroxyphenyl)propanoic acid, 2-amino-3-(5,6-dibromo-3,4-dihydroxyphenyl)propanoic acid, 2-amino-3-(2,4,5-trihydroxyphenyl)propanoic acid, 2-amino-3-(2,3,4-trihydroxyphenyl)propanoic acid, 2-amino-3-(3,4-dihydroxy-5-methoxyphenyl)propanoic acid, 2-amino-3-methyl-3-phenylpropanoic acid, 2-amino-3-ethyl-3-phenylpropanoic acid, 2-amino-3-isopropyl-3-phenylpropanoic acid, 2-amino-3-butyl-3-phenylpropanoic acid, 2-amino-3-benzyl-3-phenylpropanoic acid, 2-amino-3-phenylethyl-3-phenylpropanoic acid, 2-amino-3-(4-chorophenyl)-3-phenylpropanoic acid, 2-amino-3-(4-methoxyphenyl)-3-phenylpropanoic acid, 2-amino-3,3-diphenylpropanoic acid, 2-amino-3-[4-(N,N-diethylamino)phenyl]heptanoic acid, 2-amino-3-[4-(N,N-diethylamino)phenyl]pentanoic acid, 2-amino-3-(3,4-dimethoxyphenyl)pentanoic acid, 2-amino-3-(3,4-dihydroxyphenyl)pentanoic acid, 2-amino-3-methyl-3-phenylbutanoic acid, 2-amino-3-ethyl-3-phenylpentanoic acid, 2-amino-3-methyl-3-phenylpentanoic acid, 2-amino-3,3-diphenylbutanoic acid, 2-amino-3-fluoro-3-phenylpropanoic acid, 2-amino-3-methylene-3-phenylpropanoic acid, 2-amino-3-methylmercapto-3-phenylpropanoic acid, 2-amino-4-methylmercapto-4-phenylbutanoic acid, 2-amino-4-(3,4-dihydroxyphenyl)butanoic acid, 2-amino-5-(4-methoxyphenyl)pentanoic acid, 2-amino-4-phenylbutanoic acid, 2-amino-5-phenylpentanoic acid, 2-amino-3,3-dimethyl-5-phenylpentanoic acid, 2-amino-4-phenyl-3-butenoic acid, 2-amino-4-phenoxybutanoic acid, 2-amino-5-phenoxypentanoic acid, 2-amino-2-(indanyl)acetic acid, 2-amino-2-(1-tetralyl)acetic acid, 2-amino-4,4-diphenylbutanoic acid, 2-amino-2-(2-naphthyl)acetic acid, 2-amino-3-(1-naphthyl)propanoic acid, 2-amino-3-(1-naphthyl)pentanoic acid, 2-amino-3-(2-naphthyl)propanoic acid, 2-amino-3-(1-chloro-2-naphthyl)propanoic acid, 2-amino-3-(1-bromo-2-naphthyl)propanoic acid, 2-amino-3-(4-hydroxy-1-naphthyl)propanoic acid, 2-amino-3-(4-methoxy-1-naphthyl)propanoic acid, 2-amino-3-(4-hydroxy-2-chloro-1-naphthyl)propanoic acid, 2-amino-3-(2-chloro-4-methoxy-1-naphthyl)propanoic acid, 2-amino-2-(2-anthryl)acetic acid, 2-amino-3-(9-anthryl)propanoic acid, 2-amino-3-(2-fluorenyl)propanoic acid, 2-amino-3-(4-fluorenyl)propanoic acid, 2-amino-3-(carboranyl) propanoic acid, 3-methylproline, 4-methylproline, 5-methylproline, 4,4-dimethylproline, 4-fluoroproline, 4,4-difluoroproline, 4-bromoproline, 4-chloroproline, 4-aminoproline, 3,4-dehydroproline, 4-methylproline, 4-methyleneproline, 4-mercaptoproline, 4-(4-methoxybenzylmercapto)proline, 4-hydroxymethylproline, 3-hydroxyproline, 3-hydroxy-5-methylproline, 3,4-dihydroxyproline, 3-phenoxyproline, 2-aminoproline, 5-aminoproline, 3-carbamylalkylproline, 4-cyano-5-methyl-5-carboxyproline, 4,5-dicarboxyl-5-methylproline, 2-aziridinecarboxylic acid, 2-azetidinecarboxylic acid, 4-methyl-2-azetidinecarboxylic acid, pipecolic acid, 1,2,3,6-tetrahydropicolinic acid, 3,4-methyleneproline, 2.4-methyleneproline, 4-aminopipecolic acid, 5-hydroxypipecolic acid, 4,5-dihydroxypipecolic acid, 5,6-dihydroxy-2,3-dihydroindole-2-carboxylic acid, 1,2,3,4-tetrahydroquinoline-2-carboxylic acid, 6,7-dihydroxy-1,2,3,4-tetrahydroisoquinoline-3-carboxylic acid, 6-hydroxy-1-methyl-1,2,3,4-tetrahydroisoquinoline-3-carboxylic acid, 6,7-dihydroxy-1-methyl-1,2,3,4-tetrahydroisoquinoline-3-carboxylic acid, 1,3-oxazolidine-4-carboxylic acid, 1,2-oxazolidine-3-carboxylic acid, perhydro-1,4-thiazine-3-carboxylic acid, 2,2-dimethylthiazolidine-4-carboxylic acid, perhydro-1,3-thiazine-2-carboxylic acid, selenazolidine4-carboxylic acid, 2-phenylthiazolidine4-carboxylic acid, 2-(4-carboxylicyl)thiazolidine-4-carboxylic acid, 1,2,3,4,4a,9a-hexahydro-beta-carboline-3-carboxylic acid, 2,3,3a,8-atetrahydropyrrolo(2,3b)indole-2-carboxylic acid, 2-amino-3-(2-pyridyl)propanoic acid, 2-amino-3-(3-pyridyl)propanoic acid, 2-amino-3-(4-pyridyl)propanoic acid, 2-amino-3-(2-bromo-3-pyridyl)propanoic acid, 2-amino-3-(2-bromo-4-pyridyl)propanoic acid, 2-amino-3-(2-bromo-5-pyridyl)propanoic acid, 2-amino-3-(2-bromo-6-pyridyl)propanoic acid, 2-amino-3-(2-chloro-3-pyridyl)propanoic acid, 2-amino-3-(2-chloro-4-pyridyl)propanoic acid, 2-amino-3-(2-chloro-5-pyridyl)propanoic acid, 2-amino-3-(2-chloro-6-pyridyl)propanoic acid, 2-amino-3-(2-fluoro-3-pyridyl)propanoic acid, 2-amino-3-(2-fluoro-4-pyridyl)loropanoic acid, 2-amino-3-(2-fluoro-5-pyridyl)propanoic acid, 2-amino-3-(2-fluoro-6-pyridyl)proloanoic acid, 2-amino-3-(1,2-dihydro-2-oxo-3-pyridyl)propanoic acid, 2-amino-3-(1,2-dihydro-2-oxo-4-pyridyl)propanoic acid, 2-amino-3-(1,2-dihydro-2-oxo-5-pyridyl)propanoic acid, 2-amino-3-(1,2-dihydro-2-oxo-6-pyridyl)propanoic acid, 2-amino-3-(5-hydroxy-2-pyridyl)propanoic acid, 2-amino-3-(5-hydroxy-6-iodo-2-pyridyl)propanoic acid, 2-amino-3-(3-hydroxy-4-oxo-1,4dihydro-1-pyridyl)propanoic acid, N-(5-caroxyl-5-aminopentyl)pyridinium chloride, 1,2,5-trimethyl-4-(2-amino-2-carboxy-1-hydroxyethyl)pyridinium chloride, 2-amino-2-(5-chloro-2-pyridyl)acetic acid, N-(3-amino-3-carboxypropyl)pyridinium chloride, 2-amino-3-(2-pyrryl)propanoic acid, 2-amino-3-(1-pyrryl)propanoic acid, 2-amino-4-(l-pyrryl)butanoic acid, 2-amino-5-(1-pyrryl)pentanoic acid, 2-amino-3-(5-imidazolyl)-3-methylpropanoic acid, 2-amino-3-(5-imidazolyl)-3-ethylpropanoic acid, 2-amino-3-hexyl-3-(5-imidazolyl)propanoic acid, 2-amino-3-hydroxy-3-(5-imidazolyl)propanoic acid, 2-amino-3-(4-nitro-5-imidazolyl)proloanoic acid, 2-amino-3-(4-methyl-5-imidazolyl)propanoic acid, 2-amino-3-(2-methyl-5-imidazolyl)propanoic acid, 2-amino-3-(4-fluoro-5-imidazolyl)propanoic acid, 2-amino-3-(2-fluoro-5-imidazolyl)propanoic acid, 2-amino-3-(2-amino-5-imidazolyl)propanoic acid, 2-amino-3-(2-phenylaza-5-imidazolyl)propanoic acid, 2-amino-3-(1-methyl-2-nitro-5-imidazolyl)propanoic acid, 2-amino-3-(1-methyl4-nitro-5-imidazolyl)propanoic acid, 2-amino-3-(1-methyl-5-nitro-5-imidazolyl)propanoic acid, 2-amino-3-(2-mercapto-5-imidazolyl)propanoic acid, 2-amino-4-(5-imidazolyl)butanoic acid, 2-amino-3-(1-imidazolyl)propanoic acid, 2-amino-3-(2-imidazolyl)propanoic acid, 2-amino-(1-pyrazolyl)propanoic acid, 2-amino-(3-pyrazolyl)propanoic acid, 2-amino-(3,5-dialkyl-4-pyrazolyl)propanoic acid, 2-amino-3-(3-amino-1,2,4-triazol-1-yl)propanoic acid, 2-amino-3-(tetrazol-5-yl)propanoic acid, 2-amino-4-(5-tetrazolyl)butanoic acid, 2-amino-3-(6-methyl-3-indolyl)propanoic acid, 2-amino-3-(4-fluoro-3-indolyl)propanoic acid, 2-amino-3-(5-fluoro-3-indolyl)propanoic acid, 2-amino-3-(6-fluoro-3-indolyl)propanoic acid, 2-amino-3-(4,6,6,7-tetrafluoro-3-indolyl)propanoic acid, 2-amino-3-(-chloro-3-indolyl)propanoic acid, 2-amino-3-(6-chloro-3-indolyl)propanoic acid, 2-amino-3-(7-chloro-3-indolyl)propanoic acid, 2-amino-3-(6-bromo-3-indolyl)propanoic acid, 2-amino-3-(7-bromo-3-indolyl)propanoic acid, 2-amino-3-(2-hydroxy-3-indolyl)propanoic acid, 2-amino-3-(7-hydroxy-3-indolyl)propanoic acid, 2-amino-3-(7-hydroxy-3-indolyl)propanoic acid, 2-amino-3-(2-alkylmercapto-3-indolyl)propanoic acid, 2-amino-3-(7-amino-3-indolyl)propanoic acid, 2-amino-3-(4-nitro-3-indolyl)propanoic acid, 2-amino-3-(7-nitro-3-indolyl)propanoic acid, 2-amino-3-(4-carboxy-3-indolyl)propanoic acid, 2-amino-3-(3-indolyl)butanoic acid, 2-amino-3-(2,3-dihydro-3-indolyl)propanoic acid, 2-amino-3-(2,3-dihydro-2-oxo-3-indolyl)propanoic acid, 2-amino-3-alkylmercapto-3-(3-indolyl)propanoic acid, 2-amino-3-(4-aza-3-indolyl)propanoic acid, 2-amino-3-(7-aza-3-indolyl)propanoic acid, 2-amino-3-(7-aza-6-chloro-4-methyl-3-indolyl)propanoic acid, 2-amino-3-(2,3-dihydrobenzofuran-3-yl)propanoic acid, 2-amino-3-(3-methyl-5–7-dialkylbenzofuran-2-yl)propanoic acid, 2-amino-3-(benzothiophen-3-yl)propanoic acid, 2-amino-3-(5-hydroxybenzothiophen-3-yl)propanoic acid, 2-amino-3-eoenzoselenol-3yl)propanoic acid, 2-amino-3-quinolylpropanoic acid, 2-amino-3-(8-hydroxy-5-quinolyl)propanoic acid, 2-amino-2-(5,6,7,8-tetrahydroquinol-5-yl)acetic acid, 2-amino-3-(3-coumarinyl)propanoic acid, 2-amino-2-(benzisoxazol-3-yl)acetic acid, 2-amino-2-(5-methylbenzisoxazol-3-yl)acetic acid, 2-amino-2-(6-methylbenzisoxazol-3-yl)acetic acid, 2-amino-2-(7-methylbenzisoxazol-3-yl)acetic acid, 2-amino-2-(5-bromobenzisoxazol-3-yl)acetic acid, 2-amino-3-(benzimidazol-2-yl)propanoic acid, 2-amino-3-(5,6-dichlorobenzimidazol-2-yl)propanoic acid, 2-amino-3-(5,6-dimethylbenzimidazol-2-yl)propanoic acid, 2-amino-3-(4,5,6,7-hydrobenzirnidazol-2-yl)propanoic acid, 2-amino-2-(benzimidazol-5-yl)acetic acid, 2-amino-2-(1,3-dihydro-2,2-dioxoisobenzothiophen-5-yl)acetic acid, 2-amino-2-(1,3-dihydro-2,2-dioxo-2,1,3-benzothiadiazol-5-yl)acetic acid, 2-amino-2-(2-oxobenzimidazol-5-yl)acetic acid, 2-amino-3-(4-hydroxybenzothiazol-6-yl)propanoic acid, 2-amino-3-(benzoxazol-2-yl)propanoic acid, 2-amino-3-(benzothiazol-2-yl)propanoic acid, 2-amino-3-(9-adeninyl)propanoic acid, 2-amino-2-(6-chloro-9-purinyl)acetic acid, 2-amino-2-(6-amino-9-purinyl)acetic acid, 2-amino-3-(6-purinyl)propanoic acid, 2-amino-3-(8-theobrominyl)propanoic acid, 2-amino-2-(1-uracilyl)acetic acid, 2-amino-2-(1-cytosinyl)acetic acid, 2-amino-3-(1-uracilyl)propanoic acid, 2-amino-3-(1-cytosinyl)propanoic acid, 2-amino-4-(1-pyrimidinyl)butanoic acid, 2-amino-4-(4-amino-1-pyrimidinyl)butanoic acid, 2-amino-4-(4-hydroxy-1-pyrimidinyl)butanoic acid, 2-amino-5-(1-pyrimidinyl)pentanoic acid, 2-amino-5-(4-amino-1-pyrimidinyl)pentanoic acid, 2-amino-5-(4-hydroxy-1-pyrimidinyl)pentanoic acid, 2-amino-3-(5-pyrimidinyl)propanoic acid, 2-amino-3-(6-uracilyl) propanoic acid, 2-amino-3-(2-pyrimidinyl)propanoic acid, 2-amino-3-(6-amino-4-chloro-2-pyrimidinyl) propanoic acid, 2-amino-3-(4-hydroxy-2-pyrimidinyl) propanoic acid, 2-amino-3-(2-amino-4-pyrimidinyl) propanoic acid, 2-amino-3-(4,5-dihydroxypyrimidin-2-yl)propanoic acid, 2-amino-3-(2-thiouracil-6-yl) propanoic acid, 2-amino-2-(5-alkyl-2-tetrahydrofuryl) acetic acid, 2-amino-2-(5-methyl-2,5-dihydro-2-furyl) acetic acid, 2-amino-2-(5-alkyl-2-furyl)acetic acid, 2-amino-2-(2-furyl)acetic acid, 2-amino-2-(3-hydroxy-5-methyl-4-isoxazolyl)acetic acid, 2-amino-3-(4-bromo-3-hydroxy-5-isoxazolyl)propanoic acid, 2-amino-3-(4-methyl-3-hydroxy-5-isoxazolyl)propanoic acid, 2-amino-3-(3-hydroxy-5-isoxazolyl)propanoic acid, 2-amino-2-(3-chloro-D2-isoxazolin-5-yl)acetic acid, 2-amino-2-(3-oxo-5-isoxazolidinyl)acetic acid, 2-amino-3-(3,5-dioxo-1,2,4-oxadiazolin-2-yl)propanoic acid, 2-amino-3-(3-phenyl-5-isoxazolyl)propanoic acid, 2-amino-3-[3-(4-hydroxyphenyl)-1,2,4-oxadiazol-5-yl]propanoic acid, 2-amino-3-(2-thienyl)propanoic acid, 2-amino-2-(2-furyl)acetic acid, 2-amino-2-(2-thienyl)acetic acid, 2-amino-2-(2-thiazolyl)acetic acid, 2-amino-3-(2-thiazolyl)propanoic acid, 2-amino-4-(4-carboxy-2-thiazolyl)butanoic acid, 2-amino-3-(4-thiazolyl) propanoic acid, 2-amino-3-(2-selenolyl)propanoic acid, 2-amino-3-(2-amino-4-selenolyl)propanoic acid, and 2-amino-3-(beta-ribofuranosyl)propanoic acid.

"Amino acids residue" also refers to various amino acids where sidechain functional groups are coupled with appropriate protecting groups known to those skilled in the art. "The Peptides", Vol 3, 3–88 (1981)discloses numerous suitable protecting groups and is incorporated herein by reference for that purpose. Examples of amino acids where sidechain functional groups are coupled with appropriate protecting groups include, but are not limited to, Asp(OMe), Glu(OMe), Hyp(OMe), Asp(O$^t$Bu), Glu(O$^t$Bu), Hyp(O$^t$Bu), Thr(O$^t$Bu), Asp(OBzl), Glu(OBzl), Hyp(OBzl), and Thr (OBzl).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Therapeutically effective amount" is intended to include an amount of a compound of the present invention or an amount of the combination of compounds claimed effective to inhibit HCV infection or treat the symptoms of HCV infection in a host. The combination of compounds is preferably a synergistic combination. Synergy, as described for example by Chou and Talalay, *Adv. Enzyme Regul.* 1984, 22, 27–55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of α-hydroxyesters and α-hydroxyamides of formula 5 are prepared by the method outlined in Scheme 1. Amino acid 1, wherein Z″ is an amino protecting group, is treated with (cyanomethylene)tripheneylphosphorane to give cyano keto phosphorane 2. Ozonolysis of 2 provides α-ketoester 3a or α-ketoamide 3b, which under reduction conditions yields α-hydroxyester 4a or α-hydroxyamide 4b. Hydrogenation of 4 in the presence of 10% Pd/C affords α-hydroxyester 5a or α-hydroxyamide 5b. (Wasserman, H. H. et al, *J. Org. Chem.* 1994, 59, 4364).

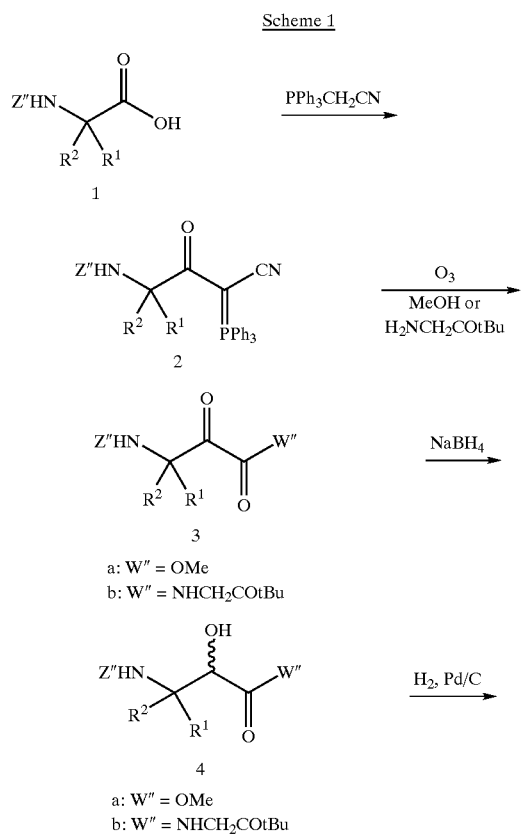

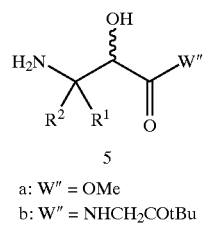

A series of α-hydroxyl β-amino esters and α-hydroxyl β-amino amides of formula 8 are prepared by the method outlined in Scheme 2. Many of the α,β-unsaturated esters or amides 6 are commercially available or may be easily prepared from commercially available materials. Sharpless asymmetric aminohydroxylation of α,β-unsaturated ester or amide 6 gives α-hydroxyl β-amino ester or α-hydroxyl β-amino amide 7. Reductive removal of the carbobenzyloxy (CBZ) group provides 8. (Sharpless, K. B.; et al, *Angew. Chem. Int. Ed. Engl.* 1996, 35, 451. Sharpless, K. B. et al, *Angew. Chem. Int. Ed. Engl.* 1996, 35, 2813.)

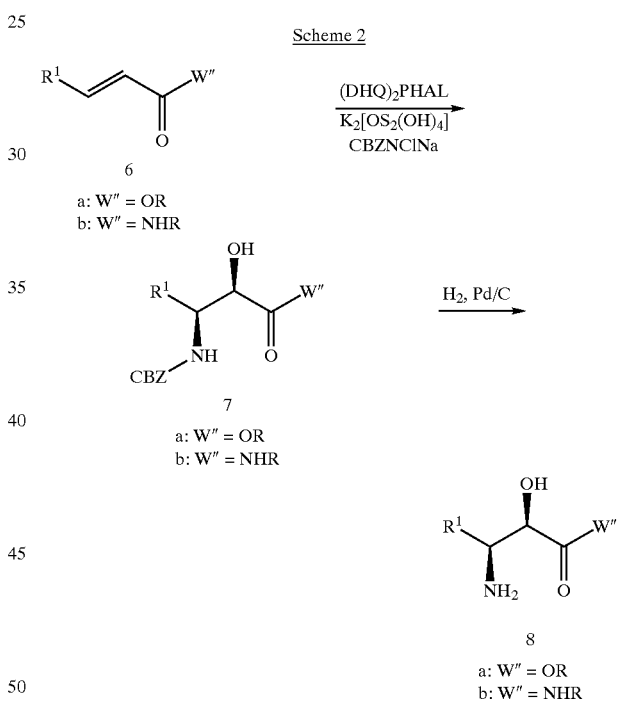

A series of α-hydroxyl β-amino esters of formula 15 are prepared by the method outlined in Scheme 3. Treatment of phosphonoglycine trimethyl ester 9, wherein Z″ is an amino protecting group such as CBZ, with difluoroacetaldehyde hemiacetal 10 in the present of KOtBu yields α,β-unsaturated ester 11. Hydrogenation of 11 in the present of a chiral Rh catalyst, such as Duphos, selectively reduces the double bond and affords 12 in high enantiomeric excess. DIBAL reduction of methyl ester 12 gives corresponding aldehyde 13, which under the treatment of lithium tris (methylthhio)methane to provide α-hydroxyl compound 14. Finally, α-hydroxyl β-amino ester of formula 15 is obtained when 14 is treated with Hg$^{2+}$. (Kaneko, S. K.; et al, *J. Org. Chem.* 1993, 58, 2302.)

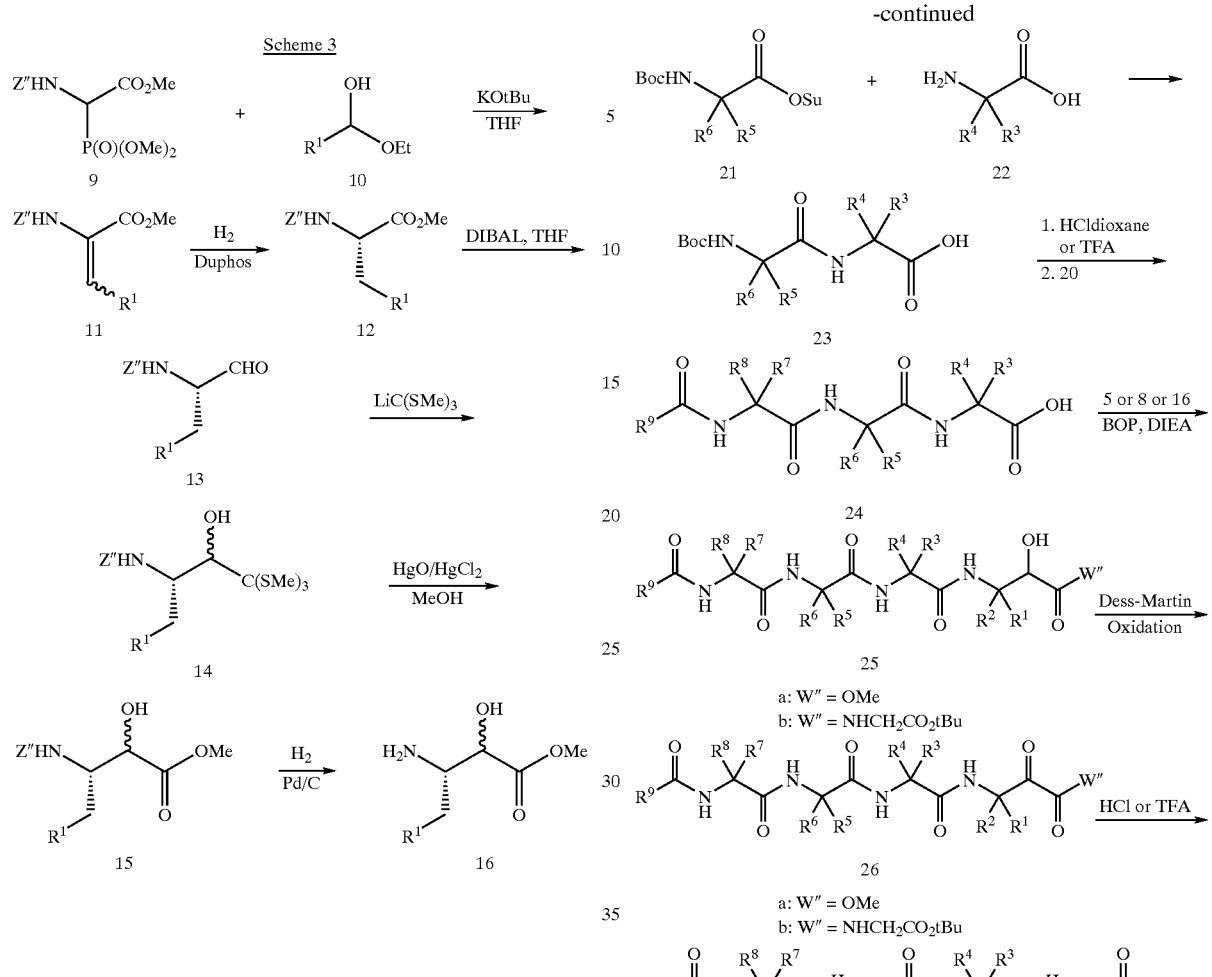

A series of α-ketoamides or acids of formula 27 are prepared by the method outlined in Scheme 4. Amino acid 18 is coupled with 17 under regular coupling conditions to afford 19, which is then converted to its succinimide 20. Compound 20 is coupled with dipeptide 23, which is prepared by the same method, to yield tripeptide 24. Compound 24 is reacted with the α-hydroxyl β-amino ester or amide under standard coupling conditions to give α-hydroxyl ester or amide 25. Dess-Martin oxidation converts 25 to α-keto ester or amide 26. The methyl ester 26 is either saponified to provide α-keto acid 27a, or deprotected in TFA to afford α-keto amide 27b. (Angelastro, M. R. *J. Med. Chem.* 1990, 33, 13.)

A series of α-keto amides or acids of formula 34 are prepared by the method outlined in Scheme 5. Coupling of acid 28 with proline derivative 29 in the present of BOP and DIEA yields compound 30. Deprotection of BOC group in 30 followed by the coupling with the same intermediate 19 provides compound 31. Application of similar chemistry to that described in Scheme 4 leads to the synthesis of α-keto amides or acids of formula 34.

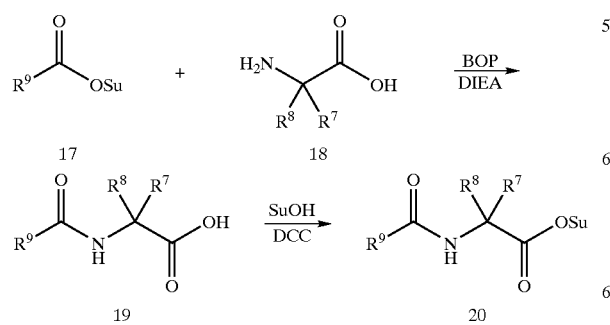

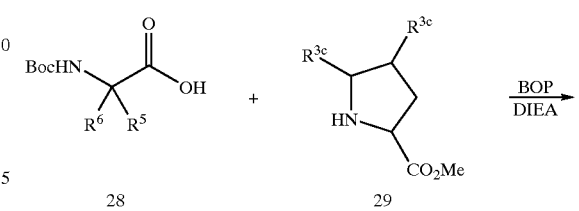

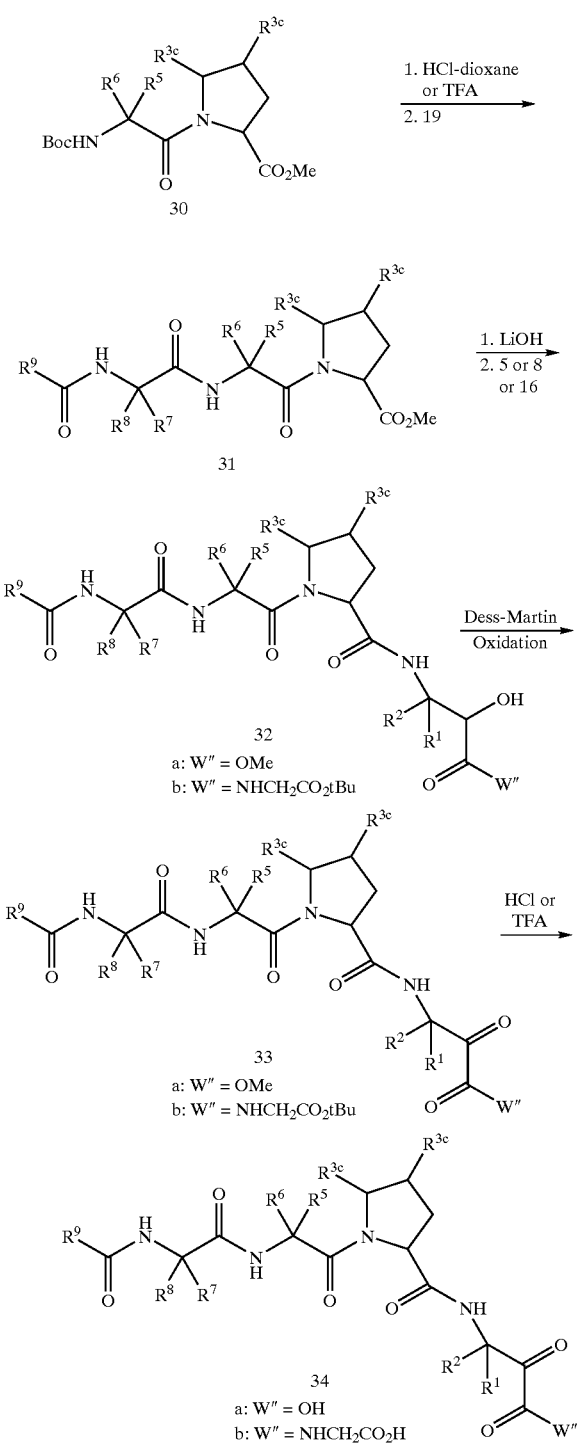

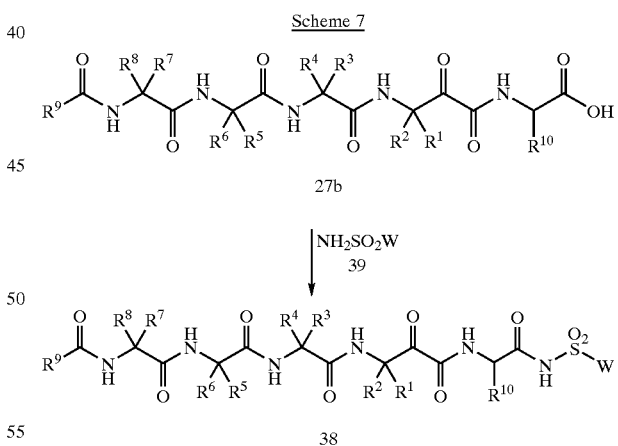

A series of α-ketoamides of formula 36 are prepared by the method outlined in Scheme 6. From the same intermediate 25a, saponification affords the corresponding acid, which reacts with amines of formula 37 to give α-hydroxyamide 35. Dess-Martin oxidation of 35 provides α-ketoamide 36.

A series of α-ketoamides of formula 38 are prepared by the method outlined in Scheme 7. Treatment of intermediate 27b with sulfonamide of type 39 in the presence of a coupling agent such as EDCI and DMAP provides α-ketoamide 38. (Andery, R. H.; *J. Org. Chem.* 1986, 987).

A series of α-ketoamides of formula 44 are prepared by the method outlined in Scheme 8. Protection of the amino group in 39 gives sulfonic acid 40. Treatment of compound 40 with $PCl_3$ followed by ammonia yields sulfonamide 41. Acylation of 41 with an acid chloride of type 45 affords acyl sulfonamide 42. Deprotection of the N terminal 42 with hydrazine gives amine 43. Coupling of amine 43 with α-ketoacid 27a provides α-ketoamide 44.

Scheme 8

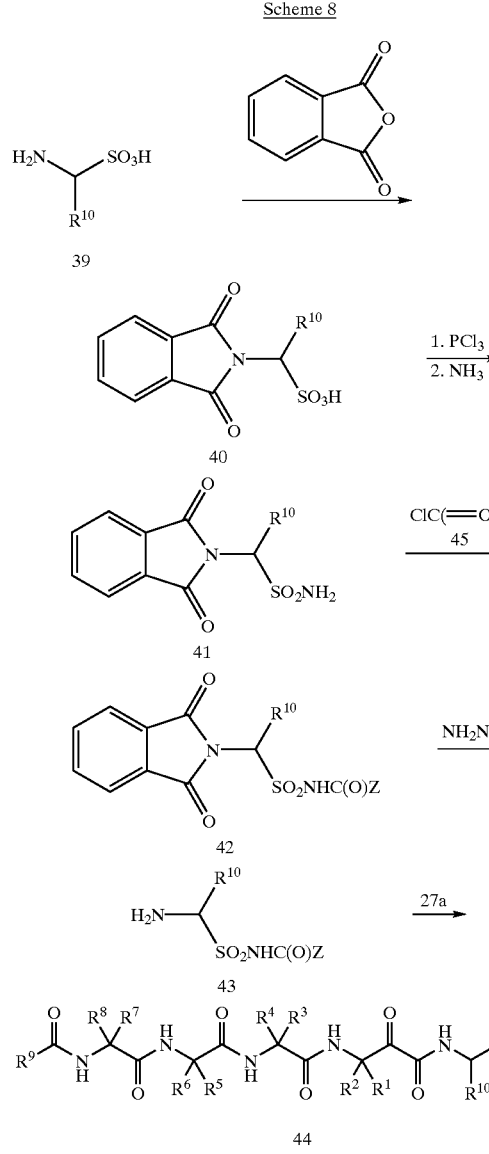

A series of α-ketoamides of formula 46 are prepared by the method outlined in Scheme 9. Treatment of intermediate 27b with amide of type 45 in the present of DCC and DMAP provides α-ketoamide 46. (Almeida, P. S. et al. *Tetrahedron Lett.* 1991, 23, 2671).

Scheme 9

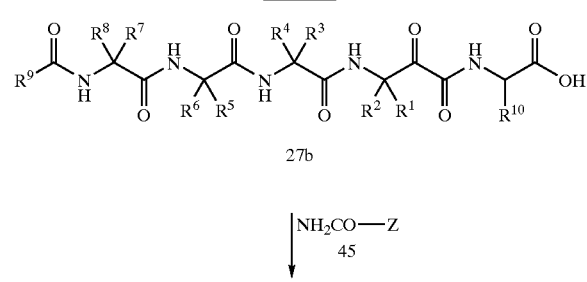

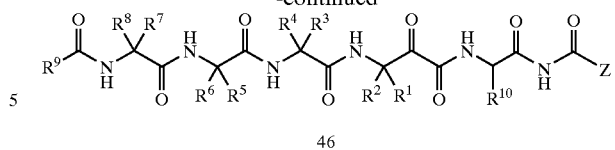

A series of α-ketoamides of formula 50 are prepared by a similar method to the preparation of compound 27 as outlined in Scheme 10.

Many of the CBZ protected amino acids and amino acid methyl esters are commercially available or may be prepared from commercial amino acid derivatives by simple protecting group manipulations. Others may be synthesized in racemic form using the Strecker synthesis or amidomalonate synthesis. In addition, the Myers pseudoephedrine glycinamide alkylation method (Myers, A. G.; Gleason, J. L.; Yoon, T; Kung, D. W. *J. Am. Chem. Soc.* 1997, 119, 656–673) and the Evans electrophilic azidation (Evans, D. A.; Britton, T. C.; Ellman, J. A.; Dorow, R. L. *J. Am. Chem. Soc.* 1990, 112, 4011) may be used to prepare unnatural amino acids in enantiomerically pure form.

Scheme 10

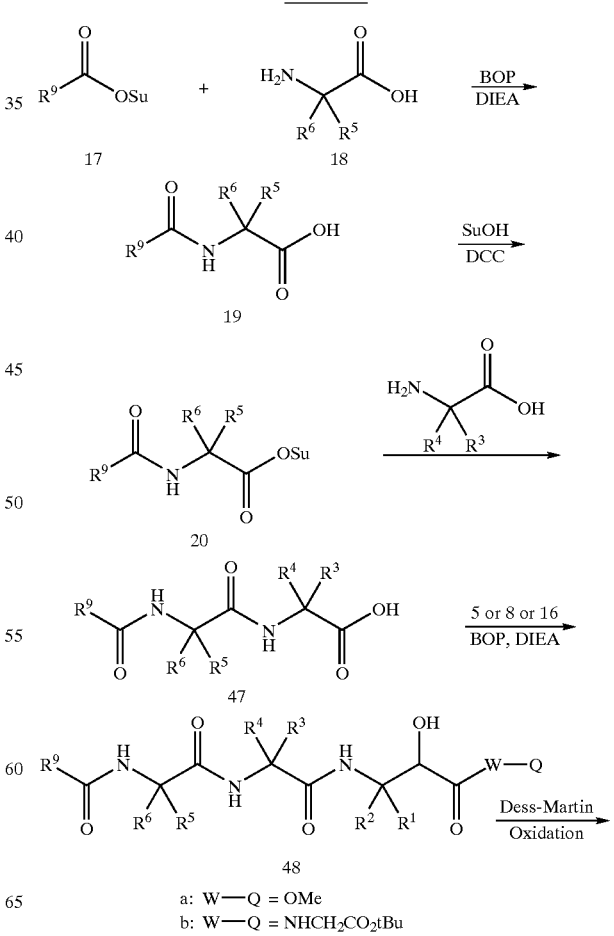

a: W—Q = OMe
b: W—Q = NHCH$_2$CO$_2$tBu

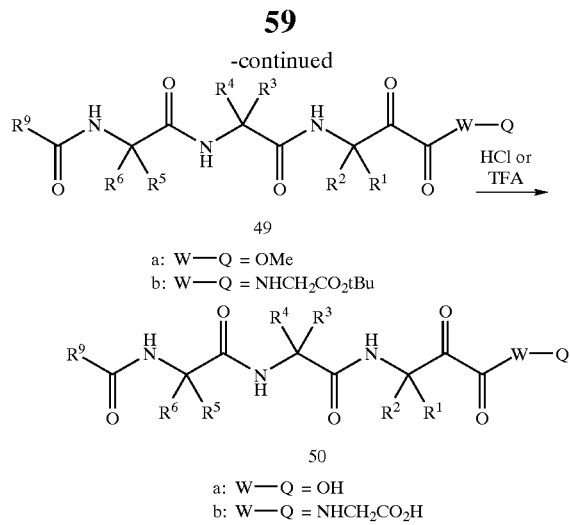

a: W—Q = OMe
b: W—Q = NHCH₂CO₂tBu a: W—Q = OH
b: W—Q = NHCH₂CO₂H

When required, separation of the racemic material can be achieved by HPLC using a chiral column or by a resolution using a resolving agent such as camphonic chloride as in Steven D. Young, et al, *Antimicrobial Agents and Chemotheraphy* 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the examples are defined as follows: "1×" n for once, "2×" for twice, "3×" for thrice, "°C." for degrees Celsius, "rt" for room temperature, "eq" for equivalent or equivalents, "g" for gram or grams, "mg" for milligram or milligrams, "mL" for milliliter or milliliters, "M" for molar, "mmol" for millimole or millimoles, "min" for minute or minutes, "h" for hour or hours, "MS" for mass spectrometry, "NMR" for nuclear magnetic resonance spectroscopy, "¹H" for proton, "HPLCN" for high pressure liquid chromatography, "tlc" for thin layer chromatography, "v/v" for volume to volume ratio, "atm" for atmosphere, "α", "β", "R", and "S" are stereochemical designations familiar to one skilled in the art.

Abbreviations used in the specification are defined as follows:

"BOP" is benzotriazol-1-yloxy-tris(dimethylamino)-phosphonium hexafluorophosphate;
"Bzl" or "Bn" is benzyl;
"CBZ" is carbobenzyloxy;
"COD" is cyclooctadiene;
"DCC" is 1,3-dicyclohexylcarbodiimide;
"(DHQ)₂PHAL" is hydroquinine 1,4-phthalazinediyl diether;
"DIBAL" is diisobutylaluminum hydride;
"DIEA" is Diisopropylethylamine;
"DMAP" is 4-dimethylamino pyridine;
"DMF" is dimethylformamide;
"DMSO" is dimethylsyulfoxide;
"Duphos" is (+)-1,2-bis(2S,5S)-2,5-diethylphospholano)-benzene(cyclooctadiene)rhodium(I) trifluoromethane-sulfonate "EtOAc" is ethylacetate;
"EDCI" is 1-(3-dimethylaminopropyl)-3-ethylcarbodiimide hydrochloride;
"Pz" is pyrazinyl;
"SuOH" is N-hydroxysuccinimide; and
"TFA" is trifluoroacetic acid.

Example A1

N-(2-pyrazinylcarbonyl)-L-leucyl-L-isoleucyl-3-cyclohexyl-L-alanyl-2-oxo-(3 S)-3-amino pentanoylglycine Step (A1a): At 0° C., DIEA (12.1 Ml, 69.5 mmol) was added to the suspension of Ph₃PCH₂CNCl in CH₂Cl₂. The suspension turned to clear. The aminobutyric acid (15.0 g, 63.2 mmol) was added followed by addition of EDCI (12.7 g, 66.4 mmol) and DMAP (0.77 g, 6.32 mmol). The resulted mixture was stirred at 0° C. for 2 h and at rt over night. Most of the solvent was evaporated and the residue was chromatographed on silica gel (50–60% EtOAc:Hexane). The product (Scheme 1, 2) was obtained as a white solid 22.7 g in 69% yield. MS found (M+1)⁺ 521.3

Step (A1b): The ylide obtained from Step(A1a) (10 g, 19.2 mmol) was dissolved in CH₂Cl₂ (200 mL) and the mixture was cooled to −78° C. To this mixture at −78° C. was purged O₃ until the color changed to blue. Excess O₃ was removed by purging N₂ into the mixture. The solution of Gly-OtBu hydrochloride (3.54 g, 21.1 mmol), pretreated with DIEA and precooled) in CH₂Cl₂ was added at −78° C. to the above reaction mixture and stirred at −78° C. for 30 min, then warmed to rt. Solvent was evaporated and the residue was chromatographed on silica gel (20–50% EtOAc:hexane). The α-ketoamide (Scheme 1, 3) was obtained in 58% yield as an oil (4.25 g). MS found (M+Na)⁺ 401.1. Similarly, the reaction mixture can be quenched with methanol instead of Gly-OtBu to provide the corresponding α-ketoester (Scheme 1, 3a).

Step (A1c): To a solution of ketoamide obtained from Step (A1b) (0.23 g, 0.61 mmol) in THF (10 mL) at 0° C. was added sodium borohydride (42 mg, 1.22 mmol) in portions. After stirring at 0° C. for 30 min, the reaction mixture was quenched with acetone. Most of the solvent was evaporated and the residue was dissolved in EtOAc, washed with H₂O and brine. Chromatography on silica gel (40% EtOAc in hexane) yielded 124 mg α-hydroxyamide (Scheme 1, 4) as a colorless oil (53%). MS found (M+1)⁺ 381.2.

Step (A1d): The α-hydroxyamide obtained from Step (A1c) (124 mg, 0.326 mmol) was dissolved in MeOH (50 mL) and Pd/C 10 mg) was added. The mixture was hydrogenated under 1 atm. for 40 min. The reaction mixture was filtered and concentrated. The amine (Scheme 1, 5) was obtained in 99% yield as a white solid 82 mg. MS found (M+1)⁺ 247.3. Similarly, the α-ketoester from (A1b) was converted to α-hydroxyester (Scheme 1, 5a) via step (A1c).

Step (A1e): DCC (3.99 g, 19.3 mmol, 1.2 eq) was added to a solution of 2-pyrazine carboxylic acid (2.0 g, 16.1 mmol) and N-hydroxysuccinimide (1.95 g, 16.9 mmol, 1.05eq) in 100 mL THF at 0° C. The mixture was stirred at rt over night. The reaction mixture was filtered, concentrated and dried. The product was obtained in 91% yield as a solid (Scheme 4, 17).

Step (A1f): At 0° C. under N₂, DIEA (13.3 mL, 76.13 mmol) was added to a solution of material from Step (A1e) (10 g, 45.2 mmol) and leucine (5.93 g, 45.3 mmol) in 120 mL DMF. After addition, the resulted mixture was stirred at rt over night. The mixture was diluted with 200 mL of EtOAc, washed with 1N HCl (2×30 mL), H$_2$O (2×50 mL) and brine, and dried over MgSO$_4$. The solvent was removed and dried on vacuum to provide a white solid as pure product (95%) (Scheme 4, 19). MS found (M−1)$^-$ 219.

Step (A1g): Following a procedure analogous to Step (A1e), the material from Step (A1f) (1.0 g, 4.5 mmol) was treated with N-hydroxysuccinimide (530 mg, 4.5 mmol), providing the desired product as a white solid (1.28 g, 90%) (Scheme 4, 20).

Step (A1h): Following a procedure analogous to Step (A1f), the succinimide ester of N-Boc isoleucine (10 g, 30.45 mmol) was treated with cyclohexylalanine (6.32 g, 30.45 mmol) in the presence of DIEA in DMF, providing the desired product (Scheme 4, 23) as a white solid (95%). MS found (M+1)$^+$ 385.3.

Step (A1i): The material from Step (A1h) (1.0 g, 2.6 mmol) was treated with 4M HCl in dioxane for 2 h at rt. Solvent was evaporated and the residue was dried. Following a procedure analogous to Step (A1f), the material from above was treated with the material from Step (A1g) (0.83 g, 2.6 mmol) in the presence of DIEA in DMF, providing the desired product (Scheme 4, 24) as a white solid (1.16 g, 89%). MS found (M+1)$^+$ 504.3.

Step (A1j): To a solution of the above material from Step (A1i) (1 g, 1.99 mmol) in 100 mL of DMF at 0° C. was added BOP (1.3 g, 2.98 mmol) and DIEA (0.52 mL, 2.98 mmol). The mixture was stirred at this temp. for 20 min. Then a solution of the material from Step (A1d) (490 mg, 1.99 mmol) in 10 mL of DMF was added to the above mixture followed by addition of another portion of DIEA (0.52 mL, 1.99 mmol). The resulting mixture was stirred at 0° C. for 1 h and rt overnight. The reaction mixture was diluted with EtOAc (400 mL), washed with 1N HCl, saturated NaHCO$_3$, H$_2$O, brine, dried and concentrated. Chromatography on silica gel (70% EtOAc in hexane) provided desired product (1.22 g, 84%) as a white solid (Scheme 4, 25b). MS found (M+1)$^+$ 732.4.

Step (A1k): To a mixture of the above material from Step (A1j) (200 mg, 0.27 mmol) and molecular sieves in 6 mL of CH$_2$Cl$_2$ was added Dess-Martin reagent (172 mg, 0.41 mmol). The resulting mixture was stirred at rt for 2 h. Then the mixture was filtered and the residue was chromatographed on silica gel (5% MeOH in CHCl$_3$) to provide the desired ketoamide (Scheme 4, 26b) as a white solid (169 mg, 86%). MS found (M+1)$^+$ 730.3.

Step (A1l): A solution of the above material from Step (A1k) (300 mg, 0.41 mmol) in CH$_2$Cl$_2$ was treated with TFA (20 mL, 1:1) and the mixture was stirred at rt for 2 h. After evaporation of the solvent, the residue was dried in vacuum and the title ketoamide (Scheme 4, 27b), Example 1A, was obtained (273 mg, 99%) as a light yellow solid. MS found (M+1)$^+$ 674.4.

Example A2

(3S)-2-oxo-3-{[N-(2-pyrazinylcarbonyl)-L-leucyl-L-isoleucyl-3-cyclohexyl-L-alanyl]amino}-N-(2H-tetrazol-5-ylmethyl) pentanamide Step (A2a): The ylide obtained from Step (A1a) (10 g, 19.2 mmol) was dissolved in CH$_2$Cl$_2$ (200 mL) and the mixture was cooled to −78° C. To this mixture was purged O$_3$ at this temp. until the color of the mixture changed to blue. Excess O$_3$ was removed by purging N$_2$ into the mixture. Methanol was added at −78° C. to the above reaction mixture. The resulting mixture was stirred at −78° C. for 30 min and warmed to rt. Solvent was evaporated and the residue was chromatographed on silica gel (20–50% EtOAc:hexane). The α-ketoester (Scheme 1, 3a) was obtained in 87% yield as a white solid. MS found (M+Na)$^+$ 280.4.

Step (A2b): Following a procedure analogous to Step (A1c), the ketoester from Step (A2a) (1 g, 3.6 mmol) was reduced with NaBH$_4$ to the desired α-hydroxyester (Scheme 1, 4a) as a white solid (0.86 g, 86%). MS found (M+1)$^+$ 282.3.

Step (A2c): Following a procedure analogous to Step (A1d), the α-hydroxyester (0.7 g, 2.5 mmol) from Step (A2b) above was hydrogenated in the present of 10% Pd/C to give the desired amine (Scheme 1, 5a) as a white solid (3.6 g, >95%). MS found (M+1)$^+$ 148.3.

Step (A2d): Following a procedure analogous to Step (A1j), the material from Step (A2c) above (0.5 g, 3.4 mmol) was coupled with the material from Step (A1i) (1.7 g, 3.4 mmol) to provide the desired the α-hydroxyester (Scheme 4, 25a) as a white solid (1.4 g, 67%). MS found (M+1)$^+$ 633.3.

Step (A2e): To a solution of the above material from Step (A2d) (500 mg, 0.79 mmol) in 8 mL THF at 0° C. was added 8 mL of 1N LiOH solution. After stirring at this temp for 3 h, the mixture was acidified with 1N HCl to pH 5. Solvent was evaporated and the residue was extrated with EtOAc (3×50 mL). The combined organic portion was washed with water, brine and dried. Removal of solvent yielded the acid product (463 mg, 95%) as white solid. MS found (M+1)$^+$ 619.2, (M−1)$^-$ 617.1.

Step (A2f): Aminomethyltetrazole (75 mg, 0.76 mmol) was suspended in 6 mL mixed solvent of DMF/DMSO (1:1). To this mixture was added DIEA (0.3 mL), material from Step (A2e) above (50 mg, 0.081 mmol) and BOP reagent (200 mg). The resulting mixture was stirred at rt for 3 h. Then the mixture was HPLC purified (grandient starting from 30% water in acetonitrile) to give the desired product as a white solid (46 mg, 82%). MS found (M+1)$^+$ 701.4.

Step (A2g): The material from Step (A2f) above (46 mg, 0.066 mmol) was dissolved in 5.0 mL methylenechloride. Dess-Martin reagent (100 mg) was added. The mixture was stirred at rt for 1.5 h. Then the reaction mixture was filtered and solvent was removed. HPLC purification (grandient starting from 30% water in acetonitrile) gave Example A2, a white solid, as pure product (40 mg, 89%). MS found (M+1)$^+$ 698.4.

Example A3

2-oxo-3-[[N-(2-pyrazinylcarbonyl)-L-leucyl-L-isoleucyl-3-cyclohexylalanyl]amino]-N-(sulfomethyl)pentanamide Step (A3a): Following a procedure analogous to Step (A2f), the material from Step (A2e) (50 mg, 0.081 mmol) was coupled with aminomethanesulfonic acid (18 mg, 0.16 mmol), providing the title product as a light-yellow solid (44 mg, 76%). MS found (M+1)$^+$ 712.3.

Step (A3b): Following a procedure analogous to Step (A2g), the above material from Step (3a) (44 mg, 0.062 mmol) was oxidized with Dess-Martin reagent to give the title α-ketoamide (30 mg, 68%). MS found (M+1)$^+$ 710.3.

Example A4

N-(2-pyrazinylcarbonyl)-L-leucyl-L-isoleucyl-3-cyclohexylalanyl-2-oxo-3-aminopentanoyl-N-[(2-nitrophenyl)sulfonyl]glycinamide Step (A4a): To the mixture of the material from Step (A1l) (Scheme 4, 27b) (34 mg, 0.05 mmol) in CH$_2$Cl$_2$ (5 mL)

at 0° C. were added a solution of (2-nitrophenyl)sulfonamide (15 mg, 0.075 mmol) and DMAP (6 mg, 0.05 mmol) in CH$_2$Cl$_2$, followed by addition of EDCI (14.3 mg, 0.075 mmol). The resulting mixture was stirred at rt for 40 min. The reaction mixture was diluted with EtOAc, washed with H$_2$O, brine, dried and concentrated. HPLC purification gave the title product as a white solid. MS found (M+1)$^+$ 858.3.

Example A5

N-(2-pyrazinylcarbonyl)-L-leucyl-L-isoleucyl-3-cyclohexylalanyl-2-oxo-3-aminopentanoyl-N-(methylsulfonyl)glycinamide Step (A5a) Following a procedure analogous to Step (A4a), compound 27b (Scheme 4) was coupled with methylsulfonamide to provide the title compound. MS found (M+1)$^+$ 751.4.

Example A6

N-(2-pyrazinylcarbonyl)-L-leucyl-L-isoleucyl-3-cyclohexylalanyl-2-oxo-3-aminopentanoyl-N-[(phenylmethyl)sulfonyl]glycinamide Step (A6a) Following a procedure analogous to Step (A4a), compound 27b (Scheme 4) was coupled with phenylmethyl-sulfonamide to provide the title compound. MS found (M+1)$^+$ 825.4.

Example A7

N-(2-pyrazinylcarbonyl)-L-leucyl-L-isoleucyl-3-cyclohexylalanyl-2-oxo-3-aminopentanoyl-N-(phenylsulfonyl)glycinamide Step (A7a) Following a procedure analogous to Step (A4a), compound 27b (Scheme 4) was coupled with phenylmethyl-sulfonamide to provide the title compound. MS found (M+1)$^+$ 813.4.

Example A8

N-(2-pyrazinylcarbonyl)-L-leucyl-L-isoleucyl-3-cyclohexylalanyl-2-oxo-3-aminopentanoyl-N-[(trifluoromethyl)sulfonyl]glycinamide Step (A8a) Following a procedure analogous to Step (A4a), compound 27b (Scheme 4) was coupled with trifluoromethylsulfonamide to provide the title compound. MS found (M+1)$^+$ 805.4.

Example A9

N-(2-pyrazinylcarbonyl)-L-leucyl-L-isoleucyl-3-cyclohexylalanyl-2-oxo-3-aminopentanoyl-N-[(2-nitrophenyl)sulfonyl]glycinamide Step (A9a) Following a procedure analogous to Step (A4a), compound 27b (Scheme 4) was coupled with (2-nitrophenyl)sulfonamide to provide the title compound. MS found (M+1)$^+$ 858.1.

Example A10

N-(2-pyrazinylcarbonyl)-L-leucyl-L-isoleucyl-3-cyclohexylalanyl-2-oxo-3-aminopentanoyl-N-[(4-nitrophenyl)sulfonyl]glycinamide Step (A10a) Following a procedure analogous to Step (A4a), compound 27b (Scheme 4) was coupled with (4-nitrophenyl)sulfonamide to provide the title compound. MS found (M+1)$^+$ 858.3.

Example A11

N-(2-pyrazinylcarbonyl)-L-leucyl-L-isoleucyl-3-cyclohexylalanyl-2-oxo-3-aminopentanoyl-N-[(4-fluorophenyl)sulfonyl]glycinamide Step (A11a) Following a procedure analogous to Step (A4a), compound 27b (Scheme 4) was coupled with (4-fluorophenyl)sulfonamide to provide the title compound. MS found (M+1)$^+$ 831.4.

Example A12

N-(2-pyrazinylcarbonyl)-L-leucyl-L-isoleucyl-3-cyclohexyl-L-alanyl-2-oxo-(3 S)-3-amino pentanoyl-N-[(3-fluorophenyl)sulfonyl]glycinamide Step (A12a) Following a procedure analogous to Step (A4a), compound 27b (Scheme 4) was coupled with (3-fluorophenyl)sulfonamide to provide the title compound. MS found (M+1)$^+$ 831.4.

Example A13

N-(2-pyrazinylcarbonyl)-L-leucyl-L-isoleucyl-3-cyclohexylalanyl-2-oxo-3-aminopentanoyl-N-[(2-fluorophenyl) sulfonyl]glycinamide Step (A13a) Following a procedure analogous to Step (A4a), compound 27b (Scheme 4) was coupled with (2-fluorophenyl)sulfonamide to provide the title compound. MS found (M+1)$^+$ 831.5.

Example A14

N-(2-pyrazinylcarbonyl)-L-leucyl-L-isoleucyl-3-cyclohexylalanyl-2-oxo-3-aminopentanoyl-N-[(4-chlorophenyl) sulfonyl]glycinamide Step (A14a) Following a procedure analogous to Step (A4a), compound 27b (Scheme 4) was coupled with (4-chlorophenyl)sulfonamide to provide the title compound. MS found (M+1)$^+$ 848.3.

Example A15

N-(2-pyrazinylcarbonyl)-L-leucyl-L-isoleucyl-3-cyclohexylalanyl-2-oxo-3-aminopentano yl-N-[(3-chlorophenyl) sulfonyl]glycinamide Step (A15a) Following a procedure analogous to Step (A4a), compound 27b (Scheme 4) was coupled with (3-chlorophenyl)sulfonamide to provide the title compound. MS found (M+1)$^+$ 848.4.

Example A16

N-(2-pyrazinylcarbonyl)-L-leucyl-L-isoleucyl-3-cyclohexylalanyl-2-oxo-3-aminopentanoyl-N-[[4-(thionitroso)phenyl]sulfonyl]glycinamide Step (A16a) Following a procedure analogous to Step (A4a), compound 27b (Scheme 4) was coupled with 4-(thionitroso)phenylsulfonamide to provide the title compound. MS found (M+1)$^+$ 870.6.

Example A17

N-(2-pyrazinylcarbonyl)-L-leucyl-L-isoleucyl-3-cyclohexylalanyl-2-oxo-3-aminopentanoyl-N-[[4-[(trifluoromethyl)sulfonyl]phenyl]sulfonyl]glycinamide Step (A17a) Following a procedure analogous to Step (A4a), compound 27b (Scheme 4) was coupled with 4-[(trifluoromethyl)sulfonyl]phenyl-sulfonamide to provide the title compound. MS found (M+1)+ 946.1.

Example A18

N-(2-pyrazinylcarbonyl)-L-leucyl-L-isoleucyl-3-cyclohexylalanyl-2-oxo-3-aminopentanoyl-N-[[4-(trifluoromethyl)phenyl]sulfonyl]glycinamide Step (A18a) Following a procedure analogous to (4a), compound 27b (Scheme 4) was coupled with 4-(trifluoromethyl)-phenylsulfonamide to provide the title compound. MS found (M+1)+ 881.8.

Example A19

N-(2-pyrazinylcarbonyl)-L-leucyl-L-isoleucyl-3-cyclohexylalanyl-2-oxo-3-aminopentanoyl-N-[(4-cyanophenyl)sulfonyl]glycinamide Step (A19a) Following a procedure analogous to Step (A4a), compound 27b (Scheme 4) was coupled with 4-cyanophenylsulfonamide to provide the title compound. MS found (M+1)+ 839.0.

Example A20

N-(2-pyrazinylcarbonyl)-L-leucyl-L-isoleucyl-3-cyclohexylalanyl-2-oxo-3-aminopentanoyl-N-[(3-chloro-4-methylphenyl)sulfonyl]glycinamide Step (A20a) Following a procedure analogous to Step (A4a), compound 27b (Scheme 4) was coupled with 3-chloro-4-methylphenylsulfonamide to provide the title compound. MS found (M+1)+ 862.3.

Example A21

N-(2-pyrazinylcarbonyl)-L-leucyl-L-isoleucyl-3-cyclohexylalanyl-2-oxo-3-aminopentanoyl-N-[(4-chloro-3-nitrophenyl)sulfonyl]glycinamide Step (A21a) Following a procedure analogous to Step (A4a), compound 27b (Scheme 4) was coupled with 4-chloro-3-nitrophenylsulfonamide to provide the title compound. MS found (M+1)+ 893.4.

Example A22

N-(2-pyrazinylcarbonyl)-L-leucyl-L-isoleucyl-3-cyclohexylalanyl-2-oxo-3-aminopentanoyl-N-[(3,5-dichlorophenyl)sulfonyl]glycinamide Step (A22a) Following a procedure analogous to Step (A4a), compound 27b (Scheme 4) was coupled with 3,5-dichlorophenylsulfonamide to provide the title compound. MS found (M+1)+ 882.9.

Example A23

N-(2-pyrazinylcarbonyl)-L-leucyl-L-isoleucyl-3-cyclohexylalanyl-2-oxo-3-aminopentanoyl-N-[(4-methyl-3-nitrophenyl)sulfonyl]glycinamide Step (A23a) Following a procedure analogous to Step (A4a), compound 27b (Scheme 4) was coupled with 4-methyl-3-nitrophenylsulfonamide to provide the title compound. MS found (M+1)+ 873.1.

Example A24

N-(2-pyrazinylcarbonyl)-L-leucyl-L-isoleucyl-3-cyclohexylalanyl-2-oxo-3-aminopentanoyl-N-[[2-chloro-5-(trifluoromethyl)phenyl]sulfonyl] glycinamide Step (A24a) Following a procedure analogous to Step (A4a), compound 27b (Scheme 4) was coupled with 2-chloro-5-(trifluoromethyl)phenyl-sulfonamide to provide the title compound. MS found (M+1)+ 916.5.

Example A25

N-(2-pyrazinylcarbonyl)-L-leucyl-L-isoleucyl-3-cyclohexylalanyl-2-oxo-3-aminopentanoyl-N-[(5-carboxy-2-chlorophenyl)sulfonyl]glycinamide Step (A25a) Following a procedure analogous to Step (A4a), compound 27b (Scheme 4) was coupled with 5-carboxy-2-chlorophenylsulfonamide to provide the title compound. MS found (M+1)+ 892.3.

Example A26

N-(2-pyrazinylcarbonyl)-L-leucyl-L-isoleucyl-3-cyclohexylalanyl-2-oxo-3-aminopentanoyl-N-[(2,5-dichlorophenyl)sulfonyl]glycinamide Step (A26a) Following a procedure analogous to Step (A4a), compound 27b (Scheme 4) was coupled with 2,5-dichlorophenylsulfonamide to provide the title compound. MS found (M+1)+ 879.5.

Example A27

N-(2-pyrazinylcarbonyl)-L-leucyl-L-isoleucyl-3-cyclohexylalanyl-2-oxo-3-aminopentanoyl-N-[(3,4-difluorophenyl)sulfonyl]glycinamide Step (A27a) Following a procedure analogous to Step (A4a), compound 27b (Scheme 4) was coupled with 3,4-diflorophenylsulfonamide to provide the title compound. MS found (M+1)+ 849.6.

Example A28

N-(2-pyrazinylcarbonyl)-L-leucyl-L-isoleucyl-3-cyclohexylalanyl-2-oxo-3-aminopentanoyl-N-[(3,5-dichloro-2-hydroxyphenyl)sulfonyl]glycinamide Step (A28a) Following a procedure analogous to Step (A4a), compound 27b (Scheme 4) was coupled with 3,5-dichoro-2-hydroxyphenylsulfonamide to provide the title compound. MS found (M−1)− 895.5.

Example A29

N-(2-pyrazinylcarbonyl)-L-leucyl-L-isoleucyl-3-cyclohexyl-L-alanyl-2-oxo-(3S)-3-amino pentanoyl-N-[(2,4,5-trichlorophenyl)-sulfonyl]glycinamide Step (A29a) Following a procedure analogous to Step (A4a), compound 27b (Scheme 4) was coupled with 2,4,5-trichlorophenylsulfonamide to provide the title compound. MS found (M−1)− 913.3.

Example A30

N-(2-pyrazinylcarbonyl)-L-leucyl-L-isoleucyl-3-cyclohexylalanyl-2-oxo-3-aminopentanoyl-N-[(5-carboxy-4-chloro-2-fluorophenyl)sulfonyl] glycinamide Step (A30a) Following a procedure analogous to Step (A4a), compound 27b (Scheme 4) was coupled with 5-carboxy-4-chloro-2-fluorophenyl sulfonamide to provide the title compound. MS found (M+1)+ 910.6.

Example A31

N-(2-pyrazinylcarbonyl)-L-leucyl-L-isoleucyl-3-cyclohexylalanyl-2-oxo-3-aminopentanoyl-N-[[5-(dimethylamino)-1-naphthalenyl]sulfonyl]glycinamide Step (A31a) Following a procedure analogous to Step (A4a), compound 27b (Scheme 4) was coupled with 5-(dimethylamino)-1-naphthalenylsulfonamide to provide the title compound. MS found $(M+1)^+$ 907.3.

Example A32

N-(2-pyrazinylcarbonyl)-L-leucyl-L-isoleucyl-3-cyclohexylalanyl-2-oxo-3-aminopentanoyl-N-(2-naphthalenylsulfonyl)glycinamide Step (A32a) Following a procedure analogous to Step (A4a), compound 27b (Scheme 4) was coupled with 2-naphthalenylsulfonamide to provide the title compound. MS found $(M+1)^+$ 864.2.

Example A33

N-(2-pyrazinylcarbonyl)-L-leucyl-L-isoleucyl-3-cyclohexyl-L-alanyl-2-oxo-(3S)-3-aminopentanoyl-N-[(4-(phenyl)phenyl)-sulfonyl]glycinamide Step (A33a) Following a procedure analogous to Step (A4a), compound 27b (Scheme 4) was coupled with 4-biphenylsulfonamide to provide the title compound. MS found $(M+1)^+$ 889.5.

Example A34

N-(2-pyrazinylcarbonyl)-L-leucyl-L-isoleucyl-3-cyclohexylalanyl-2-oxo-3-aminopentanoyl-N-[(6-ethoxy-2-benzothiazolyl)sulfonyl]glycinamide Step (A34a) Following a procedure analogous to Step (A4a), compound 27b (Scheme 4) was coupled with (6-ethoxy-2-benzothiazolyl)sulfonamide to provide the title compound. MS found $(M+1)^+$ 915.2.

Example A35

N-(2-pyrazinylcarbonyl)-L-leucyl-L-isoleucyl-3-cyclohexylalanyl-2-oxo-3-aminopentanoyl-N-[[2-chloro-5-[[(phenylmethyl)amino]carbonyl]phenyl]sulfonyl]glycinamide Step (A35a) Following a procedure analogous to Step (A4a), compound 27b (Scheme 4) was coupled with 2-chloro-5-[[(phenylmethyl)amino]carbonyl]-phenyl sulfonamide to provide the title compound. MS found $(M+1)^+$ 980.6.

Example A36

N-(2-pyrazinylcarbonyl)-L-leucyl-L-isoleucyl-3-cyclohexyl-L-alanyl-2-oxo-(3S)-3-aminopentanoyl-N-[[2-chloro-5-[[(2-trifluoroethyl)amino]carbonyl]phenyl]sulfonyl]glycinamide Step (A36a) Following a procedure analogous to Step (A4a), compound 27b (Scheme 4) was coupled with [[(2-trifluoroethyl)amino]carbonyl]phenyl sulfonamide to provide the title compound. MS found $(M-1)^-$ 970.5.

Example A37

N-(2-pyrazinylcarbonyl)-L-leucyl-L-isoleucyl-3-cyclohexyl-L-alanyl-2-oxo-(3S)-3-aminopentanoyl-N-[[2-chloro-5-[[(cyclopropylmethyl)amino]carbonyl]phenyl]sulfonyl]glycinamide Step (A37a) Following a procedure analogous to Step (A4a), compound 27b (Scheme 4) was coupled with 2-chloro-5-[[(cyclopropylmethyl)amino]-carbonyl]phenyl] sulfonamide to provide the title compound. MS found $(M+1)^+$ 944.4.

Example A38

N-(2-pyrazinylcarbonyl)-L-leucyl-L-isoleucyl-3-cyclohexyl-L-alanyl-2-oxo-(3S)-3-aminopentanoyl-N-[[3-nitro-4-(2-pyrimidinylthio)phenyl]sulfonyl]glycinamide Step (A38a) Following a procedure analogous to Step (A4a), compound 27b (Scheme 4) was coupled with 3-nitro-4-(2-pyrimidinylthio)phenyl sulfonamide to provide the title compound. MS found $(M+1)^+$ 968.4.

Example A39

N-(2-pyrazinylcarbonyl)-L-leucyl-L-isoleucyl-3-cyclohexyl-L-alanyl-2-oxo-(3S)-3-aminopentanoyl-N-[[2-chloro-4-(acetylamino)phenyl]sulfonyl]glycinamide Step (A39a) Following a procedure analogous to Step (A4a), compound 27b (Scheme 4) was coupled with 2-chloro-4-(acetylamino)phenyl sulfonamide to provide the title compound. MS found $(M-1)^-$ 902.5.

Example A40

N-(2-pyrazinylcarbonyl)-L-leucyl-L-isoleucyl-3-cyclohexyl-L-alanyl-2-oxo-(3S)-3-aminopentanoyl-N-[[3-chloro-4-(2-benzoxazolylthio)phenyl]sulfonyl]glycinamide Step (A40a) Following a procedure analogous to Step (A4a), compound 27b (Scheme 4) was coupled with 3-chloro-4-(2-benzoxazolylthio)phenyl sulfonamide to provide the title compound. MS found $(M-1)^-$ 1005.5.

Example A41

N-(2-pyrazinylcarbonyl)-L-leucyl-L-isoleucyl-3-cyclohexyl-L-alanyl-2-oxo-(3 S)-3-amino pentanoyl-N-[[3,5-dichloro-4-(4-nitrophenoxy)phenyl]sulfonyl]glycinamide Step (A41a) Following a procedure analogous to Step (A4a), compound 27b (Scheme 4) was coupled with 3,5-dichloro-4-(4-nitrophenoxy)phenyl sulfonamide to provide the title compound. MS found $(M+1)^+$ 1018.5.

Example A42

N-(2-pyrazinylcarbonyl)-L-leucyl-L-isoleucyl-3-cyclohexyl-L-alanyl-2-oxo-(3 S)-3-amino pentanoyl-N-[[5-(acetylamino)-1,3,4-thiadiazol-2-yl]sulfonyl]glycinamide Step (A42a) Following a procedure analogous to Step (A4a), compound 27b (Scheme 4) was coupled with 5-(acetylamino)-1,3,4-thiadiazol-2-yl sulfonamide to provide the title compound. MS found $(M+1)^+$ 878.5.

Example A43

N-(2-pyrazinylcarbonyl)-L-leucyl-L-isoleucyl-3-cyclohexyl-L-alanyl-2-oxo-(3 S)-3-amino pentanoyl-N-[(3-cyanophenyl)sulfonyl]glycinamide Step (A43a) Following a procedure analogous to Step (A4a), compound 27b (Scheme 4) was coupled with 3-cyanophenylsulfonamide to provide the title compound. MS found (M+1)+ 838.4.

Example A44

N-(2-pyrazinylcarbonyl)-L-leucyl-L-isoleucyl-3-cyclohexyl-L-alanyl-2-oxo-(3 S)-3-amino pentanoyl-N-[[3-(aminosulfonyl)-5-chlorophenyl] sulfonyl]glycinamide Step (A44a) Following a procedure analogous to Step (A4a), compound 27b (Scheme 4) was coupled with 3-(aminosulfonyl)-5-chlorophenyl sulfonamide to provide the title compound. MS found (M−1)⁻ 924.4.

Example A45

N-(2-pyrazinylcarbonyl)-L-leucyl-L-isoleucyl-3-cyclohexyl-L-alanyl-2-oxo-(3S)-3-amino pentanoyl-N-[[3,5-bis(trifluoromethyl)phenyl]sulfonyl] glycinamide Step (A45a) Following a procedure analogous to Step (A4a), compound 27b (Scheme 4) was coupled with 3,5-bis(trifluoromethyl)phenyl sulfonamide to provide the title compound. MS found (M+1)+ 949.4.

Example A46

N-(2-pyrazinylcarbonyl)-L-leucyl-L-isoleucyl-3-cyclohexyl-L-alanyl-2-oxo-(3S)-3-aminopentanoyl-N-[[4-[5-[3-(4-chlorophenyl)-3-oxo-1-propenyl]-2-furanyl]phenyl]sulfonyl]glycinamide Step (A46a): Following a procedure analogous to step (A4a), compound 27b (Scheme 4) was coupled with 4-[5-[3-(4-chlorophenyl)-3-oxo-1-propenyl]-2-furanyl] phenyl sulfonamide providing the title compound. MS found (M+1)+ 1043.5.

Example A47

N-(2-pyrazinylcarbonyl)-L-leucyl-L-isoleucyl-3-cyclohexyl-L-alanyl-2-oxo-(3S)-3-aminopentanoyl-N-[[3-[[(phenylmethyl)amino]carbonyl]phenyl] sulfonyl]glycinamide Step (A47a): Following a procedure analogous to step (A4a), 27b (Scheme 4) was coupled with 3-[(phenylmethyl)amino]-carbonyl]phenyl]sulfonamide providing the title product as crystalline solid. MS found (M+1)+ 946.6.

Example A48

N-(2-pyrazinylcarbonyl)-L-leucyl-L-isoleucyl-3-cyclohexyl-L-alanyl-2-oxo-(3S)-3-aminopentanoyl-N-[[3-[[(2,2,2-trifluoroethyl)amino]carbonyl]phenyl] sulfonyl]glycinamide Step (A48a): Following a procedure analogous to step (A4a), 27b (Scheme 4) was coupled with 3-[[(2,2,2-trifluoroethyl)amino]carbonyl]phenyl]sulfonamide providing the title product as crystalline solid. MS found (M+1)+ 938.5.

Example A49

N-(2-pyrazinylcarbonyl)-L-leucyl-L-isoleucyl-3-cyclohexyl-L-alanyl-2-oxo-(3S)-3-aminopentanoyl-N-[[3-[(benzoylamino)sulfonyl]-5-chlorophenyl] sulfonyl]glycinamide Step (A49a): Following a procedure analogous to step (A4a), 27b (Scheme 4) was coupled with 3-[(benzoylamino)sulfonyl]-5-chlorophenyl]-sulfonamide providing the title product as crystalline solid. MS found (M+1)+ 1030.6.

Example A50

N-(2-pyrazinylcarbonyl)-L-leucyl-L-isoleucyl-3-cyclohexyl-L-alanyl-5,5-difluoro-2-oxo-(3S)-3-aminopentanoylglycine Step (A50a): To a suspension of KOtBu (3.55 g, 31.7 mmol) in 15 mL CH$_2$Cl$_2$ was added N-CBZ-phosphonolycine trimethyl ester (9.46 g, 28.5 mmol) at −78° C. under N$_2$. This mixture was stirred for 15 min at this temperature and 2,2-difluoroacetaldehyde ethyl hemiacetal (4.0 g, 31.7 mmol) was added slowly. The resulted mixture was warmed up to room temperature and stirred overnight. Most solvent was removed and the residue was dissolved in ethyl acetate. The mixture was washed with cold water, dried over magnesium sulfate and concentrated. Flash chromatography (10–15% EtOAc/Hexane) gave the desired alkene (1.97 g, 24%) (Scheme 3, 11) as a clear oil (4:1 mixture of Z:E isomers). (M+1)+ 286.3.

Step (A50b): A mixture the material from Step (A50a) (0.90 g, 3.16 mmol) and of (+)-1,2-bis((2S,5S)-2,5-diethylphospholano)benzene-(cyclooctadiene)rhodium(I) trifluoromethanesulfonate ([Rh(COD)(S,S-di-Ethyl-DUPHOS)]+CF$_3$SO$_3$⁻) (25 mg, 0.03 mmol, 1 mol %) in 20 mL MeOH was hydrogenated at 50 psi for 15 h. After evaporation of solvent, the residue was dissolved in 30% EtOAc/Hexane and the solution was passed through a pad of silica gel to remove trace amount of the catalyst. Evaporation of solvent yielded the desired compound (Scheme 3, 12) as a crystalline solid (0.91 g, 100%).

Step (A50c): To a solution of the material from Step (A50b) (1.95 g, 5.23 mmol) in 50 mL CH$_2$Cl$_2$ under N$_2$ was added dropwise 5.49 mL DIBAL (1.0M solution in CH$_2$Cl$_2$, 5.49 mmol) at −78° C. over 15 min. After stirring at this temperature for 2 h, the mixture was quenched with 10 mL 5% potassium hydrogen sulfate solution. Then the mixture was warmed up to room temperature, diluted with CH$_2$Cl$_2$, washed with KHSO$_4$, NaHCO$_3$ and brine, dried over NaSO$_4$ and concentrated. Flash chromatography (15–30% EtOAc/Hexane) afforded 1.20 g (89%) of the desired aldehyde (Scheme 3, 13) as a white solid.

Step (A50d): Butyl lithium (2.5M solution in hexane, 4.1 mL, 10.3 mmol) was added dropwise to a solution of tris(methylthio)methane (1.58 g, 10.3 mmol) in 20 mL THF at −64° C. and the mixture was stirred at this temperature for 20 min. Then a solution of 0.66 g (2.57 mmol) of the material from Step (A50c) in 5.0 mL THF was added dropwise to the above mixture over 10 min. The resulting mixture was stirred at −30° C. and warmed up to room temperature. Then the reaction mixture was quenched with saturated NH$_4$Cl, and diluted with ethyl acetate. The organic phase was separated and washed with 5% KHSO$_4$, H$_2$O, NaHCO$_3$, brine, dried over NaSO$_4$ and concentrated. Flash chromatography (10–15% EtOAc/Hexane) yielded 0.90 g (85%) of the desired product (Scheme 3, 14) as a clear oil (a mixture of two diasteromers).

Step (A50e): To a solution of 0.15 g (0.36 mmol) of the material from Step (A50d) in a mixed solvent of MeOH/H$_2$O (12 mL/1.0 mL) were added 0.46 g (1.69 mmol) mercury(II) chloride and 0.12 g (0.58 mmol) mercury(II) oxide. The resulted suspension was stirred at room temperature for 2 h. Then the reaction mixture was filtered through a pad of Celite and most of the solvent was removed. The residue was dissolved in ethyl acetate, and this mixture was washed with 70% ammonium acetate, saturated ammonium chloride, sodium bicarbonate and dilute NaCl solution, dried over magnesium sulfate and concentrated. Chromatography (30% EtOAc/Hexane) gave 0.11 g (96%) of the desired product (Scheme 3, 15) as a clear oil (a mixture of two diastereomers).

Step (A50f): Following a procedure analogous to Step (A1d), the material from Step (A50e) was hydrogenated to afford the desired α-hydroxyl β-amino ester (Scheme 3, 16) as a crystalline solid.

Step (A50g): Following a procedure analogous to Step (A1j), the material from Step (A50f) was coupled with compound 24 (Scheme 4) to give the α-hydroxyester (Scheme 4, 25a) as a crystalline solid.

Step (A50h): Following a procedure analogous to Step (A2e), the material from Step (A50g) was converted to the desired α-hydroxyacid.

Step (A50i): Following a procedure analogous to Step (A1i), the above acid from Step (A50h) was coupled with Gly-OtBu to afford the desired product (Scheme 4, 25b) as a crystalline solid.

Step (A50j): Following a procedure analogous to Step (A1k), the material from Step (A50i) was oxidized to α-ketoamide (Scheme 4, 26b) as crystalline solid.

Step (A50k): Following a procedure analogous to Step (A1l), the material from Step (A50j) was treated with TFA to afford the title compound (Scheme 4, 27b) as a white solid. MS found $(M+1)^+$ 710.4.

Example A51

(3S)-5,5-difluoro-2-oxo-3-[[N-(2-pyrazinylcarbonyl)-L-leucyl-L-isoleucyl-3-cyclohexyl-L-alanyl]amino]-N-(2H-tetrazol-5-ylmethyl)pentanamide Step (A51a): Following a procedure analogous to Steps (A1f) and (A1g), the material from Step (A50h) was coupled with aminomethyltetrazole to afford the title product as acrystalline solid. MS found $(M+1)^+$ 734.4.

Example A52

N-(2-pyrazinylcarbonyl)-L-leucyl-L-isoleucyl-3-cyclohexyl-L-alanyl-5,5-difluoro-2-oxo-(3S)-3-aminopentanoyl-N-[(3,5-dichlorophenyl)sulfonyl]glycinamide Step (A52a) Following a procedure analogous to Step (A4a), the material from Step (A50k) was coupled with 3,5-dichlorophenyl-sulfonamide to give the title product. MS found $(M+1)^+$ 918.9.

Example A53

N-(2-pyrazinylcarbonyl)-L-leucyl-L-isoleucyl-3-cyclohexyl-L-alanyl-5,5-difluoro-2-oxo-(3S)-3-aminopentanoyl-N-[(3-chlorophenyl)sulfonyl]glycinamide Step (A53a) Following a procedure analogous to Step (A4a), the material from Step (A50k) was coupled with 2-chlorophenylsulfonamide to give the title product. MS found $(M+1)^+$ 883.3.

Example A54

N-(2-pyrazinylcarbonyl)-L-leucyl-L-isoleucyl-3-cyclohexyl-L-alanyl-5,5-difluoro-2-oxo-(3S)-3-aminopentanoyl-N-[5-(acetylamino)-1,3,4-thiadiazol-2-yl]sulfonyl]-glycinamide Following a procedure analogous to Step (A4a), the material from Step (A50k) was coupled with [5-(acetylamino)-1,3,4-thiadiazol-2-yl]sulfonamide to give the title product. MS found $(M+1)^+$ 914.5.

Example A55

N-(2-pyrazinylcarbonyl)-L-leucyl-L-isoleucyl-3-cyclohexyl-L-alanyl-5,5-difluoro-2-oxo-(3S)-3-aminopentanoyl-N-(3-aminosulfonyl-5-chlorophenyl)sulfonyl]glycinamide Step (A55a): Following a procedure analogous to step (A4a), the material from step (A50k) was coupled with [3-aminosulfonyl-5-chlorophenyl]sulfonamide to give the title product. MS found $(M+1)^+$ 962.4.

Example A56

(3S)-5,5,5-trifluoro-2-oxo-3-[[N-(2-pyrazinylcarbonyl)-L-leucyl-L-isoleucyl-3-cyclohexyl-L-alanyl]amino]-N-(2H-tetrazol-5-ylmethyl)pentanamide Step (A56a): Following a procedure analogous to Steps (A1a–d), 2-hydroxyl-3-amino-5-trifluorovaleric acid methylester (Scheme, 1, 5 where R1=H, R2=CH2CF3, W'=OMe) was obtained. (A56b): Following a procedure analogous to Step (A1j), the product from (A56a) was coupled with the product from (A1I) to give the desired product (Scheme 4, 25a).

(A56c): Following a procedure analogous to Steps (A2e–g), the material from Step (A56b) was converted to the desired product as a white solid (Scheme 6). MS found: (M+1)+752.9.

Example A57

N-[4-sec-butyl-15-{[(3-chloro-5-{[(3,3,3-trifluoropropanoyl)amino]sulfonyl}phenyl)sulfonyl]amino}-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A57a): Following a procedure analogous to step (A4a), the material from step (A50k) was coupled with (3-chloro-5-{[(3,3,3-trifluoropropanoyl)amino]sulfonamide to give the title product. MS found $(M+1)^+$ 1073.4.

Example A58

N-[4-sec-butyl-15-[({3-chloro-5-[(hexanoylamino)sulfonyl]phenyl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A58a): Following a procedure analogous to step (A4a), the material from step (A50k) was coupled with ({3-chloro-5-[(hexanoylamino)sulfonamide to give the title product. MS found $(M+1)^+$ 1061.3.

Example A59

N-[15-[([1,1'-biphenyl]-3-ylsulfonyl)amino]-4-sec-butyl-7-(cyclohexylmethyl)-10-ethyl-1-isobutyl-2,5,8,11,12,15-hexaoxo-3,6,9,13-tetraazapentadec-1-yl]-2-pyrazinecarboxamide Step (A59a): Following a procedure analogous to step (A4a), the material from step (A50k) was coupled with ([1,1'-biphenyl]-3-yl] sulfonamide to give the title product. MS found (M+1)+ 890.4.

Example A60

N-(4-sec-butyl-7-(cyclohexylmethyl)-10-ethyl-1-isobutyl-15-{[(4'-methoxy[1,1'-biphenyl]-4-yl)sulfonyl]amino}-2,5,8,11,12,15-hexaoxo-3,6,9,13-tetraazapentadec-1-yl)-2-pyrazinecarboxamide Step (A60a): Following a procedure analogous to step (A4a), the material from step (A50k) was coupled with [(4'-methoxy[1,1'-biphenyl]-4-yl sulfonamide to give the title product. MS found (M+1)+ 920.1.

Example A61

N-(4-sec-butyl-7-(cyclohexylmethyl)-15-{[(3',5'-dichloro[1,1'-biphenyl]-4-yl)sulfonyl]amino}-10-ethyl-1-isobutyl-2,5,8,11,12,15-hexaoxo-3,6,9,13-tetraazapentadec-1-yl)-2-pyrazinecarboxamide Step (A61a): Following a procedure analogous to step (A4a), the material from step (A50k) was coupled with [(3',5'-dichloro[1,1'-biphenyl]-4-yl)sulfonamide to give the title product. MS found (M+1)+ 958.5.

Example A62

N-[4-sec-butyl-15-{[(4'-chloro[1,1'-biphenyl]-3-yl)sulfonyl]amino}-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A62a): Following a procedure analogous to step (A4a), the material from step (A50k) was coupled with [(4'-chloro[1,1'-biphenyl]-3-yl)sulfonamide to give the title product. MS found (M+1)+ 960.6.

Example A63

N-[4-sec-butyl-7-(cyclohexylmethyl)-10-(2,2-difluoroethyl)-1-isobutyl-15-({[3-(2-methylphenoxy)phenyl]sulfonyl}amino)-2,5,8,11,12,15-hexaoxo-3,6,9,13-tetraazapentadec-1-yl)-2-pyrazinecarboxamide Step (A63a): Following a procedure analogous to step (A4a), the material from step (A50k) was coupled with [3-(2-methylphenoxy)phenyl]sulfonamide to give the title product. MS found (M+1)+ 956.2.

Example A64

N-[4-sec-butyl-15-({[3-(2-chlorophenoxy)phenyl]sulfonyl}amino)-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A64a): Following a procedure analogous to step (A4a), the material from step (A50k) was coupled with [3-(2-chlorophenoxy)phenyl]phenyl]sulfonamide to give the title product. MS found (M+1)+ 976.3.

Example A65

(3S,6S,9S,12S)-9-(cyclohexylmethyl)-12-(2,2-difluoroethyl)-3-isobutyl-6-[(1R)-1-methylpropyl]-1,4,7,10,13-pentaoxo-1-(2-pyrazinyl)-2,5,8,11-tetraazatetradecan-14-oic acid Step (A65a): Following a procedure analogous to step (A4), the material from step (A50k) was treated with Dess-Martin reagent to obtained the title product. MS found (M+1)+ 653.5.

Example A66

N-(4-sec-butyl-7-(cyclohexylmethyl)-10-(2,2-difluoroethyl)-1-isobutyl-15-{[(4'-methyl[1,1'-biphenyl]-3-yl)sulfonyl]amino}-2,5,8,11,12,15-hexaoxo-3,6,9,13-tetraazapentadec-1-yl)-2-pyrazinecarboxamide Step (A66a): Following a procedure analogous to step (A4a), the material from step (A50k) was coupled with [(4'-methyl[1,1'-biphenyl]-3-yl)sulfonamide to give the title product. MS found (M+1)+ 940.1.

Example A67

N-[15-({[3',5'-bis(trifluoromethyl)[1,1'-biphenyl]-3-yl]sulfonyl}amino)-4-sec-butyl-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A67a): Following a procedure analogous to step (A4a), the material from step (A50k) was coupled with [3',5'-bis(trifluoromethyl)[1,1'-biphenyl]-3-yl] sulfonamide to give the title product. MS found (M+1)+ 1061.8.

Example A68

N-[4-sec-butyl-15-[({5-[(4-cyanobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A68a): Following a procedure analogous to step (A4a), the material from step (A50k) was coupled with {[(4-cyanobenzoyl)amino]-1,3,4-thiadiazol-2-yl}sulfonamide to give the title product. MS found (M+1)+ 1001.9.

Example A69

N-[4-sec-butyl-15-[({5-[(2-chlorobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A69a): Following a procedure analogous to step (A4a), the material from step (A50k) was coupled with {5-[(2-chlorobenzoyl)amino]-1,3,4-thiadiazol-2-yl}sulfonamide to give the title product. MS found (M+1)+ 1011.2.

Example A70

N-{4-sec-butyl-7-(cyclohexylmethyl)-10-(2,2-difluoroethyl)-1-isobutyl-15-[({5-[(4-methoxybenzoyl)amino]-1,3,4-thiadiazol-2-yl}sulfonyl)amino]-2,5,8,11,12,15-hexaoxo-3,6,9,13-tetraazapentadec-1-yl}-2-pyrazinecarboxamide Step (A70a): Following a procedure analogous to step (A4a), the material from step (A50k) was coupled with {5-[(4-methoxybenzoyl)amino]-1,3,4-thiadiazol-2-yl}sulfonamide to give the title product. MS found (M+1)$^+$ 1006.8.

Example A71

N-{4-sec-butyl-7-(cyclohexylmethyl)-10-(2,2-difluoroethyl)-1-isobutyl-15-[({5-[(3-methoxybenzoyl)amino]-1,3,4-thiadiazol-2-yl}sulfonyl)amino]-2,5,8,11,12,15-hexaoxo-3,6,9,13-tetraazapentadec-1-yl}-2-pyrazinecarboxamide Step (A71a): Following a procedure analogous to step (A4a), the material from step (A50k) was coupled with {5-[(3-methoxybenzoyl)amino]-1,3,4-thiadiazol-2-yl}sulfonamide to give the title product. MS found (M+1)$^+$ 1007.1.

Example A72

N-{4-sec-butyl-7-(cyclohexylmethyl)-10-(2,2-difluoroethyl)-15-[({5-[(3,5-dimethylbenzoyl)amino]-1,3,4-thiadiazol-2-yl}sulfonyl)amino]-1-isobutyl-2,5,8,11,12,15-hexaoxo-3,6,9,13-tetraazapentadec-1-yl}-2-pyrazinecarboxamide Step (A72a): Following a procedure analogous to step (A4a), the material from step (A50k) was coupled with {5-[(3,5-dimethylbenzoyl)amino]-1,3,4-thiadiazol-2-yl}sulfonamide to give the title product. MS found (M+1)$^+$ 1007.1.

Example A73

N-(4-sec-butyl-7-(cyclohexylmethyl)-10-(2,2-difluoroethyl)-1-isobutyl-2,5,8,11,12,15-hexaoxo-15-{[(3-phenoxyphenyl)sulfonyl]amino}-3,6,9,13-tetraazapentadec-1-yl)-2-pyrazinecarboxamide Step (A73a): Following a procedure analogous to step (A4a), the material from step (A50k) was coupled with (3-phenoxyphenyl)sulfonamide to give the title product. MS found (M+1)$^+$ 941.8.

Example A74

6-sec-butyl-9-(cyclohexylmethyl)-12-ethyl-3-isobutyl-1,4,7,10,13-pentaoxo-1-(2-pyrazinyl)-2,5,8,11-tetraazatetradecan-14-oic acid Step (A74a): Following a procedure analogous to step (A65a), the material from step (A50k) was treated with Dess-Martin reagent to give the title product. MS found (M+1)$^+$ 617.4.

Example A75

N-{(4-sec-butyl-7-(cyclohexylmethyl)-10-(2,2-difluoroethyl)-1-isobutyl-15-[({5-[(3-methylbutanoyl)amino]-1,3,4-thiadiazol-2-yl}sulfonyl)amino]-2,5,8,11,12,15-hexaoxo-3,6,9,13-tetraazapentadec-1-yl}-2-pyrazinecarboxamide Step (A75a): Following a procedure analogous to step (A4a), the title compound was obtained. MS found (M+1)$^+$ 957.0.

Example A76

N-[4-sec-butyl-7-(cyclohexylmethyl)-10-(2,2-difluoroethyl)-15-({[5-(hexanoylamino)-1,3,4-thiadiazol-2-yl]sulfonyl}amino)-1-isobutyl-2,5,8,11,12,15-hexaoxo-3,6,9,13-tetraazapentadec-1-yl]-2-pyrazinecarboxamide Step (A76a): Following a procedure analogous to step (A4a), the title compound was obtained. MS found (M+1)$^+$ 971.0.

Example A77

Methyl (3S,6S,9S,12S)-9-(cyclohexylmethyl)-12-(2,2-difluoroethyl)-3-isobutyl-6-[(1R)-1-methylpropyl]-1,4,7,10,13,14-hexaoxo-1-(2-pyrazinyl)-2,5,8,11,15-pentaazaheptadecan-17-oate Step (A77a): Following a procedure analogous to step (A4a), the title compound was obtained. MS found (M+1)$^+$ 724.4.

Example A78

N-[4-sec-butyl-15-{[(3-chloro-5-{[(3-chlorobenzoyl)amino]sulfonyl}phenyl)sulfonyl]amino}-7-(cyclohexylmethyl)-10-ethyl-1-isobutyl-2,5,8,11,12,15-hexaoxo-3,6,9,13-tetraazapentadec-1-yl]-2-pyrazinecarboxamide Step (A78a): Following a procedure analogous to step (A4a), the title compound was obtained. MS found (M+1)$^+$ 1066.1.

Example A79

N-[4-sec-butyl-7-(cyclohexylmethyl)-10-(2,2-difluoroethyl)-1-isobutyl-2,5,8,11,12,15-hexaoxo-15-({[4'-(trifluoromethyl)[1,1'-biphenyl]-3-yl]sulfonyl}amino)-3,6,9,13-tetraazapentadec-1-yl]-2-pyrazinecarboxamide Step (A79a): Following a procedure analogous to step (A4a), the title compound was obtained. MS found (M+1)$^+$ 993.9.

Example A80

N-[15-[([1,1'-biphenyl]-3-ylsulfonyl)amino]-4-sec-butyl-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A80a): Following a procedure analogous to step (A4a), the title compound was obtained. MS found (M+1)$^+$ 926.1.

Example A81

N-[4-sec-butyl-15-[({5-[(4-tert-butylbenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A81a): Following a procedure analogous to step (A4a), the title compound was obtained. MS found (M+1)$^+$ 1033.1.

Example A82

N-[4-sec-butyl-15-{[(3-chloro-5-{[(3-methylbutanoyl)amino]sulfonyl}phenyl)sulfonyl]amino}-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A82a): Following a procedure analogous to step (A4a), the title compound was obtained. MS found (M+1)$^+$ 1047.7.

Example A83

N-{(1S,4S,7S,10S)-7-(cyclohexylmethyl)-10-(2,2-difluoroethyl)-1-isobutyl-14-[4-(4-methoxyphenyl)-5-(trifluoromethyl)-4H-1,2,4-triazol-3-yl]-4-[(1R)-1-methylpropyl]-2,5,8,11,12-pentaoxo-3,6,9,13-tetraazatetradec-1-yl}-2-pyrazinecarboxamide Step (A83a): Following a procedure analogous to step (A4a), the title compound was obtained. MS found (M+1)$^+$ 907.8.

Example A84

N-{4-sec-butyl-7-(cyclohexylmethyl)-10-(2,2-difluoroethyl)-15-[({5-[(4-ethylbenzoyl)amino]-1,3,4-thiadiazol-2-yl}sulfonyl)amino]-1-isobutyl-2,5,8,11,12,15-hexaoxo-3,6,9,13-tetraazapentadec-1-yl}-2-pyrazinecarboxamide Step (A84a): Following a procedure analogous to step (A4a), the title compound was obtained. MS found (M+1)$^+$ 1005.2.

Example A85

N-[4-sec-butyl-15-[({5-[(4-chlorobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A85a): Following a procedure analogous to step (A4a), the title compound was obtained. MS found (M+1)$^+$ 1011.5.

Example A86

N-[4-sec-butyl-7-(cyclohexylmethyl)-15-[({5-[(3,5-difluorobenzoyl)amino]-1,3,4-thiadiazol-2-yl}sulfonyl)amino]-10-(2,2-difluoroethyl)-1-isobutyl-2,5,8,11,12,15-hexaoxo-3,6,9,13-tetraazapentadec-1-yl]-2-pyrazinecarboxamide Step (A86a): Following a procedure analogous to step (A4a), the title compound was obtained. MS found (M+1)$^+$ 1013.1.

Example A87

N-[4-sec-butyl-15-[(5-[(3-chlorobenzoyl)amino]-1,3,4-thiadiazol-2-yl}sulfonyl)amino]-7-(cyclohexylmethyl)-10-(2,2-difluoroethyl)-1-isobutyl-2,5,8,11,12,15-hexaoxo-3,6,9,13-tetraazapentadec-1-yl]-2-pyrazinecarboxamide Step (A87a): Following a procedure analogous to step (A4a), the title compound was obtained. MS found (M+1)$^+$ 1011.3.

Example A88

N-{(1S, 4S,7S,10S)-7-(cyclohexylmethyl)-10-ethyl-1-isobutyl-4-[(1R)-1-methylpropyl]-2,5,8,11,12-pentaoxo-3,6,9,13-tetraazahexadec-15-en-1-yl}-2-pyrazinecarboxamide Step (A88a): Following a procedure analogous to steps (A1) and (A4a). The detailed procedure can be found in Han, W. ect.; *Bioorg. Med. Chem. Lett.* 10, 711–713, 2000 and is hereby incorporated by reference in its entirety. The title compound was obtained. MS found (M+1)$^+$ 656.4.

Example A89

N-{(1S,4S,7S,10S)-7-(cyclohexylmethyl)-10-ethyl-1-isobutyl-4-[(1R)-1-methylpropyl]-2,5,8,11,12-pentaoxo-3,6,9,13-tetraazahexadec-15-yn-1-yl}-2-pyrazinecarboxamide Step (A89a): Following a procedure analogous to step (A88a), the title compound was obtained. MS found (M+1)$^+$ 654.5.

Example A90 tert-butyl (3S,6S,9S,12S)-9-(cyclohexylmethyl)-12-ethyl-3-isobutyl-6-[(1R)-1-methylpropyl]-1,4,7,10,13,14-hexaoxo-1-(2-pyrazinyl)-2,5,8,11,15-pentaazaheptadecan-17-oate Step (A90a): Following a procedure analogous to step (A88a), the title compound was obtained. MS found (M+1)$^+$ 730.5.

Example A91

N-{(1S,4S,7S,10S)-7-(cyclohexylmethyl)-10-ethyl-1-isobutyl-4-[(1R)-1-methylpropyl]-2,5,8,11,12-pentaoxo-14-phenyl-3,6,9,13-tetraazatetradec-1-yl}-2-pyrazinecarboxamide Step (A91a): Following a procedure analogous to step (A88a), the title compound was obtained. MS found (M+1)$^+$ 706.4.

Example A92

N-((1S)-1-{[((1S,2R)-1-{[((1S)-1-(cyclohexylmethyl)-2-{[(1S)-1-ethyl-2,3-dioxo-3-(1-pyrrolidinyl)propyl]amino}-2-oxoethyl)amino]carbonyl}-2-methylbutyl)amino]carbonyl}-3-methylbutyl)-2-pyrazinecarboxamide Step (A92a): Following a procedure analogous to step (A88a), the title compound was obtained. MS found (M+1)$^+$ 670.3.

Example A93

N-{(1S,4S,7S,10S)-7-(cyclohexylmethyl)-10-ethyl-15,15,15-trifluoro-1-isobutyl-4-[(1R)-1-methylpropyl]-2,5,8,11,12-pentaoxo-3,6,9,13-tetraazapentadec-1-yl}-2-pyrazinecarboxamide Step (A93a): Following a procedure analogous to step (A88a), the title compound was obtained. MS found (M+1)$^+$ 698.2.

Example A94

N-{(1S,4S,7S,10S)-15-amino-7-(cyclohexylmethyl)-10-ethyl-1-isobutyl-4-[(1R)-1-methylpropyl]-2,5,8,11,12,15-hexaoxo-3,6,9,13-tetraazapentadec-1-yl}-2-pyrazinecarboxamide Step (A94a): Following a procedure analogous to step (A88a), the title compound was obtained. MS found (M+1)$^+$ 673.4.

Example A95

(3S,6S,9S,12S,16S)-9-(cyclohexylmethyl)-12-ethyl-3-isobutyl-16-methyl-6-[(1R)-1-methylpropyl]-1,4,7,10,13,14-hexaoxo-1-(2-pyrazinyl)-2,5,8,11,15-pentaazaheptadecan-17-oic acid Step (A95a): Following a procedure analogous to step (A88a), the title compound was obtained. MS found $(M+1)^+$ 688.5.

Example A96

N-[9-sec-butyl-6-(cyclohexylmethyl)-3-ethyl-12-isobutyl-2,5,8,11,14-pentaoxo-14-(2-pyrazinyl)-4,7,10,13-tetraazatetradec-1-anoyl]aspartic acid Step (A96a): Following a procedure analogous to step (A88a), the title compound was obtained. MS found $(M+1)^+$ 732.4.

Example A97

(3S,6S,9S,12S)-9-(cyclohexylmethyl)-12-ethyl-3-isobutyl-6-[(1R)-1-methylpropyl]-1,4,7,10,13,14-hexaoxo-1-(2-pyrazinyl)-2,5,8,11,15-pentaazaoctadecan-18-oic acid Step (A97a): Following a procedure analogous to step (A88a), the title compound was obtained. MS found $(M+1)^+$ 688.5.

Example B1

1,1-dimethylethyl N-(2-pyrazinylcarbonyl)-L-leucyl-L-isoleucyl-(4R)-4-(phenylmethoxy)-L-prolyl-5,5-difluoro-2-oxo-(3S)-3-aminopentanoylglycine Step (B1a): Following a procedure analogous to step (A1) and (A50), the compound 32a {Pz(CO)-Lue-Ile-Hyp(OBn)-NHCH(CH$_2$CHF$_2$)CH(OH)CO$_2$Me} was obtained as crystalline solid. MS found $(M+1)^+$ 719.1.

Step (B1b): Following a procedure analogous to step (A2e), the product from step (B1a) was treated with LiOH to provide the corresponding α-hydroxyacid as crystalline solid. MS found $(M+1)^+$ 715.1; $(M-1)^-$ 713.

Step (B1c): Following a procedure analogous to step (A1j) and step (A1k), the above material was coupled with Gly-OtBu followed by oxidation to provide the title product (Scheme 5, 33) as crystalline solid. MS found $(M+1)^+$ 816.4.

Example B2

N-(2-pyrazinylcarbonyl)-L-leucyl-L-isoleucyl-(4R)-4-(phenylmethoxy)-L-prolyl-5,5-difluoro-2-oxo-(3S)-3-aminopentanoylglycine Step (B2a): Following a procedure analogous to Step (A1l), the material from Step (B1c) was treated with TFA to afford title product (Scheme 5, 34) as a white solid. MS found $(M+1)^+$ 760.3.

Example B3

(4R)-1-[N-(2-pyrazinylcarbonyl)-L-leucyl-L-isoleucyl]-N-[(1S)-1-(2,2-difluoroethyl)-2,3-dioxo-3-[(2H)-tetrazol-5-ylmethyl)amino]propyl]-4-(phenylmethoxy)-L-prolinamide Step (B3a): Following a procedure analogous to Steps (A2f–g), the material from Step (B1b) was coupled with aminotetrazole followed by oxidation to give the title product as a white solid. MS found $(M+1)^+$ 784.4.

Example B4

(4R)-N-(2-pyrazinylcarbonyl)-L-leucyl-L-isoleucyl-N-[(1S)-1-(2,2-difluoroethyl)-3-methoxy-2,3-dioxopropyl]-4-(phenylmethoxy)-L-prolinamide Step (B4a): Following a procedure analogous to step (A2g), the material from (B1a) was oxidized to the desired product. MS found $(M+1)^+$ 717.3.

Example B5

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(3-chlorophenyl)sulfonyl]glycinamide Step (B5a): Following a procedure analogous to Step (A4a), the material from Step (B2a) was coupled with 3-chlorophenylsulfonamide to afford the title product as a white solid. MS found $(M+1)^+$ 933.3.

Example B6

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(5-carboxy-2-chlorophenyl)-sulfonyl]glycinamide Step (B6a): Following a procedure analogous to step (4a), the material from step (B2a) was coupled with 5-carboxy-2-chlorophenylsulfonamide to afford title product as white solid. MS found $(M+1)^+$ 978.2.

Example B7

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(5-acetylamino)1,3,4-thiadiazol-2-yl)sulfonyl]glycinamide Step (B7a): Following a procedure analogous to step (4a), the material from step (B2a) was coupled with N-[(5-acetylamino)1,3,4-thiadiazol-2-yl)sulfonamide to afford title product as white solid. MS found $(M+1+H_2O)^+$ 982.5.

Example B8

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[3,5-dichlorophenyl)sulfonyl]glycinamide Step (B8a): Following a procedure analogous to step (4a), the material from step (B2a) was coupled with (3,5-dichlorophenyl) sulfonamide to afford title product as white solid. MS found $(M+1)^+$ 967.6.

Example B9

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-(4-methyl-3-nitrophenyl)sulfonyl]-glycinamide Step (B9a): Following a procedure analogous to step (4a), the material from step (B2a) was coupled with (4-methyl- 3-nitrophenyl) sulfonamide to afford title product as white solid. MS found (M+1)⁺ 958.4.

Example B10

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-(3-carboxyl-4-chloro-2-fluorophenyl)sulfonyl]-glycinamide Step (B10a): Following a procedure analogous to step (4a), the material from step (B2a) was coupled with (3-carboxyl-4-chloro-2-fluorophenyl)sulfonamide to afford title product as white solid. MS found (M+1)⁺ 995.4.

Example B11

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-[(3-chloro-4-acetylamino)phenyl]sulfonyl]-glycinamide Step (B11a): Following a procedure analogous to step (4a), the material from step (B2a) was coupled with (3-chloro-4-acetylamino)phenyl sulfonamide to afford title product as white solid. MS found (M+1)⁺ 1116.5.

Example B12

N-((1S)-1-{[((1S,2R)-1-{[(2S,4R)-2-({[(1S)-3-({2-[({3-[(benzoylamino)sulfonyl]-5-chlorophenyl}sulfonyl)amino]-2-oxoethyl}amino)-1-(2,2-difluoroethyl)-2,3-dioxopropyl]amino}carbonyl)-4-(benzyloxy)pyrrolidinyl]carbonyl}-2-methylbutyl)amino]carbonyl}-3-methylbutyl)-2-pyrazinecarboxamide Step (B12a): Following a procedure analogous to step (B7a), the title compound was obtained. MS found (M+1)⁺ 1117.4.

Example B13 tert-butyl ({(3S)-3-[({(2S,4R)-4-(benzyloxy)-1-[(2S)-3-methyl-2-({(2S)-3-methyl-2-[(2-pyrazinylcarbonyl)amino]butanoyl}amino)butanoyl]pyrrolidinyl}carbonyl)amino]-5,5-difluoro-2-oxopentanoyl}amino)acetate Step (B13a): Following a procedure analogous to step (B7a), the title compound was obtained. MS found (M+1)⁺ 788.9.

Example B14

N-((1S)-1-{[((1S,2R)-1-{[(2S,4R)-4-(benzyloxy)-2-({[(1S)-3-[(2-{[(3-chloro-4-methylphenyl)sulfonyl]amino}-2-oxoethyl)amino]-1(2,2-difluoroethyl)-2,3-dioxopropyl]amino}carbonyl)pyrrolidinyl]carbonyl}-2-methylbutyl)amino]carbonyl}-3-methylbutyl)-2-pyrazinecarboxamide Step (B14a): Following a procedure analogous to step (B7a), the title compound was obtained. MS found (M+1)⁺ 948.3.

Example B15

N-((1S)-1-{[((1S,2R)-1-{[(2S,4R)-4-(benzyloxy)-2-({[(1S)-3-({2-[({5-[(3-chlorobenzoyl) amino]-1,3,4-thiadiazol-2-yl}sulfonyl)amino]-2-oxoethyl}amino)-1-(2,2-difluoroethyl)-2,3-dioxopropyl] amino}carbonyl)pyrrolidinyl]carbonyl}-2-methylbutyl)amino]carbonyl}-3-methylbutyl)-2-pyrazinecarboxamide Step (B15a): Following a procedure analogous to step (B7a), the title compound was obtained. MS found (M+1)⁺ 1061.3.

Example B16

Methyl ({(3S)-3-[({(2S,4R)-4-(benzyloxy)-1-[(2S,3R)-3-methyl-2-({(2S)-4-methyl-2-[(2-pyrazinylcarbonyl)amino]pentanoyl]amino)pentanoyl]pyrrolidinyl}carbonyl)amino]-5,5-difluoro-2-oxopentanoyl}amino)acetate Step (B16a): Following a procedure analogous to step (B7a), the title compound was obtained. MS found (M+1)⁺ 774.6.

Example B17

N-((1S)-1-{[((1S,2R)-1-{[(2S,4R)-4-(benzyloxy)-2-({[(1S)-3-[(2-{[(2,4-dichloro-5-methylphenyl)sulfonyl]amino}-2-oxoethyl)amino]-1-(2,2-difluoroethyl)-2,3-dioxopropyl]amino}carbonyl)pyrrolidinyl]carbonyl}-2-methylbutyl)amino]carbonyl}-3-methylbutyl)-2-pyrazinecarboxamide Step (B17a): Following a procedure analogous to step (B7a), the title compound was obtained. MS found (M+1)⁺ 982.6.

Example B18

N-[(1S)-1-({[(1S,2R)-1-({(2S,4R)-4-(benzyloxy)-2-[({(1S)-1-(2,2-difluoroethyl)-3-[(2-([(3,4-difluorophenyl)sulfonyl]amino}-2-oxoethyl)amino]-2,3-dioxopropyl}amino)carbonyl]pyrrolidinyl}carbonyl)-2-methylbutyl]amino}carbonyl)-3-methylbutyl]-2-pyrazinecarboxamide Step (B18a): Following a procedure analogous to step (B7a), the title compound was obtained. MS found (M+1)⁺ 935.7.

Example B19

Methyl 5-({[({(3S)-3-[({(2S,4R)-4-(benzyloxy)-1-[(2S,3R)-3-methyl-2-({(2S)-4-methyl-2-[(2-pyrazinylcarbonyl)amino]pentanoyl}amino)pentanoyl]pyrrolidinyl}carbonyl)amino]-5,5-difluoro-2-oxopentanoyl}amino)acetyl]amino}sulfonyl)-2,4-dichlorobenzoate Step (B19a): Following a procedure analogous to step (B7a), the title compound was obtained. MS found (M+1)⁺ 1026.7.

Example B20

N-{(1S)-1-[({(1S,2R)-1-[((2S,4R)-4-(benzyloxy)-2-{[((1S)-1-(2,2-difluoroethyl)-3-{[2-({[4-(3,5-dimethyl-1-piperidinyl)-3-nitrophenyl]sulfonyl}amino)-2-oxoethyl]amino}-2,3-dioxopropyl)amino]carbonyl}pyrrolidinyl)carbonyl]-2-methylbutyl}amino)carbonyl]-3-methylbutyl}-2-pyrazinecarboxamide Step (B20a): Following a procedure analogous to step (B7a), the title compound was obtained. MS found (M+1)⁺ 1056.0.

Example B21

N-[(1S)-1-({[(1S,2R)-1-({(2S,4R)-4-(benzyloxy)-2-[({(1S)-1-(2,2-difluoroethyl)-3-[(2-{[(3-nitrophenyl)sulfonyl]amino}-2-oxoethyl)amino]-2,3-dioxopropyl}amino)carbonyl]pyrrolidinyl}carbonyl)-2-methylbutyl]amino}carbonyl)-3-methylbutyl]-2-pyrazinecarboxamide Step (B21a): Following a procedure analogous to step (B7a), the title compound was obtained. MS found (M+1)⁺ 944.8.

Example B22

N-{(1S)-1-[({(1S,2R)-1-[((2S,4R)-4-(benzyloxy)-2-{[((1S)-1-(2,2-difluoroethyl)-3-{[2-({[5-(hexanoylamino)-1,3,4-thiadiazol-2-yl]sulfonyl}amino)-2-oxoethyl]amino}-2,3-dioxopropyl)amino]carbonyl}pyrrolidinyl)carbonyl]-2-methylbutyl}amino)carbonyl]-3-methylbutyl}-2-pyrazinecarboxamide Step (B22a): Following a procedure analogous to step (B7a), the title compound was obtained. MS found (M+1)⁺ 1021.1.

Example B23

5-({[({(3S)-3-[({(2S,4R)-4-(benzyloxy)-1-[(2S,3R)-3-methyl-2-({(2S)-4-methyl-2-[(2-pyrazinylcarbonyl)amino]pentanoyl}amino)pentanoyl]pyrrolidinyl}carbonyl)amino]-5,5-difluoro-2-oxopentanoyl}amino)acetyl]amino}sulfonyl)-2,4-dichlorobenzoic acid Step (B23a): Following a procedure analogous to step (B7a), the title compound was obtained. MS found (M+1)⁺ 1012.6.

Example C1

N-[[5-(4-chlorophenyl)-2-furanyl]carbonyl]-L-isoleucyl-3-cyclohexylalanyl-2-oxo-3-aminopentanoylglycine Step (C1a): Following the procedures analogous to step (A1) and step (A2), the title product was obtained as crystalline solid. MS found (M+1)⁺ 659.4.

Example C2

N-[[5-(4-chlorophenyl)-2-furanyl]carbonyl]-Lisoleucyl-3-cyclohexylalanyl-2-oxo-3-aminopentanoyl-N-[(trifluoromethyl)sulfonyl]glycinamide Step (C2a): Following a procedure analogous to step (A4a), the material from step (C1a) was coupled with trifluoromethylsulfonamide to afford the title product as crystalline solid. MS found (M+1)⁺ 790.3.

Example C3

N-[[5-(4-chlorophenyl)-2-furanyl]carbonyl]-Lisoleucyl-3-cyclohexylalanyl-2-oxo-3-aminopentanoyl-N-[(3,5-dichlorophenyl)sulfonyl]glycinamide Step (C3a): Following the procedures analogous to step (A4a), the material from step (C1a) was coupled with 3,5-dichlorophenyl)sulfonamide to afford the title product as crystalline solid. MS found (M+1)⁺ 866.6.

Example C4

N-[[5-(4-chlorophenyl)-2-furanyl]carbonyl]-Lisoleucyl-3-cyclohexylalanyl-2-oxo-3-aminopentanoyl-N-[(3-nitrophenyl)sulfonyl]glycinamide Step (C4a): Following the procedures analogous to step (A4a), the material from step (C1a) was coupled with -[(3-nitrophenyl)sulfonamide to afford the title product as crystalline solid. MS found (M+1)⁺ 841.3.

Example C5

(4R)-1-[[5-(4-chlorophenyl)-2-furanyl]carbonyl-L-isoleucyl-N-[(1S)-1-(2,2-difluoroethyl)-2,3-dioxo-3-[(2H-tetrazol-5-ylmethyl)amino]propyl]-4-(phenylmethoxy)-L-prolinamide Step (C5a): Following the procedures analogous to steps (A50) and (B1), the title compound was obtained as crystalline solid. MS found (M+1)⁺ 769.3.

Example C6

(2S,4R)-4-(benzyloxy)-N-{(1S)-1-(2,2-difluoroethyl)-2,3-dioxo-3-[(2H-tetraazol-5-ylmethyl)amino]propyl}-1-((2S,3R)-3-methyl-2-{[(9-oxo-9H-fluoren-1-yl)carbonyl]amino}pentanoyl)-2-pyrrolidinecarboxamide Step (C6a): Following the procedures analogous to steps (A50) and (B1), the title compound was obtained as crystalline solid. MS found (M+1)⁺ 771.5.

Example C7 tert-butyl {[(3S)-3-({[(2S,4R)-4-(benzyloxy)-1-((2S,3R)-3-methyl-2-{[(9-oxo-9H-fluoren-1-yl)carbonyl]amino}pentanoyl)pyrrolidinyl]carbonyl}amino)-5,5-difluoro-2-oxopentanoyl]amino}acetate Step (C7a): Following the procedures analogous to steps (A50) and (B1), the title compound was obtained as crystalline solid. MS found (M+1)⁺ 803.4.

Example C8

{[(3S)-3-({[(2S,4R)-4-(benzyloxy)-1-((2S,3R)-3-methyl-2-{[(9-oxo-9H-fluoren-1-yl)carbonyl]amino}pentanoyl)pyrrolidinyl]carbonyl}amino)-5,5-difluoro-2-oxopentanoyl]amino}acetic acid Step (C8a): Following the procedures analogous to steps (A50) and (B1), the title compound was obtained as crystalline solid. MS found (M+1)⁺ 747.3.

Example C9

(2S,4R)-N-[(1S)-3-{[2-({[5-(acetylamino)-1,3,4-thiadiazol-2-yl]sulfonyl}amino)-2-oxoethyl]amino}-1(2,2-difluoroethyl)-2,3-dioxopropyl]-4-(benzyloxy)-1-((2S,3R)-3-methyl-2-{[(9-oxo-9H-fluoren-1-yl)carbonyl]amino}pentanoyl)-2-pyrrolidinecarboxamide Step (C9a): Following the procedures analogous to steps (A50 ) and (B1), the title compound was obtained as crystalline solid. MS found (M+1)⁺ 951.2.

Example C10

(2S,4R)-4-(benzyloxy)-N-((1S)-1-(2,2-difluoroethyl)-3-{[2-({[5-(hexanoylamino)-1,3,4-thiadiazol-2-yl]sulfonyl}amino)-2-oxoethyl]amino}-2,3-dioxopropyl)-1-((2S,3R)-3-methyl-2-{[(9-oxo-9H-fluoren-1-yl)carbonyl]amino}pentanoyl)-2-pyrrolidinecarboxamide Step (C10a): Following the procedures analogous to steps (A50) and (B1), the title compound was obtained as crystalline solid. MS found (M+1)$^+$ 1007.9.

Example C11

((2S,4R)-4-(benzyloxy)-N-[(1S)-3-({2-[({5-[(4-chlorobenzoyl)amino]-1,3,4-thiadiazol-2-yl}sulfonyl)amino]-2-oxoethyl}amino)-1-(2,2-difluoroethyl)-2,3-dioxopropyl]-1-((2S,3R)-3-methyl-2-{[(9-oxo-9H-fluoren-1-yl)carbonyl]amino}pentanoyl)-2-pyrrolidinecarboxamide Step (C11a): Following the procedures analogous to steps (A50) and (B1), the title compound was obtained as crystalline solid. MS found (M+1)$^+$ 1048.3.

Example C12

(2S,4R)-4-(benzyloxy)-N-[(1S)-1-(2,2-difluoroethyl)-3-({2-[({5-[(4-ethylbenzoyl)amino]-1,3,4-thiadiazol-2-yl}sulfonyl)amino]-2-oxoethyl}amino)-2,3-dioxopropyl]-1-((2S,3R)-3-methyl-2-{[(9-oxo-9H-fluoren-1-yl)carbonyl]amino}pentanoyl)-2-pyrrolidinecarboxamide Step (C12a): Following the procedures analogous to steps (A50) and (B1), the title compound was obtained as crystalline solid. MS found (M+1)$^+$ 1041.8.

Example C13 tert-butyl {[(3S)-3-({[(2S,4R)-4-(benzyloxy)-1-((2S,3R)-2-{[5-(4-chlorophenyl)-2-furoyl]amino}-3-methylpentanoyl)pyrrolidinyl]carbonyl}amino)-5,5-difluoro-2-oxopentanoyl]amino}acetate Step (C13a): Following the procedures analogous to steps (A50) and (B1), the title compound was obtained. MS found (M+1)$^+$ 801.9.

Example C14

{[(3S)-3-({[(2S,4R)-4-(benzyloxy)-1-((2S,3R)-2-{[5-(4-chlorophenyl)-2-furoyl]amino}-3-methylpentanoyl)pyrrolidinyl]carbonyl}amino)-5,5-difluoro-2-oxopentanoyl]amino}acetic acid Step (C14a): Following the procedures analogous to steps (A50) and (B1), the title compound was obtained. MS found (M+1)$^+$ 746.0.

Example C15

(2S,4R)-N-[(S)-3-{[2-({[5-(acetylamino)-1,3,4-thiadiazol-2-yl]sulfonyl}amino)-2-oxoethyl]amino}-1-(2,2-difluoroethyl)-2,3-dioxopropyl]-4-(benzyloxy)-1-((2S,3R)-2-{[5-(4-chlorophenyl)-2-furoyl]amino}-3-methylpentanoyl)-2-pyrrolidinecarboxamide Step (C15a): Following the procedures analogous to steps (A50) and (B1), the title compound was obtained. MS found (M+1)$^+$ 950.1.

Example C16

(2S,4R)-4-(benzyloxy)-N-[(1S)-3-({2-[({5-[(3-chlorobenzoyl)amino]-1,3,4-thiadiazol-2-yl}sulfonyl)amino]-2-oxoethyl}amino)-1-(2,2-difluoroethyl)-2,3-dioxopropyl]-1-((2S,3R)-2-{[5-(4-chlorophenyl)-2-furoyl]amino}-3-methylpentanoyl)-2-pyrrolidinecarboxamide Step (C16a): Following the procedures analogous to steps (A50) and (B1), the title compound was obtained. MS found (M+1)$^+$ 1046.7.

Example C17

(2S,4R)-4-(benzyloxy)-N-[(1S)-3-({2-[([1,1'-biphenyl]-3-ylsulfonyl)amino]-2-oxoethyl}amino)-1-(2,2-difluoroethyl)-2,3-dioxopropyl]-1-((2S,3R)-2-{[5-(4-chlorophenyl)-2-furoyl]amino}-3-methylpentanoyl)-2-pyrrolidinecarboxamide Step (C17a): Following the procedures analogous to steps (A50) and (B1), the title compound was obtained. MS found (M+1)$^+$ 961.2.

Example D1

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}-2-pyrazinecarboxamide Step (D1a): The α-hydroxyl β-allyl homoallylglycinamide was prepared according to the following reference disclosed in Han, W. et. al, *Bioorg. & Med. Chem Lett.*, 10, 711–713, 2000, which is hereby incorporated by reference.

(D1b): Tripeptide R-Leu-Ile-Cha-OH was prepared following a procedure analogous to Steps (A2a–h).

(D1c): Following a procedure analogous to Step (A1j), the product from (D1a) and (D1b) was coupled to give the desired α-hydroxyamide.

(D1d): Following a procedure analogous to Step (A2g), the above α-hydroxyamide was converted to the desired product. MS found (M+1)+668.3.

Example D2

(6S,9S,12S)-N,3-diallyl-6-(cyclohexylmethyl)-12-isobutyl-9-[(1R)-1-methylpropyl]-2,5,8,11,14-pentaoxo-16,16-diphenyl-4,7,10,13-tetraazahexadecan-1-amide Step (D2a): Following a procedure analogous to Steps (D1a–d), the title compound was obtained. MS found (M+1)$^+$ 770.9.

Example D3

(4S,7S,10S)-N,13-diallyl-10-(cyclohexylmethyl)-4-isobutyl-7-[(1R)-1-methylpropyl]-2,5,8,11,14-pentaoxo-3,6,9,12-tetraazapentadecan-15-amide Step (D3a): Following a procedure analogous to Steps (D1a–d), the title compound was obtained. MS found (M+1)$^+$ 604.1.

Example D4

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}-2-pyridinecarboxamide Step (D4a): Following a procedure analogous to Steps (D1a–d), the title compound was obtained. MS found (M+1)$^+$ 667.4.

Example D5

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}nicotinamide Step (D5a): Following a procedure analogous to Steps (D1a–d), the title compound was obtained. MS found (M+1)⁺ 667.4.

Example D6

N-{(1S,4S,7S)-10-allyl-7-(cyclohexylmethyl)-1-isobutyl-4-[(1R)-1-methylpropyl]-2,5,8,11,12-pentaoxo-3,6,9,13-tetraazahexadec-15-en-1-yl}-4-nitro-1H-pyrazole-3-carboxamide Step (D6a): Following a procedure analogous to Steps (D1a–d), the title compound was obtained. MS found (M+1)⁺ 701.5.

Example D7

2-{(3S,6S,9S)-12-allyl-9-(cyclohexylmethyl)-3-isobutyl-6-[(1R)-1-methylpropyl]-4,7,10,13,14-pentaoxo-2,5,8,11,15-pentaazaoctadec-17-en-1-anoyl}benzoic acid Step (D7a): Following a procedure analogous to Steps (D1a–d), the title compound was obtained. MS found (M+1)⁺ 710.3.

Example D8

N-[4-sec-butyl-7-(cyclohexylmethyl)-10-ethyl-1-isobutyl-2,5,8,11,12-pentaoxo-3,6,9,13-tetraazahexadec-15-en-1-yl]nicotinamide (D8a): Following a procedure analogous to Step (A1j), the product from (D1b) was coupled with the product from (A1d) to give the desired a-hydroxyester.
(D8b): Following a procedure analogous to Steps (A2e–g), the material from Step (D8a) was converted to the desired product as a white solid (Scheme 6). MS found: (M+1)⁺ 656.4.

Example D9

N-allyl-9-sec-butyl-6-(cyclohexylmethyl)-3-ethyl-12-isobutyl-2,5,8,11,14-pentaoxo-16,16-diphenyl-4,7,10,13-tetraazahexadecan-1-amide Step (D9a): Following a procedure analogous to Step (D8a–b), the title compound was obtained. MS found (M+1)⁺ 758.8.

Example D10

({3-[({1-[3-methyl-2-({4-methyl-2-[(2-pyrazinylcarbonyl)amino]pentanoyl}amino)pentanoyl]-octahydro-1H-indol-2-yl}carbonyl)amino]-2-oxopentanoyl}amino)acetic acid (D10a): The peptide pyrizinecarbonyl-Leu-Ile-octahydroindazole carboxylic acid was prepared following a procedure analogous to Steps (A2a–h).
(D10b): Following a procedure analogous to Steps (A1j–l), the above peptide was coupled with the product from (A1d) and converted to the desired product. MS found (M+1)⁺ 672.4.

Example D11 tert-butyl ({3-[({1-[3-methyl-2-({4-methyl-2-[(2-pyrazinylcarbonyl)amino]pentanoyl}amino)-pentanoyl]octahydro-1H-indol-2-yl}carbonyl)amino]-2-oxopentanoyl}amino)acetate Step (D11a): Following a procedure analogous to Steps (D10a–b), the title compound was obtained. MS found (M+1)⁺ 728.5.

Example D12

(3S,6S,9S,12S)-6-(cyclohexylmethyl)-3-ethyl-12-isobutyl-9-[(1R)-1-methylpropyl]-2,5,8,11,14-pentaoxo-16,16-diphenyl-4,7,10,13-tetraazahexadecan-1-oic acid (D12a): Tripeptide R-Leu-Ile-Cha-OH was prepared following a procedure analogous to Steps (A2a–h).
(D12b): Following a procedure analogous to Step (A1j), the above tripeptide was coupled to the product from (A1d) to give the desired α-hydroxyester.
((D12c): Following a procedure analogous to Steps (A2e) and (A2g), the above material was converted to the desired product. MS found (M+1)⁺ 719.6.

TABLE 1

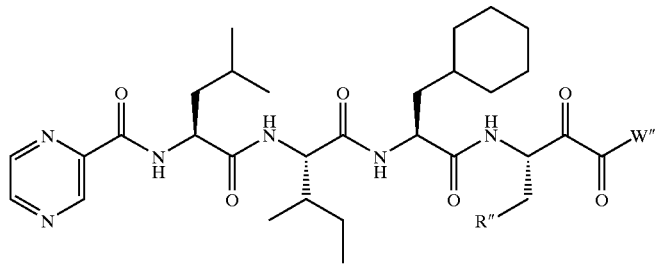

| Ex # | R" | W" | (M + 1) + |
|---|---|---|---|
| A1 | Me | Glycine | 674.4 |
| A2 | Me | 2H-tetrazol-5-yl-methylamino | 698.4 |
| A3 | Me | Sulfonylmethylamino | 710.3 |
| A4 | Me | N-[(3-nitrophenyl)sulfonyl]-glycinamide | 858.3 |
| A5 | Me | N-(methylsulfonyl)glycinamide | 751.4 |
| A6 | Me | N-[(phenylmethyl)sulfonyl]-glycinamide | 825.4 |

TABLE 1-continued

| Ex # | R" | W" | (M + 1) + |
|---|---|---|---|
| A7 | Me | N-(phenylsulfonyl)glycinamide | 813.4 |
| A8 | Me | N-[(trifluoromethyl)sulfonyl]-glycinamide | 805.4 |
| A9 | Me | N-[(2-nitrophenyl)-sulfonyl]glycinamide | 858.1 |
| A10 | Me | N-[(4-nitrophenyl)sulfonyl]-glycinamide | 858.3 |
| A11 | Me | N-[(4-fluorophenyl)sulfonyl]-glycinamide | 831.4 |
| A12 | Me | N-[(3-fluorophenyl)sulfonyl]-glycinamide | 831.4 |
| A13 | Me | N-[(2-fluorophenyl)sulfonyl]-glycinamide | 831.5 |
| A14 | Me | N-[(4-chlorophenyl)sulfonyl]-glycinamide | 848.3 |
| A15 | Me | N-[(3-chlorophenyl)sulfonyl]-glycinamide | 848.4 |
| A16 | Me | N-[[4-(thionitroso)phenyl]sulfonyl]glycinamide | 870.6 |
| A17 | Me | N-[[4-[(trifluoromethyl)sulfonyl]-phenyl]-sulfonyl]glycinamide | 946.1 |
| A18 | Me | N-[[4-(trifluoromethyl)-phenyl]-sulfonyl]-glycinamide | 881.8 |
| A19 | Me | N-[(4-cyanophenyl)sulfonyl]-glycinamide | 839.0 |
| A20 | Me | N-[(3-chloro-4-methylphenyl)-sulfonyl]-glycinamide | 862.3 |
| A21 | Me | N-[(4-chloro-3-nitrophenyl)-sulfonyl]-glycinamide | 893.4 |
| A22 | Me | N-[(3,5-dichlorophenyl)sulfonyl]-glycinamide | 882.9 |
| A23 | Me | N-[(4-methyl-3-nitrophenyl)sulfonyl]-glycinamide | 873.1 |
| A24 | Me | N-[[2-chloro-5-(trifluoromethyl)-phenyl]-sulfonyl]glycinamide | 916.5 |
| A25 | Me | N-[(5-carboxy-2-chlorophenyl)sulfonyl]-glycinamide | 892.3 |
| A26 | Me | N-[(2,5-dichlorophenyl)-sulfonyl]-glycinamide | 879.5 |
| A27 | Me | N-[(3,4-difluorophenyl)-sulfonyl]-glycinamide | 849.6 |
| A28 | Me | N-[(3,5-dichloro-2-hydroxyphenyl)-sulfonyl]-glycinamide | 895.6 (M − 1) − |
| A29 | Me | N-[(2,4,5-trichlorophenyl)sulfonyl]glycinamide | 913.3 (M − 1) − |
| A30 | Me | N-[(5-carboxy-4-chloro-2-fluorophenyl)-sulfonyl]glycinamide | 910.6 |
| A31 | Me | N-[[5-(dimethylamino)-1-naphthalenyl]-sulfonyl]-glycinamide | 907.3 |
| A32 | Me | N-(2-naphthalenylsulfonyl)-glycinamide | 864.2 |
| A33 | Me | N-[(4-(phenyl)phenyl)sulfonyl]glycinamide | 889.5 |
| A34 | Me | N-[(6-ethoxy-2-benzothiazolyl-sulfonyl]-glycinamide | 915.2 |
| A35 | Me | N-[[2-chloro-5-[[(phenylmethyl)-amino]-carbonyl]phenyl]-sulfonyl]glycinamide | 980.6 |
| A36 | Me | N-[[2-chloro-5-[[(2-trifluoroethyl)-amino]carbonyl]-phenyl]-sulfonyl]glycinamide | 970.5 (M − 1) − |
| A37 | Me | N-[[2-chloro-5-[[(cyclopropylmethyl)amino]-carbonyl]phenyl]sulfonyl]glycinamide | 944.4 |
| A38 | Me | N-[[3-nitro-4-(2-pyrimidinylthio)-phenyl]sulfonyl]glycinamide | 968.4 |
| A39 | Me | N-[[2-chloro-4-(acetylamino)-phenyl]sulfonyl]glycinamide | 902.5 (M − 1) − |
| A40 | Me | N-[[3-chloro-4-(2-benzoxazolylthio)phenyl]-sulfonyl]glycinamide | 1005.5 (M − 1) − |
| A41 | Me | N-[[3,5-dichloro-4-(4-nitrophenoxy)phenyl]-sulfonyl]glycinamide | 1018.5 |
| A42 | Me | N-[[5-(acetylamino)-1,3,4-thiadiazol-2-yl]-sulfonyl]-glycinamide | 878.5 |
| A43 | Me | N-[[3-cyanophenyl)-sulfonyl]-glycinamide | 838.4 |
| A44 | Me | N-[[3-(aminosulfonyl)-5-chlorophenyl]-sulfonyl]glycinamide | 924.4 (M − 1) − |
| A45 | Me | N-[[3,5-bis(trifluoromethyl)-phenyl]-sulfonyl]glycinamide | 949.4 |

TABLE 1-continued

| Ex # | R'' | W'' | (M + 1) + |
|---|---|---|---|
| A46 | Me | N-{4-[5-(3-(4-chlorophenyl)-3-oxo-1-propenyl)2-furanyl]-phenyl}sulfonyl glycinamide | 1043.5 |
| A47 | Me | 3{[benzylamino]carbonylphenyl-sulfonyl}-glycinamide | 946.6 |
| A48 | Me | N-[[[[(2-trifluoroethyl)-amino]-carbonyl]phenyl]sulfonyl]-glycinamide | 938.5 |
| A49 | Me | N-[[3-[(benzolamino)-sulfonyl]-5-chlorophenyl]-sulfonyl]glycinamide | 1030.6 |
| A50 | $CHF_2$ | glycine | 710.4 |
| A51 | $CHF_2$ | 2H-tetrazol-5-yl-methylamino | 734.4 |
| A52 | $CHF_2$ | N-[(3,5-dichlorophenyl)-sulfonyl]-glycinamide | 918.9 |
| A53 | $CHF_2$ | N-[(3-chlorophenyl)-sulfonyl]-glycinamide | 883.3 |
| A54 | $CHF_2$ | N-[[5-(acetylamino)-1,3,4-thiadiazol-2-yl]sulfonyl]-glycinamide | 914.5 |
| A55 | $CHF_2$ | N-[3-aminosulfonyl-5-chlorophenyl]sulfonyl-glycinamide | 962.4 |
| A56 | $CF_3$ | 2H-tetrazol-5-yl-methylamino | 752.9 |
| A57 | $CHF_2$ | N-{[(3-chloro-5-{[(3,3,3-trifluoropropanoyl)amino]sulfonyl}phenyl)sulfonyl}glycinamide | 1073.4 |
| A58 | $CHF_2$ | N-[({3-chloro-5-[(hexanoylamino)sulfonyl]phenyl}sulfonyl)}glycinamide | 1061.3 |
| A59 | Me | N-[([1,1'-biphenyl]-3-ylsulfonyl] glycinamide | 890.4 |
| A60 | Me | N-[(4'-methoxy[1,1'-biphenyl]-4-yl)sulfonyl] glycinamide | 920.1 |
| A61 | Me | N-[(3',5'-dichloro[1,1'-biphenyl]-4-yl)sulfonyl]glycinamide | 958.5 |
| A62 | $CHF_2$ | N-[(4'-chloro[1,1'-biphenyl]-3-yl)sulfonyl] glycinamide | 960.6 |
| A63 | $CHF_2$ | N-{4-(2-methylphenoxy)phenyl]sulfonyl} glycinamide | 956.2 |
| A64 | $CHF_2$ | N-{[3-(2-chlorophenoxy)phenyl]sulfonyl} glycinamide | 976.3 |
| A65 | $CHF_2$ | OH | 653.5 |
| A66 | $CHF_2$ | N-[(4'-methyl[1,1'-biphenyl]-3-yl)sulfonyl] glycinamide | 940.1 |
| A67 | $CHF_2$ | N-({[3',5'-bis(trifluoromethyl)[1,1'-biphenyl]-3-yl]sulfonyl} glycinamide | 1061.8 |
| A68 | $CHF_2$ | N-({5-[(4-cyanobenzoyl)amino]-1,3,4-thiadiazol-2-yl}sulfonyl) glycinamide | 1001.9 |
| A69 | $CHF_2$ | N-({5-[(2-chlorobenzoyl)amino]-1,3,4-thiadiazol-2-yl}sulfonyl) glycinamide | 1011.2 |
| A70 | $CHF_2$ | N-({5-[(4-methoxybenzoyl)amino]-1,3,4-thiadiazol-2-yl}sulfonyl) glycinamide | 1006.8 |
| A71 | $CHF_2$ | N-({5-[(3-methoxybenzoyl)amino]-1,3,4-thiadiazol-2-yl}sulfonyl) glycinamide | 1007.1 |
| A72 | $CHF_2$ | N-{5-[(3,5-dimethylbenzoyl)amino]-1,3,4-thiadiazol-2-yl}sulfonyl) glycinamide | 1004.8 |
| A73 | $CHF_2$ | N-[(3-phenoxyphenyl)sulfonyl] glycinamide | 941.8 |
| A74 | Me | OH | 617.4 |
| A75 | $CHF_2$ | N-({5-[(3-methylbutanoyl)amino]-1,3,4-thiadiazol-2-yl}sulfonyl) glycinamide | 957.0 |
| A76 | $CHF_2$ | N-({[5-(hexanoylamino)-1,3,4-thiadiazol-2-yl]sulfonyl glycinamide | 971.0 |
| A77 | $CHF_2$ | methyloxy glycine | 724.4 |
| A78 | Me | N-[(3-chloro-5-{[(3-chlorobenzoyl)amino]sulfonyl glycinamide | 1066.1 |
| A79 | $CHF_2$ | N-{[4'-(trifluoromethyl)[1,1'-biphenyl]-3-yl]sulfonyl]glycinamide | 993.9 |
| A80 | $CHF_2$ | N-[(1,1'-biphenyl]-3-ylsulfonyl] glycinamide | 926.1 |

TABLE 1-continued

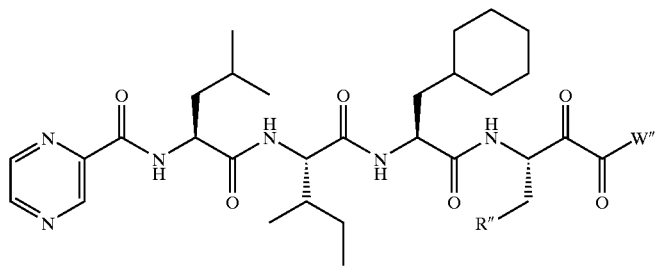

| Ex # | R" | W" | (M + 1) + |
|---|---|---|---|
| A81 | $CHF_2$ | N-({5-[(4-tert-butylbenzoyl)amino]-1,3,4-thiadiazol-2-yl}sulfonyl) glycinamide | 1033.1 |
| A82 | $CHF_2$ | N-[(3-chloro-5-{[(3-methylbutanoyl)amino]sulfonyl}phenyl)sulfonyl] glycinamide | 1047.7 |
| A83 | $CHF_2$ | 4-(4-methoxyphenyl)-5-(trifluoromethyl)-4H-1,2,4-triazol-3-yl-methylamino | 907.8 |
| A84 | $CHF_2$ | N-{[5-[(4-ethylbenzoyl)amino]-1,3,4-thiadiazol-2-yl}sulfonyl) glycinamide | 1005.2 |
| A85 | $CHF_2$ | N-({5-[(4-chlorobenzoyl)amino]-1,3,4-thiadiazol-2-yl}sulfonyl) glycinamide | 1011.5 |
| A86 | $CHF_2$ | N-({5-[(3,5-difluorobenzoyl)amino]-1,3,4-thiadiazol-2-yl}sulfonyl) glycinamide | 1013.1 |
| A87 | $CHF_2$ | N-({5-[(3-chlorobenzoyl)amino]-1,3,4-thiadiazol-2-yl}sulfonyl) glycinamide | 1011.3 |
| A88 | Me | allylamino | 656.4 |
| A89 | Me | propargylamino | 654.5 |
| A90 | Me | t-butyloxy glycine | 730.5 |
| A91 | Me | benzylamino | 706.4 |
| A92 | Me | N-pyrrolidinyl | 670.3 |
| A93 | Me | 1,1,1-trifluoroethylamino | 698.2 |
| A94 | Me | glycinamide | 673.4 |
| A95 | Me | L-alanine | 688.5 |
| A96 | Me | L-aspartic acid | 732.4 |
| A97 | Me | homoglycine | 688.5 |

TABLE 2

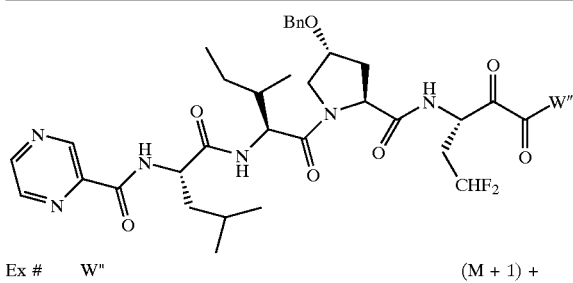

| Ex # | W" | (M + 1) + |
|---|---|---|
| B1 | Tert-butyl glycine | 816.4 |
| B2 | Glycine | 760.3 |
| B3 | Aminomethyltetrazole | 784.4 |
| B4 | Methoxyl | 717.3 |
| B5 | N-[(3-chlorophenyl)-sulfonyl]-glycinamide | 933.3 |
| B6 | N-[(5-carboxy-2-chlorophenyl)-sulfonyl]glycinamide | 978.2 |
| B7 | N-[[5-(acetylamino)-1,3,4-thiadiazol-2-yl]sulfonyl]-glycinamide | 982.5 (M + 1 + $H_2O$) + |
| B8 | N-[(3,5-dichlorophenyl)-sulfonyl]-glycinamide | 967.6 |
| B9 | N-[(4-methyl-3-nitrophenyl)-sulfonyl]glycinamide | 958.4 |
| B10 | N-[(3-carboxyl-4-chloro-2-fluorophenyl)sulfonyl]-glycinamide | 995.4 |
| B11 | N-[[3-chloro-4-(acetylamino)-phenyl]sulfonyl]glycinamide | 1116.5 |

TABLE 2-continued

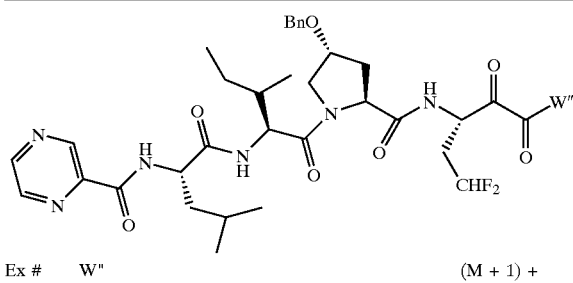

| Ex # | W" | (M + 1) + |
|---|---|---|
| B12 | N-({3-[(benzoylamino)sulfonyl]-5-chlorophenyl]sulfonyl) glycinamide | 1117.4 |
| B13 | Glycine t-Butylester | 788.9 |
| B14 | N-[(3-chloro-4-methylphenyl)sulfonyl] glycinamide | 948.3 |
| B15 | N-({5-[(3-chlorobenzoyl)amino]-1,3,4-thiadiazol-2-yl}sulfonyl) glycinamide | 1061.3 |
| B16 | Glycine methylester | 774.6 |
| B17 | N-[(2,4-dichloro-5-methylphenyl)sulfonyl] glycinamide | 982.6 |
| B18 | N-[(3,4-difluorophenyl)sulfonyl] glycinamide | 935.7 |
| B19 | N-[(3,4-dichlorophenyl)sulfonyl] glycinamide | 1026.7 |
| B20 | N-{[4-(3,5-dimethyl-1-piperidinyl)-3-nitrophenyl]sulfonyl} glycinamide | 1056.0 |
| B21 | N-([3-nitrophenyl) sulfonyl] glycinamide | 944.8 |

TABLE 2-continued

[Chemical structure shown with pyrazine, leucine, isoleucine, BnO-proline, and CHF2 groups with W" substituent]

| Ex # | W" | (M + 1) + |
|---|---|---|
| B22 | N-{[5-(hexanoylamino)-1,3,4-thiadiazol-2-yl]sulfonyl} glycinamide | 1021.1 |
| B23 | N-[(2,4-dichloro-5-carboxylphenyl) sulfonyl] glycinamide | 1012.6 |

TABLE 3

[Chemical structure with $R^9$, $A^2$, $R^1$, W" substituents]

| Ex# | $R^9$ | $A^2$ | $R^1$ | W" | (M + 1) + |
|---|---|---|---|---|---|
| C1 | 4-chlorophenyl-2-furanylcarbonyl | Cha | Et | glycine | 659.4 |
| C2 | 4-chlorophenyl-2-furanylcarbonyl | Cha | Et | N-(trifluoro-methyl-sulfonyl)-glycinamide | 790.3 |
| C3 | 4-chlorophenyl-2-furanylcarbonyl | Cha | Et | N-(3,5-dichloro-phenyl-sulfonyl)-glycinamide | 866.6 |
| C4 | 4-chlorophenyl-2-furanylcarbonyl | Cha | Et | N-(3-nitrophenyl-sulfonyl)glycinamide | 841.3 |
| C5 | 4-chlorophenyl-2-furanylcarbonyl | HyPOBn | $CH_2CHF_2$ | aminomethyl tetrazole | 769.3 |
| C6 | [(9-oxo-9H-fluoren-1-yl)carbonyl | HyPOBn | $CH_2CHF_2$ | 2H-tetrazol-5-yl-methylamino | 771.5 |
| C7 | [(9-oxo-9H-fluoren-1-yl)carbonyl | HyPOBn | $CH_2CHF_2$ | Gly(OtBu) | 803.4 |
| C8 | [(9-oxo-9H-fluoren-1-yl)carbonyl | HyPOBn | $CH_2CHF_2$ | Glycine | 747.3 |
| C9 | [(9-oxo-9H-fluoren-1-yl)carbonyl | HyPOBn | $CH_2CHF_2$ | N-{[5-(acetylamino)-1,3,4-thiadiazol-2-yl]sulfonyl}glycinamide | 951.2 |
| C10 | [(9-oxo-9H-fluoren-1-yl)carbonyl | HyPOBn | $CH_2CHF_2$ | N-{[5-(hexanoylamino)-1,3,4-thiadiazol-2-yl]sulfonyl} glycinamide | 1007.9 |
| C11 | [(9-oxo-9H-fluoren-1-yl)carbonyl | HyPOBn | $CH_2CHF_2$ | N-({5-[(4-chlorobenzoyl)amino]-1,3,4-thiadiazol-2-yl}sulfonyl) glycinamide | 1048.3 |
| C12 | [(9-oxo-9H-fluoren-1-yl)carbonyl | HyPOBn | $CH_2CHF_2$ | N-({2-[({5-[(4-ethylbenzoyl)amino]-1,3,4-thiadiazol-2-yl}sulfonyl) glycinamide | 1041.8 |

TABLE 3-continued

Structure: R⁹-NH-CH(iBu-like)-C(O)-NH-A²-NH-CH(R¹)-C(O)-W″ with O groups

| Ex# | R⁹ | A² | R¹ | W″ | (M + 1)⁺ |
|---|---|---|---|---|---|
| C13 | [(9-oxo-9H-fluoren-1-yl)carbonyl | HyPOBn | CH₂CHF₂ | Gly(OtBu) | 801.9 |
| C14 | [(9-oxo-9H-fluoren-1-yl)carbonyl | HyPOBn | CH₂CHF₂ | Glycine | 746.0 |
| C15 | [(9-oxo-9H-fluoren-1-yl)carbonyl | HyPOBn | CH₂CHF₂ | N-{[5-(acetylamino)-1,3,4-thiadiazol-2-yl]sulfonyl} glycinamide | 950.1 |
| C16 | [(9-oxo-9H-fluoren-1-yl)carbonyl | HyPOBn | CH₂CHF₂ | N-({5-[(3-chlorobenzoyl)amino]-1,3,4-thiadiazol-2-yl}sulfonyl) glycinamide | 1046.7 |
| C17 | [(9-oxo-9H-fluoren-1-yl)carbonyl | HyPOBn | CH₂CHF₂ | N-([1,1'-biphenyl]-3-ylsulfonyl) glycinamide | 961.2 |

TABLE 4

Structure: R⁹-C(O)-NH-CH(iBu)-C(O)-NH-CH(sec-Bu)-C(O)-NH-A²-NH-CH(R″)-C(O)-W″

| EX# | R9 | A2 | R″ | W″ | (M + 1) + |
|---|---|---|---|---|---|
| D1 | Pyrazine carbonyl | Cha | allyl | allylamino | 668.3 |
| D2 | 3,3-diphenyl propionyl | Cha | allyl | allylamino | 770.9 |
| D3 | Acetyl | Cha | allyl | allylamino | 604.1 |
| D4 | 2-pyridine carbonyl | Cha | allyl | allylamino | 667.4 |
| D5 | 3-pyridine carbonyl | Cha | allyl | allylamino | 667.4 |
| D6 | 4-nitropyrazole carbonyl | Cha | allyl | allylamino | 701.5 |
| D7 | 2-carboxyl benzoyl | Cha | allyl | allylamino | 710.3 |
| D8 | 3-pyridine carbonyl | Cha | ethyl | allylamino | 655.4 |
| D9 | 3,3-diphenyl propionyl | Cha | ethyl | allylamino | 758.8 |
| D10 | Pyrazine carbonyl | Octahydro indazole 2-carboxylic acid | ethyl | glycine | 672.4 |
| D11 | Pyrazine carbonyl | Octahydro indazole 2-carboxylic acid | ethyl | Glycine t-butylester | 728.5 |
| D12 | 3,3-diphenyl propionyl | Cha | ethyl | hydroxyl | 719.6 |

The following Table 5 contains representative examples envisioned by the present invention. At the start of each table is one formula followed by species Z1 through Z67 demonstrating the intended substitution of Z; species 1a through 1bw demonstrating the intended substitution of $R^1$; and species 9a through 9n demonstrating the intended substitution of $R^9$. Each entry in each table is intended to be paired with each formula at the start of the table.

For example, Example 100 in Table 5 is intended to be paired with each of formulae Z1, Z2, Z3, Z4, . . . through Z67 of Table 4, as well as each of formulae 1a, 1b, 1c, 1d, . . . through 1bw of Table 4, as well as each of formulae 9a, 9b, 9c, 9d, . . . through 9n of Table 4; thereby representing Example 100-9a-1a-Z1, 100-9a-1a-Z2, 100-9a-1a-Z3, through 243-9n-1bw-Z67.

As an illustration, Example 100-9a-1a-Z1 is N-(2-pyrazinylcarbonyl)-L-leucyl-L-isoleucyl-3-cyclohexylalanyl-2-oxo-3-aminopentanoyl-N-(methylsulfonyl) glycinamide.

TABLE 5

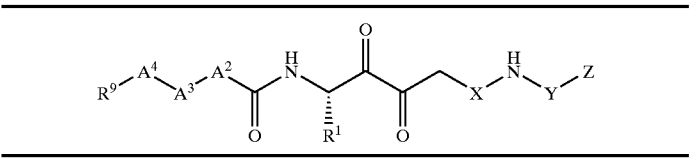

Z is selected from:

- Z1: methyl
- Z2: propyl
- Z3: phenyl
- Z4: 4-phenyl-phenyl
- Z5: 2-fluorophenyl-
- Z6: 4-fluorophenyl-
- Z7: 3-chlorophenyl-
- Z8: 2-cyanophenyl-
- Z9: 4-cyanophenyl-
- Z10: 3-nitrophenyl-
- Z11: 2-$CF_3SO_2$-phenyl-
- Z12: 4-$CF_3SO_2$-phenyl-
- Z13: 3-$CF_3$-phenyl-
- Z14: 3-$NO_2$-4-Cl-phenyl-
- Z15: 2-Cl-5-$CF_3$-phenyl-
- Z16: 3-$NO_2$-4-$CH_3$-phenyl-
- Z17: 3,5-di$CF_3$-phenyl-
- Z18: 3,5-diCl-phenyl-
- Z19: 3,4-diCl-phenyl-
- Z20: 2,5-diF-phenyl-
- Z21: ethyl
- Z22: trifluoromethyl
- Z23: benzyl
- Z24: 4-NCS-phenyl
- Z25: 3-fluorophenyl-
- Z26: 2-chlorophenyl-
- Z27: 4-chlorophenyl-
- Z28: 3-cyanophenyl-
- Z29: 2-nitrophenyl-
- Z30: 4-nitrophenyl-
- Z31: 3-$CF_3SO_2$-phenyl-
- Z32: 2-$CF_3$-phenyl-
- Z33: 4-$CF_3$-phenyl-
- Z34: 3-Cl-4-$CH_3$-phenyl-
- Z35: 2-Cl-5-$CO_2$H-phenyl-
- Z36: 3-Cl-5-$NH_2SO_2$-phenyl-
- Z37: 3,4-di$CF_3$-phenyl-
- Z38: 2,5-diCl-phenyl-
- Z39: 3,5-diF-phenyl-
- Z40: 3,4-diF-phenyl-
- Z41: 2-F-4-Cl-5-$CO_2$H-phenyl-
- Z42: 2,4-diCl-5-$CO_2$H-phenyl-
- Z43: 2,4-diCl-5-$CH_3CO_2$-phenyl-
- Z44: 2,4-diCl-5-$CH_3$-phenyl-
- Z45: 2-OH-3,5-diCl-phenyl-
- Z46: 2,4,5-triCl-phenyl-
- Z47: 3,5-diCl-4-(4-$NO_2$phenyl)phenyl-
- Z48: 2-Cl-5-benzyl-NHCO-phenyl-
- Z49: 2-Cl-5-$CF_3CH_2$-NHCO-phenyl-
- Z50: 2-Cl-5-cyclopropylmethyl-NHCO-phenyl-
- Z51: 2-Cl-4-$CH_3$CONH-phenyl-
- Z52: 5-$CH_3$CONH-1H-pyrrol-2-yl-
- Z53: 5-phenylCONH-furan-2-yl-
- Z54: 2-$CH_3$CONH-2,3-dihydrofuran-5-yl-
- Z55: 3-Cl-5-(phenylCONHSO$_2$)-phenyl-
- Z56: 3-Cl-5-$CH_3$CONH-phenyl-
- Z57: 5-ethoxy-benzothiazol-2-yl
- Z58: naphth-2-yl
- Z59: ($CH_3$CONH)thiadiazolyl-
- Z60: (s-butyl-CONH)-thiadiazolyl-
- Z61: (n-pentyl-CONH)thiadiazolyl-
- Z62: (phenyl-CONH)-thiadiazolyl-
- Z63: (3-Cl-phenyl-CONH)thiadiazolyl-
- Z64: (benzoxazol-2-yl)-
- Z65: (1H-benzimidazol-2-yl)-
- Z66: thiazolo[4,5-c]pyrid-2-yl-
- Z67: 9H-purin-8-yl TABLE 5-continued R¹ is selected from:

| | |
|---|---|
| 1a: | —CH₂CH₃ |
| 1b: | —CH₂CH₂CH₃ |
| 1c: | —CH(CH₃)₂ |
| 1d: | —CH₂CH₂CH₂CH₃ |
| 1e: | —CH₂CH(CH₃)₂ |
| 1f: | —CH₂C(CH₃)₃ |
| 1g: | —CH₂CH₂C(CH₃)₃ |
| 1h: | —CH₂CF₃ |
| 1i: | —CH₂CH₂CF₃ |
| 1j: | —CH₂CH₂CH₂CF₃ |
| 1k: | —CH₂CH=CH₂ |
| 1l: | cis-CH₂CH=CH(CH₃) |
| 1m: | —CH₂CH₂CH=CH |
| 1n: | —CH₂CH₂CH=C(CH₃)₂ |
| 1o: | benzyl |
| 1p: | phenpropyl |
| 1q: | —CH₂CO₂H |
| 1r: | —CH₂CO₂C(CH₃)₃ |
| 1s: | —CH₂CH₂CH₂NH₂ |
| 1t: | (cyclobutyl)methyl- |
| 1u: | (cyclobutyl)propyl- |
| 1v: | cyclobutyl |
| 1w: | cyclohexyl |
| 1x: | (2-methylphenyl)ethyl- |
| 1y: | (3-methylphenyl)ethyl- |
| 1z: | (4-methylphenyl)ethyl- |
| 1aa: | (2-fluorophenyl)ethyl- |
| 1ab: | (3-fluorophenyl)ethyl- |
| 1ac: | (4-fluorophenyl)ethyl- |
| 1ad: | (2-bromophenyl)ethyl- |
| 1ae: | (4-bromophenyl)ethyl- |
| 1af: | (4-phenyl-phenyl)ethyl- |
| 1ag: | (2,4-dimethylphenyl)ethyl- |
| 1ah: | —CH₂CH₂CH₂C(CH₃)₃ |
| 1ai: | —CH₂CH₂CH₂CH(CH₃)₂ |
| 1aj: | —CH₂CH₂CH₂CH(CH₂CH₃)₂ |
| 1ak: | —CH₂CH₂CH₂CH₂CH₃ |
| 1al: | —CH₂CH₂CH(CH₃)₂ |
| 1am: | —CH₂CH₂CH₂CH₂CH₂CH₃ |
| 1an: | —CH₂CHF₂ |
| 1ao: | —CH₂CH₂CHF₂ |
| 1ap: | —CH₂CH₂CH₂CHF₂ |
| 1aq: | —CH=CH₂ |
| 1ar: | —CH=CHCH₃ |
| 1as: | trans-CH₂CH=CH(CH₃) |
| 1at: | —CH₂CH=C(CH₃)₂ |
| 1au: | phenyl |
| 1av: | phenethyl |
| 1aw: | phenbutyl |
| 1ax: | —CH₂CH₂CO₂H |
| 1ay: | —CH₂CH₂CO₂C(CH₃)₃ |
| 1az: | (naphth-2-yl)ethyl- |
| 1ba: | (cyclobutyl)ethyl- |
| 1bb: | cyclopropyl |
| 1bc: | cyclopentyl |
| 1bd: | (4-ethylphenyl)ethyl- |
| 1be: | (4-i-propylphenyl)ethyl- |
| 1bf: | (4-t-butylphenyl)ethyl- |
| 1bg: | (4-hydroxyphenyl)ethyl- |
| 1bh: | (2-chlorophenyl)ethyl- |
| 1bi: | (3-chlorophenyl)ethyl- |
| 1bj: | (4-chlorophenyl)ethyl- |
| 1bk: | (3-bromophenyl)ethyl- |
| 1bm: | (4-phenoxy-phenyl)ethyl- |
| 1bn: | (2,5-dimethylphenyl)ethyl- |
| 1bo: | (2,6-difluorophenyl)ethyl- |
| 1bp: | (4-cyclohexyl-phenyl)ethyl- |
| 1bq: | (4-cyclopentyl-phenyl)ethyl- |
| 1br: | (4-cyclobutyl-phenyl)ethyl- |
| 1bs: | (4-cyclopropyl-phenyl)ethyl- |
| 1bt: | (2-trifluoromethylphenyl)ethyl- |
| 1bu: | (3-trifluoromethylphenyl)ethyl- |
| 1bv: | (4-trifluoromethylphenyl)ethyl- |
| 1bw: | (2,3,4,5,6-pentafluorophenyl)ethyl- |

TABLE 5-continued

R⁹ is selected from:

9a:  2-pyrazinyl-CO—
9b:  4-(N-pyrrolyl)phenyl-CO—
9c:  5-(4-Cl-phenyl)furan-2-yl-CO—
9d:  1-anthracenyl-CO—
9e:  7-NO$_2$-anthracen-1-yl-CO—
9f:  (3-phenyl-2-cyanomethoxyphenyl)-CO—
9g:  5-(2-Cl-3-CF$_3$-phenyl)-furan-2-yl-CO—
9h:  5-(4-Cl-phenyl)-furan-2-yl-CO—
9i:  5-(pyrid-2-yl)-thiophen-2-yl-CO—
9j:  (2-CH$_3$O-phenyl)ethyl-CO—
9k:  (3-benzopyrrolyl)ethyl-CO—
9l:  (N-phenyl-5-propyl-imidazol-4-yl)-CO—
9m: 1-naphthyl-SO$_2$—
9n:  5-(isoxazol-2-yl)-thiophen-2-yl-SO$_2$—

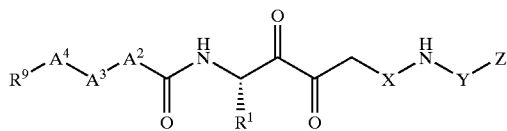

| Ex# | R⁹ | A⁴ | A³ | A² | R¹ | X | Y | Z |
|---|---|---|---|---|---|---|---|---|
| 100 | 9a–9n | Ile | Leu | Cha | 1a–1bw | —(C=O)— | —SO$_2$— | Z1–Z67 |
| 101 | 9a–9n | Val | Leu | Cha | 1a–1bw | —(C=O)— | —SO$_2$— | Z1–Z67 |
| 102 | 9a–9n | Dpa | Leu | Cha | 1a–1bw | —(C=O)— | —SO$_2$— | Z1–Z67 |
| 103 | 9a–9n | Ile | Val | Cha | 1a–1bw | —(C=O)— | —SO$_2$— | Z1–Z67 |
| 104 | 9a–9n | Val | Val | Cha | 1a–1bw | —(C=O)— | —SO$_2$— | Z1–Z67 |
| 105 | 9a–9n | Dpa | Val | Cha | 1a–1bw | —(C=O)— | —SO$_2$— | Z1–Z67 |
| 106 | 9a–9n | Ile | Glu | Cha | 1a–1bw | —(C=O)— | —SO$_2$— | Z1–Z67 |
| 107 | 9a–9n | Val | Glu | Cha | 1a–1bw | —(C=O)— | —SO$_2$— | Z1–Z67 |
| 108 | 9a–9n | Dpa | Glu | Cha | 1a–1bw | —(C=O)— | —SO$_2$— | Z1–Z67 |
| 109 | 9a–9n | Ile | Leu | Hyp | 1a–1bw | —(C=O)— | —SO$_2$— | Z1–Z67 |
| 110 | 9a–9n | Val | Leu | Hyp | 1a–1bw | —(C=O)— | —SO$_2$— | Z1–Z67 |
| 111 | 9a–9n | Dpa | Leu | Hyp | 1a–1bw | —(C=O)— | —SO$_2$— | Z1–Z67 |
| 112 | 9a–9n | Ile | Val | Hyp | 1a–1bw | —(C=O)— | —SO$_2$— | Z1–Z67 |
| 113 | 9a–9n | Val | Val | Hyp | 1a–1bw | —(C=O)— | —SO$_2$— | Z1–Z67 |
| 114 | 9a–9n | Dpa | Val | Hyp | 1a–1bw | —(C=O)— | —SO$_2$— | Z1–Z67 |
| 115 | 9a–9n | Ile | Glu | Hyp | 1a–1bw | —(C=O)— | —SO$_2$— | Z1–Z67 |
| 116 | 9a–9n | Val | Glu | Hyp | 1a–1bw | —(C=O)— | —SO$_2$— | Z1–Z67 |
| 117 | 9a–9n | Dpa | Glu | Hyp | 1a–1bw | —(C=O)— | —SO$_2$— | Z1–Z67 |
| 118 | 9a–9n | Ile | Leu | Pro | 1a–1bw | —(C=O)— | —SO$_2$— | Z1–Z67 |
| 119 | 9a–9n | Val | Leu | Pro | 1a–1bw | —(C=O)— | —SO$_2$— | Z1–Z67 |
| 120 | 9a–9n | Dpa | Leu | Pro | 1a–1bw | —(C=O)— | —SO$_2$— | Z1–Z67 |
| 121 | 9a–9n | Ile | Val | Pro | 1a–1bw | —(C=O)— | —SO$_2$— | Z1–Z67 |
| 122 | 9a–9n | Val | Val | Pro | 1a–1bw | —(C=O)— | —SO$_2$— | Z1–Z67 |
| 123 | 9a–9n | Dpa | Val | Pro | 1a–1bw | —(C=O)— | —SO$_2$— | Z1–Z67 |
| 124 | 9a–9n | Ile | Glu | Pro | 1a–1bw | —(C=O)— | —SO$_2$— | Z1–Z67 |
| 125 | 9a–9n | Val | Glu | Pro | 1a–1bw | —(C=O)— | —SO$_2$— | Z1–Z67 |
| 126 | 9a–9n | Dpa | Glu | Pro | 1a–1bw | —(C=O)— | —SO$_2$— | Z1–Z67 |
| 127 | 9a–9n | bond | Leu | Cha | 1a–1bw | —(C=O)— | —SO$_2$— | Z1–Z67 |
| 128 | 9a–9n | bond | Val | Cha | 1a–1bw | —(C=O)— | —SO$_2$— | Z1–Z67 |
| 129 | 9a–9n | bond | Glu | Cha | 1a–1bw | —(C=O)— | —SO$_2$— | Z1–Z67 |
| 130 | 9a–9n | bond | Leu | Hyp | 1a–1bw | —(C=O)— | —SO$_2$— | Z1–Z67 |
| 131 | 9a–9n | bond | Val | Hyp | 1a–1bw | —(C=O)— | —SO$_2$— | Z1–Z67 |
| 132 | 9a–9n | bond | Glu | Hyp | 1a–1bw | —(C=O)— | —SO$_2$— | Z1–Z67 |
| 133 | 9a–9n | bond | Leu | Pro | 1a–1bw | —(C=O)— | —SO$_2$— | Z1–Z67 |
| 134 | 9a–9n | bond | Val | Pro | 1a–1bw | —(C=O)— | —SO$_2$— | Z1–Z67 |
| 135 | 9a–9n | bond | Glu | Pro | 1a–1bw | —(C=O)— | —SO$_2$— | Z1–Z67 |
| 136 | 9a–9n | Ile | Leu | Cha | 1a–1bw | —SO$_2$— | —(C=O)— | Z1–Z67 |
| 137 | 9a–9n | Val | Leu | Cha | 1a–1bw | —SO$_2$— | —(C=O)— | Z1–Z67 |
| 138 | 9a–9n | Dpa | Leu | Cha | 1a–1bw | —SO$_2$— | —(C=O)— | Z1–Z67 |
| 139 | 9a–9n | Ile | Val | Cha | 1a–1bw | —SO$_2$— | —(C=O)— | Z1–Z67 |
| 140 | 9a–9n | Val | Val | Cha | 1a–1bw | —SO$_2$— | —(C=O)— | Z1–Z67 |
| 141 | 9a–9n | Dpa | Val | Cha | 1a–1bw | —SO$_2$— | —(C=O)— | Z1–Z67 |
| 142 | 9a–9n | Ile | Glu | Cha | 1a–1bw | —SO$_2$— | —(C=O)— | Z1–Z67 |
| 143 | 9a–9n | Val | Glu | Cha | 1a–1bw | —SO$_2$— | —(C=O)— | Z1–Z67 |
| 144 | 9a–9n | Dpa | Glu | Cha | 1a–1bw | —SO$_2$— | —(C=O)— | Z1–Z67 |
| 145 | 9a–9n | Ile | Leu | Hyp | 1a–1bw | —SO$_2$— | —(C=O)— | Z1–Z67 |
| 146 | 9a–9n | Val | Leu | Hyp | 1a–1bw | —SO$_2$— | —(C=O)— | Z1–Z67 |
| 147 | 9a–9n | Dpa | Leu | Hyp | 1a–1bw | —SO$_2$— | —(C=O)— | Z1–Z67 |
| 148 | 9a–9n | Ile | Val | Hyp | 1a–1bw | —SO$_2$— | —(C=O)— | Z1–Z67 |
| 149 | 9a–9n | Val | Val | Hyp | 1a–1bw | —SO$_2$— | —(C=O)— | Z1–Z67 |
| 150 | 9a–9n | Dpa | Val | Hyp | 1a–1bw | —SO$_2$— | —(C=O)— | Z1–Z67 |
| 151 | 9a–9n | Ile | Glu | Hyp | 1a–1bw | —SO$_2$— | —(C=O)— | Z1–Z67 |

TABLE 5-continued

| | | | | | | | | |
|---|---|---|---|---|---|---|---|---|
| 152 | 9a–9n | Val | Glu | Hyp | 1a–1bw | —SO$_2$— | —(C=O)— | Z1–Z67 |
| 153 | 9a–9n | Dpa | Glu | Hyp | 1a–1bw | —SO$_2$— | —(C=O)— | Z1–Z67 |
| 154 | 9a–9n | Ile | Leu | Pro | 1a–1bw | —SO$_2$— | —(C=O)— | Z1–Z67 |
| 155 | 9a–9n | Val | Leu | Pro | 1a–1bw | —SO$_2$— | —(C=O)— | Z1–Z67 |
| 156 | 9a–9n | Dpa | Leu | Pro | 1a–1bw | —SO$_2$— | —(C=O)— | Z1–Z67 |
| 157 | 9a–9n | Ile | Val | Pro | 1a–1bw | —SO$_2$— | —(C=O)— | Z1–Z67 |
| 158 | 9a–9n | Val | Val | Pro | 1a–1bw | —SO$_2$— | —(C=O)— | Z1–Z67 |
| 159 | 9a–9n | Dpa | Val | Pro | 1a–1bw | —SO$_2$— | —(C=O)— | Z1–Z67 |
| 160 | 9a–9n | Ile | Glu | Pro | 1a–1bw | —SO$_2$— | —(C=O)— | Z1–Z67 |
| 161 | 9a–9n | Val | Glu | Pro | 1a–1bw | —SO$_2$— | —(C=O)— | Z1–Z67 |
| 162 | 9a–9n | Dpa | Glu | Pro | 1a–1bw | —SO$_2$— | —(C=O)— | Z1–Z67 |
| 163 | 9a–9n | bond | Leu | Cha | 1a–1bw | —SO$_2$— | —(C=O)— | Z1–Z67 |
| 164 | 9a–9n | bond | Val | Cha | 1a–1bw | —SO$_2$— | —(C=O)— | Z1–Z67 |
| 165 | 9a–9n | bond | Glu | Cha | 1a–1bw | —SO$_2$— | —(C=O)— | Z1–Z67 |
| 166 | 9a–9n | bond | Leu | Hyp | 1a–1bw | —SO$_2$— | —(C=O)— | Z1–Z67 |
| 167 | 9a–9n | bond | Val | Hyp | 1a–1bw | —SO$_2$— | —(C=O)— | Z1–Z67 |
| 168 | 9a–9n | bond | Glu | Hyp | 1a–1bw | —SO$_2$— | —(C=O)— | Z1–Z67 |
| 169 | 9a–9n | bond | Leu | Pro | 1a–1bw | —SO$_2$— | —(C=O)— | Z1–Z67 |
| 170 | 9a–9n | bond | Val | Pro | 1a–1bw | —SO$_2$— | —(C=O)— | Z1–Z67 |
| 171 | 9a–9n | bond | Glu | Pro | 1a–1bw | —SO$_2$— | —(C=O)— | Z1–Z67 |
| 172 | 9a–9n | Ile | Leu | Cha | 1a–1bw | —(C=O)— | —(C=O)— | Z1–Z67 |
| 173 | 9a–9n | Val | Leu | Cha | 1a–1bw | —(C=O)— | —(C=O)— | Z1–Z67 |
| 174 | 9a–9n | Dpa | Leu | Cha | 1a–1bw | —(C=O)— | —(C=O)— | Z1–Z67 |
| 175 | 9a–9n | Ile | Val | Cha | 1a–1bw | —(C=O)— | —(C=O)— | Z1–Z67 |
| 176 | 9a–9n | Val | Val | Cha | 1a–1bw | —(C=O)— | —(C=O)— | Z1–Z67 |
| 177 | 9a–9n | Dpa | Val | Cha | 1a–1bw | —(C=O)— | —(C=O)— | Z1–Z67 |
| 178 | 9a–9n | Ile | Glu | Cha | 1a–1bw | —(C=O)— | —(C=O)— | Z1–Z67 |
| 179 | 9a–9n | Val | Glu | Cha | 1a–1bw | —(C=O)— | —(C=O)— | Z1–Z67 |
| 180 | 9a–9n | Dpa | Glu | Cha | 1a–1bw | —(C=O)— | —(C=O)— | Z1–Z67 |
| 181 | 9a–9n | Ile | Leu | Hyp | 1a–1bw | —(C=O)— | —(C=O)— | Z1–Z67 |
| 182 | 9a–9n | Val | Leu | Hyp | 1a–1bw | —(C=O)— | —(C=O)— | Z1–Z67 |
| 183 | 9a–9n | Dpa | Leu | Hyp | 1a–1bw | —(C=O)— | —(C=O)— | Z1–Z67 |
| 184 | 9a-9n | Ile | Val | Hyp | 1a–1bw | —(C=O)— | —(C=O)— | Z1–Z67 |
| 185 | 9a–9n | Val | Val | Hyp | 1a–1bw | —(C=O)— | —(C=O)— | Z1–Z67 |
| 186 | 9a–9n | Dpa | Val | Hyp | 1a–1bw | —(C=O)— | —(C=O)— | Z1–Z67 |
| 187 | 9a–9n | Ile | Glu | Hyp | 1a–1bw | —(C=O)— | —(C=O)— | Z1–Z67 |
| 188 | 9a–9n | Val | Glu | Hyp | 1a–1bw | —(C=O)— | —(C=O)— | Z1–Z67 |
| 189 | 9a–9n | Dpa | Glu | Hyp | 1a–1bw | —(C=O)— | —(C=O)— | Z1–Z67 |
| 190 | 9a–9n | Ile | Leu | Pro | 1a–1bw | —(C=O)— | —(C=O)— | Z1–Z67 |
| 191 | 9a–9n | Val | Leu | Pro | 1a–1bw | —(C=O)— | —(C=O)— | Z1–Z67 |
| 192 | 9a–9n | Dpa | Leu | Pro | 1a–1bw | —(C=O)— | —(C=O)— | Z1–Z67 |
| 193 | 9a–9n | Ile | Val | Pro | 1a–1bw | —(C=O)— | —(C=O)— | Z1–Z67 |
| 194 | 9a–9n | Val | Val | Pro | 1a–1bw | —(C=O)— | —(C=O)— | Z1–Z67 |
| 195 | 9a–9n | Dpa | Val | Pro | 1a–1bw | —(C=O)— | —(C=O)— | Z1–Z67 |
| 196 | 9a–9n | Ile | Glu | Pro | 1a–1bw | —(C=O)— | —(C=O)— | Z1–Z67 |
| 197 | 9a–9n | Val | Glu | Pro | 1a–1bw | —(C=O)— | —(C=O)— | Z1–Z67 |
| 198 | 9a–9n | Dpa | Glu | Pro | 1a–1bw | —(C=O)— | —(C=O)— | Z1–Z67 |
| 199 | 9a–9n | bond | Leu | Cha | 1a–1bw | —(C=O)— | —(C=O)— | Z1–Z67 |
| 200 | 9a–9n | bond | Val | Cha | 1a–1bw | —(C=O)— | —(C=O)— | Z1–Z67 |
| 201 | 9a–9n | bond | Glu | Cha | 1a–1bw | —(C=O)— | —(C=O)— | Z1–Z67 |
| 202 | 9a–9n | bond | Leu | Hyp | 1a–1bw | —(C=O)— | —(C=O)— | Z1–Z67 |
| 203 | 9a–9n | bond | Val | Hyp | 1a–1bw | —(C=O)— | —(C=O)— | Z1–Z67 |
| 204 | 9a–9n | bond | Glu | Hyp | 1a–1bw | —(C=O)— | —(C=O)— | Z1–Z67 |
| 205 | 9a–9n | bond | Leu | Pro | 1a–1bw | —(C=O)— | —(C=O)— | Z1–Z67 |
| 206 | 9a–9n | bond | Val | Pro | 1a–1bw | —(C=O)— | —(C=O)— | Z1–Z67 |
| 207 | 9a–9n | bond | Glu | Pro | 1a–1bw | —(C=O)— | —(C=O)— | Z1–Z67 |
| 208 | 9a–9n | Ile | Leu | Cha | 1a–1bw | —SO$_2$— | —SO$_2$— | Z1–Z67 |
| 209 | 9a–9n | Val | Leu | Cha | 1a–1bw | —SO$_2$— | —SO$_2$— | Z1–Z67 |
| 210 | 9a–9n | Dpa | Leu | Cha | 1a–1bw | —SO$_2$— | —SO$_2$— | Z1–Z67 |
| 211 | 9a–9n | Ile | Val | Cha | 1a–1bw | —SO$_2$— | —SO$_2$— | Z1–Z67 |
| 212 | 9a–9n | Val | Val | Cha | 1a–1bw | —SO$_2$— | —SO$_2$— | Z1–Z67 |
| 213 | 9a–9n | Dpa | Val | Cha | 1a–1bw | —SO$_2$— | —SO$_2$— | Z1–Z67 |
| 214 | 9a–9n | Ile | Glu | Cha | 1a–1bw | —SO$_2$— | —SO$_2$— | Z1–Z67 |
| 215 | 9a–9n | Val | Glu | Cha | 1a–1bw | —SO$_2$— | —SO$_2$— | Z1–Z67 |
| 216 | 9a–9n | Dpa | Glu | Cha | 1a–1bw | —SO$_2$— | —SO$_2$— | Z1–Z67 |
| 217 | 9a–9n | Ile | Leu | Hyp | 1a–1bw | —SO$_2$— | —SO$_2$— | Z1–Z67 |
| 218 | 9a–9n | Val | Leu | Hyp | 1a–1bw | —SO$_2$— | —SO$_2$— | Z1–Z67 |
| 219 | 9a–9n | Dpa | Leu | Hyp | 1a–1bw | —SO$_2$— | —SO$_2$— | Z1–Z67 |
| 220 | 9a–9n | Ile | Val | Hyp | 1a–1bw | —SO$_2$— | —SO$_2$— | Z1–Z67 |
| 221 | 9a–9n | Val | Val | Hyp | 1a–1bw | —SO$_2$— | —SO$_2$— | Z1–Z67 |
| 222 | 9a–9n | Dpa | Val | Hyp | 1a–1bw | —SO$_2$— | —SO$_2$— | Z1–Z67 |
| 223 | 9a–9n | Ile | Glu | Hyp | 1a–1bw | —SO$_2$— | —SO$_2$— | Z1–Z67 |
| 224 | 9a–9n | Val | Glu | Hyp | 1a–1bw | —SO$_2$— | —SO$_2$— | Z1–Z67 |
| 225 | 9a–9n | Dpa | Glu | Hyp | 1a–1bw | —SO$_2$— | —SO$_2$— | Z1–Z67 |
| 226 | 9a–9n | Ile | Leu | Pro | 1a–1bw | —SO$_2$— | —SO$_2$— | Z1–Z67 |
| 227 | 9a–9n | Val | Leu | Pro | 1a–1bw | —SO$_2$— | —SO$_2$— | Z1–Z67 |
| 228 | 9a–9n | Dpa | Leu | Pro | 1a–1bw | —SO$_2$— | —SO$_2$— | Z1–Z67 |
| 229 | 9a–9n | Ile | Val | Pro | 1a–1bw | —SO$_2$— | —SO$_2$— | Z1–Z67 |
| 230 | 9a–9n | Val | Val | Pro | 1a–1bw | —SO$_2$— | —SO$_2$— | Z1–Z67 |

TABLE 5-continued

| | | | | | | | |
|---|---|---|---|---|---|---|---|
| 231 | 9a–9n | Dpa | Val | Pro | 1a–1bw —$SO_2$— | —$SO_2$— | Z1–Z67 |
| 232 | 9a–9n | Ile | Glu | Pro | 1a–1bw —$SO_2$— | —$SO_2$— | Z1–Z67 |
| 233 | 9a–9n | Val | Glu | Pro | 1a–1bw —$SO_2$— | —$SO_2$— | Z1–Z67 |
| 234 | 9a–9n | Dpa | Glu | Pro | 1a–1bw —$SO_2$— | —$SO_2$— | Z1–Z67 |
| 235 | 9a–9n | bond | Leu | Cha | 1a–1bw —$SO_2$— | —$SO_2$— | Z1–Z67 |
| 236 | 9a–9n | bond | Val | Cha | 1a–1bw —$SO_2$— | —$SO_2$— | Z1–Z67 |
| 237 | 9a–9n | bond | Glu | Cha | 1a–1bw —$SO_2$— | —$SO_2$— | Z1–Z67 |
| 238 | 9a–9n | bond | Leu | Hyp | 1a–1bw —$SO_2$— | —$SO_2$— | Z1–Z67 |
| 239 | 9a–9n | bond | Val | Hyp | 1a–1bw —$SO_2$— | —$SO_2$— | Z1–Z67 |
| 240 | 9a–9n | bond | Glu | Hyp | 1a–1bw —$SO_2$— | —$SO_2$— | Z1–Z67 |
| 241 | 9a–9n | bond | Leu | Pro | 1a–1bw —$SO_2$— | —$SO_2$— | Z1–Z67 |
| 242 | 9a–9n | bond | Val | Pro | 1a–1bw —$SO_2$— | —$SO_2$— | Z1–Z67 |
| 243 | 9a–9n | bond | Glu | Pro | 1a–1bw —$SO_2$— | —$SO_2$— | Z1–Z67 |

Utility

The compounds of Formula (I) are expected to inhibit the activity of Hepatitis C Virus NS3 protease. The NS3 protease inhibition is demonstrated using assays for NS3 protease activity, for example, using the assay described below for assaying inhibitors of NS3 protease. The compounds of Formula (I) are expected to show activity against NS3 protease in cells, as demonstrated by the cellular assay described below. Thus, the compounds of Formula (I) are potentially useful in the cure and prevention of HCV infections.

Expression and Purification of NS3 Protease

The plasmid cf1SODp600, containing the complete coding region of HCV NS3 protease, genotype 1a, was obtained from ATCC (database accession: DNA Seq. Acc. M62321, originally deposited by Chiron Corporation). PCR primers were designed that allow amplification of the DNA fragment encoding the NS3 protease catalytic domain (amino acids 1 to 192) as well as its two N-terminal fusions, a 5 amino acid leader sequence MGAQH (SEQ. ID. NO.:1) (serving as a expression tag) and a 15 amino acid His tag MRGSHHH-HHHMGAQH. (SEQ. ID. NO.:2). The NS3 protease constructs were cloned in the bacterial expression vector under the control of the T7 promoter and transformed in E. coli BL 21 (DE3) cells. Expression of the NS3 protease was obtained by addition of 1 mM IPTG and cells were growing for additional 3 h at 25° C. The NS3 protease constructs have several fold difference in expression level, but exhibit the same level of solubility and enzyme specific activity. A typical 10 L fermentation yielded approximately 200 g of wet cell paste. The cell paste was stored at −80° C. The NS3 protease was purified based on published procedures (Steinkuhler C. et al. *Journal of Virology* 70, 6694–6700, 1996 and Steinkuhler C. et al. *Journal of Biological Chemistry* 271, 6367–6373, 1996.) with some modifications. Briefly, the cells were resuspended in lysis buffer (10 mL/g) containing PBS buffer (20 mM sodium phosphate, pH 7.4, 140 mM NaCl), 50% glycerol, 10 mM DTT, 2% CHAPS and 1 mM PMSF. Cell lysis was performed with use of microfluidizer. After homogenizing, DNase was added to a final concentration 70 U/mL and cell lysate was incubated at 4° C. for 20 min. After centrifugation at 18,000 rpm for 30 min at 4° C. supernatant was applied on SP Sepharose column (Pharmacia), previously equilibrated at a flow rate 3 mL/min in buffer A (PBS buffer, 10% glycerol, 3 mM DTT). The column was extensively washed with buffer A and the protease was eluted by applying 25 column volumes of a linear 0.14–1.0 M NaCl gradient. NS3 containing fractions were pooled and concentrated on an Amicon stirred ultrafiltration cell using a YM-10 membrane. The enzyme was further purified on 26/60 Superdex 75 column (Pharmacia), equilibrated in buffer A. The sample was loaded at a flow rate 1 mL/min, the column was then washed with a buffer A at a flow rate 2 mL/min. Finally, the NS3 protease containing fractions were applied on Mono S 10/10 column (Pharmacia) equilibrated in 50 mM Tris.HCl buffer, pH 7.5, 10% glycerol and 1 mM DTT and operating at flow rate 2 mL/min. Enzyme was eluted by applying 20 column volumes of a linear 0.1–0.5 M NaCl gradient. Based on SDS-PAGE analysis as well as HPLC analysis and active site titration, the purity of the HCV NS3 1a protease was greater than 95%. The enzyme was stored at −70° C. and diluted just prior to use.

Enzyme Assays

Concentrations of protease were determined in the absence of NS4a by using the peptide ester substrate Ac-DED(Edans)EEAbuΨ[COO]ASK(Dabcyl)-$NH_2$ (SEQ. ID. NO.:3) (Taliani et al. *Anal. Biochem.* 240, 60–67, 1996.) and the inhibitor, H-Asp-Glu-Val-Val-Pro-boroAlg-OH (SEQ. ID. NO.:5) and by using tight binding reaction conditions (Bieth, *Methods Enzymol.* 248, 59–85, 1995). Best data was obtained for an enzyme level of 50 nM. Alternately, protease (63 μg/mL) was allowed to react with 3 μM NS4a, 0.10 mM Ac-Glu-Glu-Ala-CyS-pNA (SEQ. ID. NO.:4), and varying level of H-Asp-Glu-Val-Val-Pro-boroAlg-OH (0–6 μM). Concentrations of protease were determined from linear plots of Activity vs. [inhibitor]. Molar concentrations of proteases were determined from the x-intercept. $K_m$ values were determined measuring the rate of hydrolysis of the ester substrate over a range of concentrations from 5.0 to 100 μM in the presence of 3 μM KKNS4a (KKGSVVIVGRIVLSGKPAIIPKK) (SEQ. ID. NO.:6). Assay were run at 25° C., by incubating ~1 nM enzyme with NS4a for 5 mm in 148 μl of buffer (50 mM Tri buffer, pH 7.0, 50% glycerol, 2% Chaps, and 5.0 mM DTT. Substrate (2.0 μl) in buffer was added and the reaction was allowed to proceed for 15 min. Reactions were quenched by adding 3.0 μL of 10% TFA, and the levels of hydrolysis were determined by HPLC. Aliquots (50 μL) were injected on the HPLC and linear gradients from 90% water, 10% acetonitrile and 0.10% TFA to 10% water, 90% acetonitrile and 0.10% TFA were run at a flow rate of 1.0 mL/min over a period of 30 mm. HPLCs were run on a HP1090using a Rainin 4.6×250 mm C18 column (cat # 83-201-C) fluorescent detection using 350 and 500 nm as excitation and emission wavelengths, respectively. Levels of hydrolysis were determined by measuring the area of the fluorescent peak at 5.3 min. 100% hydrolysis of a 5.0 μM sample gave an area of 7.95±0.38 fluorescence units.). Kinetic constants were determined from the iterative fit of the Michaelis equation to the data. Results are consistent with data from Liveweaver Burk fits and data collected for the 12.8 min peak measured at 520 nm.

Enzyme activity was also measured by measuring the increase in fluorescence with time by exciting at 355 nm and measuring emission at 495 nm using a Perkin Elmer LS 50 spectrometer. A substrate level of 5.0 $\mu$M was used for all fluorogenic assays run on the spectrometer.

Inhibitor Evaluation In Vitro

Inhibitor effectiveness was determined by measuring enzyme activity both in the presence and absence of inhibitor. Velocities were fit to the equation for competitive inhibition for individual reactions of inhibitors with the enzyme using $$v_i/v_o=[K_m(1+I/K_i)+S]/[K_m+S].$$

The ratio $v_i/v_o$ is equal to the ratio of the Michaelis equations for velocities measured in the presence ($v_i$) and absence ($v_o$) of inhibitor. Values of $v_i/v_o$ were measured over a range of inhibitor concentrations with the aid of an Excel™ Spreadsheet. Reported $K_i$ values are the average of 3–5 separate determinations. Under the conditions of this assay, the $IC_{50}$ and $K_i$s are comparable measures of inhibitor effectiveness.

Using the methodology described above, compounds of the present invention were found to exhibit a $K_i$ of $\leq 60$ $\mu$M, thereby confirming the utility of the compounds of the present invention as effective NS3 protease inhibitors. Preferred compounds of the present invention have $K_i$'s of $\leq 1$ $\mu$M. More preferred compounds of the present invention have $K_i$'s of $\leq 100$ $\mu$M. Most preferred compounds of the present invention have $K_i$'s of $\leq 10$ nM.

Inhibitor Evaluation in Cell Assay.

The following method was devised to assess inhibitory action of test compounds on the HCV NS3 protease in cultured cells. Because it is not possible to efficiently infect cells with hepatitis C virus, an assay was developed based on co-expression in transfected cell lines of two plasmids, one is able to direct synthesis of the NS3 protease and the other to provide a polypeptide analogous to a part of the HCV non-structural protein containing a single known peptide sequence highly susceptible to cleavage by the protease. When installed in cultured cells by one of a variety of standard methods, the substrate plasmid produces a stable polypeptide of approximately 50 KD, but when the plasmid coding for the viral protease is co-expressed, the enzymatic action of the protease hydrolyzes the substrate at a unique sequence between a cysteine and a serine pair, yielding products which can be detected by antibody-based technology, eg, a western blot. Quantitation of the amounts of precursor and products can be done by scanning film auto-radiograms of the blots or direct luminescense-based emissions from the blots in a commercial scanning device. The general organization of the two plasmids is provided in Scheme 6. The coding sequences for the NS3 protease and the substrate were taken from genotype 1a of HCV, but other genotypes, eg 2a, may be substituted with similar results.

The DNA plasmids are introduced into cultured cells using electroporation, liposomes or other means. Synthesis of the protease and the substrate begin shortly after introduction and may be detected within a few hours by immunological means. Therefore, test compounds are added at desired concentrations to the cells within a few minutes after introducing the plasmids. The cells are then placed in a standard $CO_2$ incubator at 37° C., in tissue culture medium eg Dulbecco-modified MEM containing 10% bovine serum. After 6–48 hours, the cells are collected by physically scraping them from plastic dishes in which they have been growing, centrifuging them and then lysing about $10^6$ of the concentrated cells in a minimal volume of buffered detergent, eg 20 $\mu$l of 1% sodium dodecyl sulfate in 0.10 M Tris-HCl, pH 6.5, containing 1% mercaptaethanol and 7% glycerol. The samples are then loaded onto a standard SDS polyacrylamide gel, the polypeptides separated by electrophoresis, and the gel contents then electroblotted onto nitrocellulose or other suitable paper support, and the substrate and products detected by decoration with specific antibodies.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

Preparation of H-Asp-Glu-Val-Val-Pro-boroAlg Pinanediol Ester.Trifluoroacetate (SEQ. ID. NO.:7).

Preparation of Boc-Asp(O$^t$Bu)-Glu(O$^t$Bu)-Val-Val-Pro-OH. (SEQ. ID. NO.:8.

Boc-Val-Pro-OBzl was prepared by dissolving H-Pro-OBzl (20 g, 83 mmol) in 50 mL of chloroform and adding Boc-Val-OH (18.0 g, 83 mmol), HOBt (23.0 g, 165 mmol), NMM (9.0 mL, 83 mmol) and DCC (17.0 g, 83 mmol). The reaction mixture was stirred overnight at room temperature. The mixture was filtered and solvent was evaporated. Ethyl acetate was added and insoluble material was removed by filtration. The filtrate was washed with 0.2N HCl, 5% NaHCO$_3$, and saturated aqueous NaCl. It was dried over Na$_2$SO$_4$, filtered and evaporate to give a white solid (30 g, 75 mmol, 90%). ESI/MS calculated for $C_{22}H_{32}N_2O_5$+H: 405.2. Found 405.6.

Boc-Val-Val-Pro-OBzl was prepared by dissolving Boc-Val-Pro-OBzl (14.0 g, 35.0 mmol) in 4N HCl in dioxane (20 mL) and allowing the reaction to stir for 2 h under an inert atmosphere at room temperature. The reaction mixture was concentrated by evaporation in vacuo and ether was added to yield a precipitate. It was collected by filtration under nitrogen. After drying in vacuo with P$_2$O$_5$, H-Val-Pro-OBzl was obtained as a white solid (22.6 g, 30.3 mmol, 89%). (ESI/MS calculated for $C_{17}H_{24}N_2O_3$+H: 305.2. Found: 305.2.) H-Val-Pro-OBzl (9.2 g, 27 mmol) was dissolved in 50 mL of CH$_2$Cl$_2$ and Boc-Val-OH (7.3 g, 27 mmol), HOBt (7.3 g, 54 mmol), NMM (3.0 mL, 27 mmol) and DCC (5.6 g, 27 mmol) were added. The reaction mixture stirred overnight at room temperature. The mixture was filtered and the filtrate was evaporated. The residue was dissolved in ethyl acetate and the solution was re-filtered. The filtrate was washed with 0.2N HCl, 5% NaHCO$_3$, and saturated aqueous NaCl. It was dried over Na$_2$SO$_4$, filtered and evaporated to give a yellow oil (10.6 g, 21.1 mmol, 78%). ESI/MS calculated for $C_{27}H_{41}N_3O_6$+Na: 526.3 Found: 526.4.

Z-Glu(O$^t$Bu)-Val-Val-Pro-OBzl (SEQ. ID. NO.:9) was also prepared by DCC coupling. H-Val-Val-Pro-OBzl.hydrochloride was obtained in a 100% yield by treating the corresponding Boc compound with anhydrous HCl using the procedure described for H-Val-Pro-OBzl (ESI/MS calculated for $C_{22}H_{33}N_3O_4$+H: 404.2. Found 404.3.). The amine hydrochloride (7.40 g, 16.8 mmol) was dissolved in 185 mL DMF and 25 mL THF. Z-Glu(O$^t$Bu)-OH (5.60 g, 16.8 mmol), HOBt (4.60 g, 33.6 mmol), NMM (1.85 mL, 16.8 mmol) and DCC (3.5 g, 16.8 mmol) were added. The reaction was run and the product was isolated by the procedure described for Boc-Val-Val-Pro-OBzl. The tetrapeptide was obtained as a white foam (12.0 g, 16.1 mmol, 96%). ESI/MS calculated for $C_{39}H_{54}N_4O_9$+Na: 745.4. Found: 745.4.

H-Glu(O$^t$Bu)-Val-Val-Pro-OH (SEQ. ID. NO.:10) was prepared by dissolving Z-Glu(O$^t$Bu)-Val-Val-Pro-OBzl (2.90 g, 3.89 mmol) in 100 mL methanol containing 1% acetic acid. Pearlman's catalyst, Pd(OH)$_2$, (100 mg) was added and the flask was placed on the Parr hydrogenation apparatus with an initial H$_2$ pressure of 34 psi. After three hours, the catalyst was removed by filtration through a celite pad and the filtrate was evaporated in vacuo to yield a yellow oil (1.30 g, 2.61 mmol, 67%). ESI/MS calculated for $C_{24}H_{42}N_4O_7$+H: 499.3 Found: 499.4.

Boc-Asp(O′Bu)-Glu(O′Bu)-Val-Val-Pro-OH was prepared by active ester coupling. Boc-Asp(O′Bu)-N-hydroxysuccinimide ester was prepared by coupling Boc-Asp(OtBu)-OH (3.00 g, 10.4 mmol) to N-hydroxysuccinimide (1.19 g, 10.4 mmol) in 50 mL of ethylene glycol dimethyl ether. The reaction flask was placed in an ice bath at 0° C. and DCC was added.

The reaction mixture was slowly allowed to warm to room temperature and to stir overnight. The mixture was filtered and the filtrate was evaporated in vacuo. The residue was dissolved in ethyl acetate and re-filtered. The filtrate was evaporated give a white solid. Recrystallized from ethyl acetate: hexane gave the activated ester (3.38 g, 8.80 mmol, 84%). (ESI/MS calculated for $C_{17}H_{26}N_2O_8$+H: 387.2. Found: 387.4.) H-Glu(O′Bu)-Val-Val-Pro-OH (5.40 g, 10.8 mmol) was dissolved in 100 mL of water. Sodium bicarbonate (0.92 g, 11.0 mmol) was added followed by triethylamine (2.30 mL, 16.5 mmol). The N-hydroxysuccinimide ester (3.84 g, 10.0 mmol) was dissolved in 100 mL dioxane and was added to the H-Glu(O′Bu)-Val-Val-Pro-OH solution. The mixture stirred overnight at room temperature. Dioxane was removed in vacuo and 1.0 M HCl was added to give pH ~1. The product was extracted into ethyl acetate. The ethyl acetate solution was washed with 0.2 N HCl, dried over sodium sulfate, filtered, and evaporated to yield a yellow oil (7.7 g, 10.0 mmol, 100%). ESI/MS calculated for $C_{37}H_{63}N_5O_{12}$+Na: 792.4. Found: 792.4.

Boc-Asp(O′Bu)-Glu(O′Bu)-Val-Val-Pro-boroAlg-pinanediol (SEQ. ID. NO.:11) was prepared by coupling the protected pentapeptide to H-boroAlg-pinanediol. Boc-Asp(O′Bu)-Glu(O′Bu)-Val-Val-Pro-OH (1.8 g, 2.3 mmol) was dissolved 10 mL THF and was cooled to −20° C. Isobutyl chloroformate (0.30 mL, 2.3 mmol) and NMM (0.25 mL, 2.3 mmol) were added. After 5 minutes, this mixture was added to H-boroAlg-pinanediol (0.67 g, 2.3 mmol) dissolved in THF (8 mL) at −20° C. Cold THF (~5 mL) was used to aid in the transfer. Triethylamine (0.32 mL, 2.3 mmol) was added and the reaction mixture was allowed to come to room temperature and to stir overnight. The mixture was filtered and solvent was removed by evaporation. The residue was dissolved in ethyl acetate, washed with 0.2 N HCl, 5% NaHCO$_3$, and saturated NaCl. The organic phase was dried with Na$_2$SO$_4$, filtered, and evaporated to yield a yellow oil. Half of the crude product (1.5 g) was purified in 250 mg lots by HPLC using a 4 cm×30 cm Rainin C-18 reverse phase column. A gradient from 60: 40 acetonitrile: water to 100% acetonitrile was run over a period of 28 minutes at a flow rate of 40 mL/min. The fractions containing the desired product were pooled and lyophilized to yield a white solid (46 mg). $^1$H-NMR (CD$_3$OD) δ 0.9–1.0 (m, 15H), 1.28 (s, 3H), 1.3 (s,3H), 1.44(3s, 27H), 1.6–2.8 (20H), 3.7(m,1H), 3.9(m, 1H), 4.1–4.7 (7H), 5.05(m, 2H), 5.9(m, 1H). High res (ESI/MS) calculated for $C_{51}H_{86}N_6O_{13}B1$ +H: 1001.635. Found 1001.633.

Preparation of H—Asp-Glu-Val-Val-Pro-boroAlg pinanediol ester.trifluoroacetate: The hexapeptide analog, Boc-Asp(O′Bu)-Glu(O′Bu)-Val-Val-Pro-boroAlg-pinanediol, (22.5 mg, 0.023 mmol) was treated with 2 mL of TFA: CH$_2$Cl$_2$ (1:1) for 2 h. The material was concentrated in vacuo and purified by HPLC using C-18 Vydac reverse phase (2.2×25 cm) column with a gradient starting at 60:40 acetonitrile/water with 0.1%TFA going to 95:5 over 25 minutes with a flow rate of 8 mL/min. The product eluted at 80% acetonitrile. The fractions were evaporated and dried under high vacuum to give 8.9 mg (49%) of the desired product as white amorphous solid. $^1$H-NMR (CD$_3$OD) δ 5.82 (m, 1H), 5.02 (m, 2H), 4.58(m, 1H), 4.42 (m, 3H), 4.18 (m, 4H), 3.90 (m, 1H), 3.62 (m, 1H), 3.01 (dd, 1H), 2.78 (m, 1H), 2.62 (m, 1H), 2.41–1.78 (m, 17H), 1.31 (s, 3H), 1.28 (s, 3H), 1.10–0.82 (m, 15H). ESI/MS calculated for $C_{38}H_{62}N_6O_{11}B$ +H: 789.2. Found: 789.2.

What is claimed:

1. A compound of Formula (III):

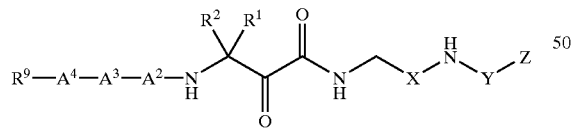

(III)

or a stereoisomer or pharmaceutically acceptable salt form thereof, wherein;

$R^{11}$ is, at each occurrence, independently H or $C_1$–$C_4$ alkyl;

X is —C(=O)—, —S—, —S(=O)—, or —S(=O)$_2$—;

Y is —C(=O)—or —S(=O)$_2$—;

Z is $C_1$–$C_4$ haloalkyl,
$C_1$–$C_4$ alkyl substituted with 0–3 $Z^a$,
$C_2$–$C_4$ alkenyl substituted with 0–3 $Z^a$,
$C_2$–$C_4$ alkynyl substituted with 0–3 $Z^a$,
$C_3$–$C_{10}$ cycloalkyl substituted with 0–5 $Z^b$,
$C_3$–$C_{10}$ carbocycle substituted with 0–5 $Z^b$,
aryl substituted with 0–5 $Z^b$, or
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; said heterocyclic group substituted with 0–4 $Z^b$;

$Z^a$ is H, F, Cl, Br, I, —NO$_2$, —CN, —NCS, —CF$_3$, —OCF$_3$, —CH$_3$, —OCH$_3$, —CO$_2$R$^{20}$, —C(=O) NR$^{20}$R$^{20}$, —NHC(=O)R$^{20}$, —NR$^{20}$R$^{20}$,

—OR$^{20}$, —SR$^{20}$, —S(=O)R$^{20}$, —SO$_2$R$^{20}$,
—SO$_2$NR$^{20}$R$^{20}$, C$_1$–C$_4$ alkyl, C$_1$–C$_4$ alkoxy, C$_1$–C$_4$ haloalkyl, C$_1$–C$_4$ haloalkoxy,
C$_3$–C$_{10}$ cycloalkyl substituted with 0–5 Z$^b$,
C$_3$–C$_{10}$ carbocycle substituted with 0 5 Z$^b$,
aryl substituted with 0–5 Z$^b$, or
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; said heterocyclic group substituted with 0–4 Z$^b$;

Z$^b$ is H, F, Cl , Br, I, —NO$_2$, —CN, —NCS, —CF$_3$, —OCF$_3$, —CH$_3$, —OCH$_3$, —CO$_2$R$^{20}$, —C(=O) NR$^{20}$R$^{20}$, —NHCO(=O)R$^{20}$, —NR$^{20}$R$^{20}$,
—OR$^{20}$, —SR$^{20}$, —S(=O)R$^{20}$, —SO$_2$R$^{20}$,
—SO$_2$NR$^{20}$R$^{20}$, C$_1$–C$_4$ alkyl, C$_1$–C$_4$ alkoxy, C$_1$–C$_4$ haloalkyl, C$_1$–C$_4$ haloalkoxy,
C$_3$–C$_{10}$ cycloalkyl substituted with 0–5 Z$^c$,
C$_3$–C$_{10}$ carbocycle substituted with 0–5 Z$^c$,
aryl substituted with 0–5 Z$^c$, or
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolirlyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; said heterocyclic group substituted with 0–4 Z$^c$;

Z$^c$ is H, F, Cl, Br, I, —NO$_2$, —CN, —NCS, —CF$_3$, —OCF$_3$, —CH$_3$, —OCH$_3$, —CO$_2$R$^{20}$, —C(=O) NR$^{20}$R$^{20}$, —NHC(=O)R$^{20}$, —NR$^{20}$R$^{20}$,
—OR$^{20}$, —SR$^{20}$, —S(=O)R$^{20}$, —SO$_2$R$^{20}$,
—SO$_2$NR$^{20}$R$^{20}$, C$_1$–C$_4$ alkyl, C$_1$–C$_4$ alkoxy, C$_1$–C$_4$ haloalkyl, C$_1$–C$_4$ haloalkoxy;

R$^{20}$ is H, C$_1$–C$_4$ alkyl, C$_1$–C$_4$ haloalkyl, aryl, aryl(C$_1$–C$_4$ alkyl)-, C$_3$–C$_6$ cycloalkyl, or C$_3$–C$_6$ cycloalkyl(C$_1$–C$_4$ alkyl)-;

alternatively, NR$^{20}$R$^{20}$ may form a piperidinyl, piperazinyl, or morpholinyl group;

A$^2$ is a bond, —NH—CR$^3$R$^4$—C(=O)—, Ala, Arg, Asn, Asp, Aze, Cha, Cys, Dpa, Gln, Glu, Gly, His, Hyp, Ile,
Irg, Leu, Lys, Met, Orn, Phe, Phe(4-fluoro), Pro, Sar, Ser, Thr, Trp, Tyr, Val,

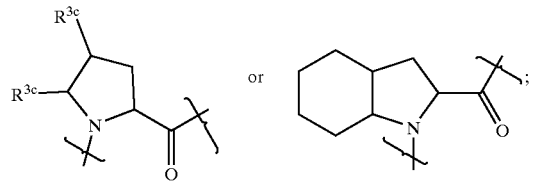

A$^3$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

A$^4$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

R$^1$ is selected from the group: H,
C$_1$–C$_6$ alkyl substituted with 0–3 R$^{1a}$,
C$_2$–C$_6$ alkenyl substituted with 0–3 R$^{1a}$,
C$_2$–C$_6$ alkynyl substituted with 0–3 R$^{1a}$, and
C$_3$–C$_6$ cycloalkyl substituted with 0–3 R$^{1a}$;

R$^{1a}$ is selected at each occurrence from the group:
Cl, F, Br, I, CF$_3$, CHF$_2$, OH, =O, SH,
—CO$_2$R$^{1b}$, —SO$_2$R$^{1b}$, —SO$_3$R$^{1b}$, —P(O)$_2$R$^{1b}$, —P(O)$_3$R$^{1b}$,
—C(=O)NHR$^{1b}$, —NHC(=O)R$^{1b}$, —SO$_2$NHR$^{1b}$, OR$^{1b}$, —SR$^{1b}$,
C$_1$–C$_3$ alkyl, C$_3$–C$_6$ cycloalkyl, C$_1$–C$_6$ alkoxy,
—S—(C$_1$–C$_6$ alkyl),
aryl substituted with 0–5 R$^{1c}$,
—O—(CH$_2$)$_q$-aryl substituted with 0–5 R$^{1c}$,
—S—(CH$_2$)$_q$-aryl substituted with 0–5 R$^{1c}$,
5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and substituted with 0–3 R$^{1c}$;

R$^{1b}$ is H,
C$_1$–C$_4$ alkyl substituted with 0–3 R$^{1c}$,
C$_2$–C$_4$ alkenyl substituted with 0–3 R$^{1c}$,
C$_2$–C$_4$ alkynyl substituted with 0–3 R$^{1c}$,
C$_3$–C$_6$ cycloalkyl substituted with 0–5 R$^{1c}$,
C$_3$–C$_6$ carbocycle substituted with 0–5 R$^{1c}$,
aryl substituted with 0–5 R$^{1c}$, or
5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group substituted with 0–3 R$^{1c}$;

$R^{1c}$ is selected at each occurrence from: $C_1$–$C_4$ alkyl, Cl, F, Br, I, OH, $C_1$–$C_4$ alkoxy, —CN, —NO$_2$, C(O)OR$^{1d}$, NR$^{1d}$R$^{1d}$, CF$_3$, and OCF$_3$;

$R^{1d}$ is H or $C_1$–$C_4$ alkyl;

$R^2$ is H or $C_1$–$C_4$ alkyl;

alternatively, $R^1$ and $R^2$ combine to form a $C_3$–$C_6$ cycloalkyl group substituted with 0–3 $R^{1c}$;

$R^3$ is selected from the group: H,
- $C_1$–$C_6$ alkyl substituted with 0–4 $R^{3a}$,
- $C_2$–$C_6$ alkenyl substituted with 0–4 $R^{3a}$,
- $C_2$–$C_6$ alkynyl substituted with 0–4 $R^{3a}$,
- —(CH$_2$)$_q$—$C_3$–$C_6$ cycloalkyl substituted with 0–4 $R^{3b}$,
- —(CH$_2$)$_q$-aryl substituted with 0–5 $R^{3b}$,
- —(CH$_2$)$_q$-5–10 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and said heterocyclic group is substituted with 0–2 $R^{3b}$;

$R^{3a}$ is selected from the group: —CO$_2$R$^{11}$, —NR$^{11}$R$^{11}$, —OR$^{11}$, —SR$^{11}$, —C(=NH)NH$_2$, and aryl substituted with R$^{10b}$;

$R^{3b}$ is selected from the group: —CO$_2$H, —NH$_2$, —OH, —SH, and —C(=NH)NH$_2$;

$R^{3c}$ is, at each occurrence, independently selected from H, $C_1$–$C_6$ alkyl, —OH, or OR$^{3d}$;

$R^{3d}$ is $C_1$–$C_6$ alkyl, $C_2$–$C_6$ alkenyl, $C_2$–$C_6$ alkynyl, —(CH$_2$)$_q$— $C_3$–$C_6$ cycloalkyl, —(CH$_2$)$_q$-aryl, or —(CH$_2$)$_q$-(5–10 membered heterocyclic group), wherein said heterocyclic group consists of carbon atoms and 1–4 heteroatoms selected from the group: O, S, and N;

$R^4$ is selected from the group H, $C_1$–$C_6$ alkyl, phenyl, phenylmethyl-, phenylethyl-, $C_3$–$C_6$ cycloalkyl, $C_3$–$C_6$ cycloalkylmethyl-, and $C_3$–$C_6$ cycloalkylethyl-;

$R^9$ is selected from —S(=O)$_2$R$^{9a}$ and —C(=O)R$^{9a}$;

$R^{9a}$ is selected from the group:
- phenyl substituted with 0–3 $R^{9c}$,
- naphthyl substituted with 0–3 $R^{9c}$, and
- 5–14 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl; and said heterocyclic group is substituted with 0–3 $R^{9c}$;

$R^{9c}$ is selected at each occurrence from the group:
  CF$_3$, OCF$_3$, Cl, F, Br, I, =O, OH, phenyl, C(O)OR$^{11}$, NB$_2$, NH(CH$_3$), N(CH$_3$)$_2$, —CN, NO$_2$;
  $C_1$–$C_4$ alkyl substituted with 0–3 $R^{9d}$,
  $C_1$–$C_4$ alkoxy substituted with 0–3 $R^{9d}$,
  $C_3$–$C_6$ cycloalkyl substituted with 0–3 $R^{9d}$,
  aryl substituted with 0–5 $R^{9d}$, and
  5–6 membered heterocyclic group consisting of carbon atoms and 1–4 heteroatoms selected from the group: pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl; said heterocyclic group is substituted with 0–4 $R^{9d}$;

$R^{9d}$ is selected at each occurrence from the group:
  $C_1$–$C_4$ alkyl, $C_1$–$C_4$ alkoxy, CF$_3$, OCF$_3$, Cl, F, Br, I, =O, OH, phenyl, C(O)OR$^{11}$, NH$_2$, NH(CH$_3$), N(CH$_3$)$_2$, —CN, and NO$_2$;

p is 1 or 2; and q, at each occurence, is independently 0, 1 or 2.

2. A compound of claim 1, wherein x is —C(=O)—;

Y is —S(=O)$_2$—;

Z is selected from the group:
  methyl, ethyl, propyl, trifluoromethyl,
  phenyl, benzyl, 4-phenyl-phenyl, 4-NCS-phenyl,
  2-fluorophenyl-, 3-fluorophenyl-, 4-fluorophenyl-,
  2-chlorophenyl-, 3-chlorophenyl-, 4-chlorophenyl-,
  2-cyanophenyl-, 3-cyanophenyl-, 4-cyanophenyl-,
  2-nitrophenyl-, 3-nitrophenyl-, 4-nitrophenyl-,
  2-CF$_3$SO$_2$-phenyl-, 3-CF$_3$SO$_2$-phenyl-, 4-CF$_3$SO$_2$-phenyl-,
  2-CF$_3$-phenyl-, 3-CF$_3$-phenyl-, 4-CF$_3$-phenyl-,
  3-NO$_2$-4-Cl-phenyl-, 3-Cl-4-CH$_3$-phenyl-,
  2-Cl-5-CF$_3$-phenyl-, 2–Cl-5-CO$_2$H-phenyl-,
  3-NO$_2$-4-CH$_3$-phenyl-, 3-Cl-5-NH$_2$SO$_2$-phenyl-,
  3,5-diCF$_3$-phenyl-, 3,4-diCF$_3$-phenyl-,
  3,5-diCl-phenyl-, 2,5-diCl-phenyl-, 3,4-diCl-phenyl-,
  3,5-diF-phenyl-, 2,5-diF-phenyl-, 3,4-diF-phenyl-,
  2-F-4-Cl-5-CO$_2$H-phenyl-, 2,4-diCl-5-CO$_2$H-phenyl-,
  2,4-diCl-5-CH$_3$CO$_2$-phenyl-, 2,4-diCl-5-CH$_3$-phenyl-,
  2-OH-3,5-diCl-phenyl-, 2,4,5-triCl -phenyl-,
  3,5-diCl-4-(4-NO$_2$phenyl)phenyl-,
  2-Cl-5-benzylNHCO-phenyl-, 2–Cl-5-CF$_3$CH$_2$NHCO-phenyl-,
  2–Cl-5-cyclopropylmethylNHCO-phenyl-,
  2–Cl-4-CH$_3$CONH-phenyl-, 3-Cl-5-(phenylCONHSO$_2$)-phenyl-,
  3-Cl-5-CH$_3$CONH-phenyl-, 5-ethoxy-benzothiazol-2-yl,
  naphth-2-yl, (CH$_3$CONH)thiadiazolyl-,
  (s-butylCONH)thiadiazolyl-, (n-pentylCONH)thiadiazolyl-,
  (phenylCONH)thiadiazolyl-, and
  (3-ClphenylCONH)thiadiazolyl-, $A^2$ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, Val;

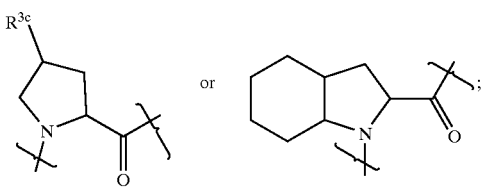

A³ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

A³ is a bond, Ala, Arg, Asn, Asp, Aze, Cha, Cys, Dpa, Gln, Glu, Gly, His, Hyp, Ile, Irg, Leu, Lys, Met, Orn, Phe, Phe(4-fluoro), Pro, Sar, Ser, Thr, Trp, Tyr, or Val;

R¹ is selected from the group:
—$CH_2CH_3$, —$CH_2CH_2CH_3$, —$CH(CH_3)_2$, —$CH_2CH_2CH_3$,
—$CH_2CH(CH_3)_2$, —$CH_2C(CH_3)_3$, —$CH_2CH_2C(CH_3)_3$,
—$CH_2CH_2CH_2C(CH_3)_3$, —$CH_2CH_2CH_2CH(CH_3)_2$,
—$CH_2CH_2CH_2CH(CH_2CH_3)_2$,
-$CH_2CH_2CH_2CH_2CH_3$,
—$CH_2CH_2CH(CH_3)_2$, —$CH_2CH_2CH_2CH_2CH_2CH_3$,
—$CH_2CF_3$, —$CH_2CH_2CF_3$, —$CH_2CH_2CH_2CF_3$,
—$CH_2CHF_2$, —$CH_2CH_2CHF_2$, —$CH_2CH_2CH_2CHF_2$,
—$CH=CH_2$, —$CH_2CH=CH_2$, —$CH=CHCH_3$, cis-$CH_2CH=CH(CH_3)$,
trans-$CH_2CH=CH(CH_3)$, —$CH_2CH_2CH=CH$,
—$CH_2CH=C(CH_3)_2$,
—$CH_2CH_2CH=C(CH_3)_2$,
—$CH_2CO_2H$, —$CH_2CH_2CO_2H$, —$CH_2CO_2C(CH_3)_3$,
—$CH_2CH_2CO_2C(CH_3)_3$, —$CH_2CH_2CH_2CH_2NH_2$,
phenyl, benzyl, phenethyl, phenpropyl, phenbutyl,
(2-methylphenyl)ethyl-, (3-methylphenyl)ethyl-,
(4-methylphenyl)ethyl-, (4-ethylphenyl)ethyl-,
(4-i-propylphenyl)ethyl-, (4-t-butylphenyl)ethyl-,
(4-hydroxyphenyl)ethyl-, (4-phenyl-phenyl)ethyl-,
(4-phenoxy-phenyl)ethyl-, (4-cyclohexyl-phenyl) ethyl-,
(4-cyclopropyl-phenyl)ethyl-, (2,5-dimethylphenyl) ethyl-,
(2,4-dimethylphenyl)ethyl-, (2,6-difluorophenyl) ethyl-,
(4-cyclopentyl-phenyl)ethyl-,
(4-cyclobutyl-phenyl)ethyl-,
(2-trifluoromethylphenyl)ethyl-,
(3-trifluoromethylphenyl)ethyl-,
(4-trifluoromethylphenyl)ethyl-,
(2-fluorophenyl)ethyl-, (3-fluorophenyl)ethyl-,
(4-fluorophenyl)ethyl-, (2-chlorophenyl)ethyl-,
(3-chlorophenyl)ethyl-, (4-chlorophenyl)ethyl-,
(2-bromophenyl)ethyl-, (3-bromophenyl)ethyl-,
(4-bromophenyl)ethyl-,
(2,3,4,5,6-pentafluorophenyl)ethyl-,
(naphth-2-yl)ethyl, (cyclobutyl)methyl,
(cyclobutyl)ethyl, (cyclobutyl)propyl, cyclopropyl,
cyclobutyl, cyclopentyl, and cyclohexyl;

R² is H, methyl, or ethyl;
alternatively, R¹ and R² combine to form cyclopropyl, cyclobutyl, cyclopentyl, or cyclohexyl;

R³ᶜ is H, methyl, ethyl, —OH, methoxy, ethoxy, propoxy, phenoxy, or benzyloxy; and R⁹ is selected from:
2-pyrazinyl-carbonyl-,
4-(N-pyrrolyl)phenyl-carbonyl-,
5-(4-chlorophenyl)furan-2-yl-carbonyl-,
1-anthracenyl-carbonyl-,
7-nitro-anthracen-1-yl-carbonyl-,
(3-phenyl-2-cyanomethoxyphenyl)carbonyl-,
5-(2-Cl-3-CF₃-phenyl)-furan-2-yl-carbonyl-,
5-(4-Cl-phenyl)-furan-2-yl-carbonyl-,
5-(pyrid-2-yl)-thiophen-2-yl-carbonyl-,
(2-methoxyphenyl)ethylcarbonyl-,
(3-benzopyrrolyl)ethylcarbonyl-,
(N-phenyl-5-propyl-imidazol-4-yl)-carbonyl-,
1-naphthyl-sulphonyl-, and
5-(isoxazol-2-yl)thiophen-2-yl-sulphonyl-.

3. A compound according to claim 1, selected from the group consisting of 2-oxo-3-[[N-(2-pyrazinylcarbonyl)-L-leucyl-L-isoleucyl-3-cyclohexylalanyl]amino]-N-(sulfomethyl)pentanamide;

N-(2-pyrazinylcarbonyl)-L-leucyl-L-isoleucyl-3-cyclohexylalanyl-2-oxo-3-aminopentanoyl-N-[(2-nitrophenyl) sulfonyl]glycinamide;

N-(2-pyrazinylcarbonyl)-L-leucyl-L-isoleucyl-3-cyclohexylalanyl-2-oxo-3-aminopentanoyl-N-(methylsulfonyl) glycinamide;

N-(2-pyrazinylcarbonyl)-L-leucyl-L-isoleucyl-3-cyclohexylalanyl-2-oxo-3-aminopentanoyl-N-[(phenylmethyl) sulfonyl]glycinamide;

N-(2-pyrazinylcarbonyl)-L-leucyl-L-isoleucyl-3-cyclohexylalanyl-2-oxo-3-aminopentanoyl-N-(phenylsulfonyl) glycinamide;

N-(2-pyrazinylcarbonyl)-L-leucyl-L-isoleucyl-3-cyclohexylalanyl-2-oxo-3-aminopentanoyl-N-[(trifluoromethyl) sulfonyl]glycinamide;

N-(2-pyrazinylcarbonyl)-L-leucyl-L-isoleucyl-3-cyclohexylalanyl-2-oxo-3-aminopentanoyl-N-[(2-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[(4-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[(4-fluorophenyl)sulfonyl]glycinamide;

N-(2-pyrazinylcarbonyl)-L-leucyl-L-isoleucyl-3-cyclohexyl-L-alanyl-2-oxo-(3 S)-3-amino pentanoyl-N-[(3-fluorophenyl)sulfonyl]glycinamide;

N-(2-pyrazinylcarbonyl)-L-leucyl-L-isoleucyl-3-cyclohexylalanyl-2-oxo-3-aminopentanoyl-N-[(2-fluorophenyl) sulfonyl]glycinamide;

N-(2-pyrazinylcarbonyl)-L-leucyl-L-isoleucyl-3-cyclohexylalanyl-2-oxo-3-aminopentanoyl-N-[(4-chlorophenyl) sulfonyl]glycinamide;

N-(2-pyrazinylcarbonyl)-L-leucyl-L-isoleucyl-3-cyclohexylalanyl-2-oxo-3-aminopentano yl-N-[(3-chlorophenyl) sulfonyl]glycinamide;

N-(2-pyrazinylcarbonyl)-L-leucyl-L-isoleucyl-3-cyclohexylalanyl-2-oxo-3-aminopentanoyl-N-[[4-(thionitroso) phenyl]sulfonyl]glycinamide;

N-(2-pyrazinylcarbonyl)-L-leucyl-L-isoleucyl-3-cyclohexylalanyl-2-oxo-3-aminopentanoyl-N-[[4-[(trifluoromethyl) sulfonyl]phenyl]sulfonyl] glycinamide;

N-(2-pyrazinylcarbonyl)-L-leucyl-L-isoleucyl-3-cyclohexylalanyl-2-oxo-3-aminopentanoyl-N-[[4-(trifluoromethyl)phenyl]sulfonyl]glycinamide;

N-(2-pyrazinylcarbonyl)-L-leucyl-L-isoleucyl-3-cyclohexylalanyl-2-oxo-3-aminopentanoyl-N-[(4-cyanophenyl)sulfonyl]glycinamide;

N-(2-pyrazinylcarbonyl)-L-leucyl-L-isoleucyl-3-cyclohexylalanyl-2-oxo-3-aminopentanoyl-N-[(3-chloro-4-methylphenyl)sulfonyl]glycinamide;

N-(2-pyrazinylcarbonyl)-L-leucyl-L-isoleucyl-3-cyclohexylalanyl-2-oxo-3-aminopentanoyl-N-[(4-chloro-3-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[(3,5-dichlorophenyl)sulfonyl]glycinamide;

N-(2-pyrazinylcarbonyl)-L-leucyl-L-isoleucyl-3-cyclohexylalanyl-2-oxo-3-aminopentanoyl-N-[(4-methyl-3-nitrophenyl)sulfonyl]glycinamide;

N-(2-pyrazinylcarbonyl)-L-leucyl-L-isoleucyl-3-cyclohexylalanyl-2-oxo-3-aminopentanoyl-N-[[2-chloro-5-(trifluoromethyl)phenyl]sulfonyl]glycinamide;

N-(2-pyrazinylcarbonyl)-L-leucyl-L-isoleucyl-3-cyclohexylalanyl-2-oxo-3-aminopentanoyl-N-[(5-carboxy-2-chlorophenyl)sulfonyl]glycinamide;

N-(2-pyrazinylcarbonyl)-L-leucyl-L-isoleucyl-3-cyclohexylalanyl-2-oxo-3-aminopentanoyl-N-[(2,5-dichlorophenyl)sulfonyl]glycinamide;

N-(2-pyrazinylcarbonyl)-L-leucyl-L-isoleucyl-3-cyclohexylalanyl-2-oxo-3-aminopentanoyl-N-[(3,4-difluorophenyl)sulfonyl]glycinamide;

N-(2-pyrazinylcarbonyl)-L-leucyl-L-isoleucyl-3-cyclohexylalanyl-2-oxo-3-aminopentanoyl-N-[(3,5-dichloro-2-hydroxyphenyl)sulfonyl]glycinamide;

N-(2-pyrazinylcarbonyl)-L-leucyl-L-isoleucyl-3-cyclohexyl-L-alanyl-2-oxo-(3S)-3-amino pentanoyl-N-[(2,4,5-trichlorophenyl)-sulfonyl]glycinamide;

N-(2-pyrazinylcarbonyl)-L-leucyl-L-isoleucyl-3-cyclohexylalanyl-2-oxo-3-aminopentanoyl-N-[(5-carboxy-4-chloro-2-fluorophenyl)sulfonyl]glycinamide;

N-(2-pyrazinylcarbonyl)-L-leucyl-L-isoleucyl-3-cyclohexylalanyl-2-oxo-3-aminopentanoyl-N-[[5-(dimethylamino)-1-naphthalenyl]sulfonyl]glycinamide;

N-(2-pyrazinylcarbonyl)-L-leucyl-L-isoleucyl-3-cyclohexylalanyl-2-oxo-3-aminopentanoyl-N-(2-naphthalenylsulfonyl)glycinamide;

N-(2-pyrazinylcarbonyl)-L-leucyl-L-isoleucyl-3-cyclohexyl-L-alanyl-2-oxo-(3S)-3-aminopentanoyl-N-[(4-(phenyl)phenyl)-sulfonyl]glycinamide;

N-(2-pyrazinylcarbonyl)-L-leucyl-L-isoleucyl-3-cyclohexylalanyl-2-oxo-3-aminopentanoyl-N-[(6-ethoxy-2-benzothiazolyl)sulfonyl]glycinamide;

N-(2-pyrazinylcarbonyl)-L-leucyl-L-isoleucyl-3-cyclohexylalanyl-2-oxo-3-aminopentanoyl-N-[[2-chloro-5-[[(phenylmethyl)amino]carbonyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[2-chloro-5-[[(2-trifluoroethyl)amino]carbonyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[2-chloro-5-[[(cyclopropylmethyl)amino]carbonyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-nitro-4-(2-pyrimidinylthio)phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[2-chloro-4-(acetylamino)phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-chloro-4-(2-benzoxazolylthio)phenyl]sulfonyl]glycinamide;

N-(2-pyrazinylcarbonyl)-L-leucyl-L-isoleucyl-3-cyclohexyl-L-alanyl-2-oxo-(3 S)-3-amino pentanoyl-N-[[3,5-dichloro-4-(4-nitrophenoxy)phenyl]sulfonyl]glycinamide;

N-(2-pyrazinylcarbonyl)-L-leucyl-L-isoleucyl-3-cyclohexyl-L-alanyl-2-oxo-(3 S)-3-amino pentanoyl-N-[[5-(acetylamino)-1,3,4-thiadiazol-2-yl]sulfonyl]glycinamide;

N-(2-pyrazinylcarbonyl)-L-leucyl-L-isoleucyl-3-cyclohexyl-L-alanyl-2-oxo-(3 S)-3-amino pentanoyl-N-[(3-cyanophenyl)sulfonyl]glycinamide;

N-(2-pyrazinylcarbonyl)-L-leucyl-L-isoleucyl-3-cyclohexyl-L-alanyl-2-oxo-(3 S)-3-amino pentanoyl-N-[[3-(aminosulfonyl)-5-chlorophenyl]sulfonyl]glycinamide;

N-(2-pyrazinylcarbonyl)-L-leucyl-L-isoleucyl-3-cyclohexyl-L-alanyl-2-oxo-(3S)-3-amino pentanoyl-N-[[3,5-bis(trifluoromethyl)phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[4-[5-[3-(4-chlorophenyl)-3-oxo-1-propenyl]-2-furanyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-[[(phenylmethyl)amino]carbonyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-[[(2,2,2-trifluoroethyl)amino]carbonyl]phenyl]sulfonyl]glycinamide;

N-(2-pyrazinylcarbonyl)-L-leucyl-L-isoleucyl-3-cyclohexyl-L-alanyl-2-oxo-(3S)-3-aminopentanoyl-N-[[3-[(benzoylamino)sulfonyl]-5-chlorophenyl]sulfonyl]glycinamide;

N-(2-pyrazinylcarbonyl)-L-leucyl-L-isoleucyl-3-cyclohexyl-L-alanyl-5,5-difluoro-2-oxo-(3S)-3-aminopentanoyl-N-[(3,5-dichlorophenyl)sulfonyl]glycinamide;

N-(2-pyrazinylcarbonyl)-L-leucyl-L-isoleucyl-3-cyclohexyl-L-alanyl-5,5-difluoro-2-oxo-(3S)-3-aminopentanoyl-N-[(3-chlorophenyl)sulfonyl]glycinamide;

N-(2-pyrazinylcarbonyl)-L-leucyl-L-isoleucyl-3-cyclohexyl-L-alanyl-5,5-difluoro-2-oxo-(3S)-3-aminopentanoyl-N-[5-(acetylamino)-1,3,4-thiadiazol-2-yl]sulfonyl]-glycinamide;

N-(2-pyrazinylcarbonyl)-L-leucyl-L-isoleucyl-3-cyclohexyl-L-alanyl-5,5-difluoro-2-oxo-(3S)-3-aminopentanoyl-N-(3-aminosulfonyl-5-chlorophenyl)sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(3-chlorophenyl)sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3- aminopentanoyl-N-[(5-carboxy-2-chlorophenyl)-sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[(5-acetylamino)1,3,4-thiadiazol-2-yl)sulfonyl]glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl-N-[3,5-dichlorophenyl) sulfonyl] glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-(4-methyl-3-nitrophenyl) sulfonyl]-glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-(3-carboxyl-4-chloro-2-fluorophenyl) sulfonyl]-glycinamide;

N-(2-pyrazinylcarbonyl)-L-leucyl-L-isoleucyl-(4R)-4-(phenylmethoxy)-L-prolyl-5,5-difluoro-2-oxo-(3S)-3-aminopentanoyl N-[(3-chloro-4-acetylamino)phenyl] sulfonyl]-glycinamide;

N-[[5-(4-chlorophenyl)-2-furanyl]carbonyl]-Lisoleucyl-3-cyclohexylalanyl-2-oxo-3-aminopentanoyl-N-[(trifluoromethyl)sulfonyl]glycinamide;

N-[[5-(4-chlorophenyl)-2-furanyl]carbonyl]-Lisoleucyl-3-cyclohexylalanyl-2-oxo-3-aminopentanoyl-N-[(3,5-dichlorophenyl)sulfonyl]glycinamide;

N-[[5-(4-chlorophenyl)-2-furanyl]carbonyl]-Lisoleucyl-3-cyclohexylalanyl-2-oxo-3-aminopentanoyl-N-[(3-nitrophenyl)sulfonyl]glycinamide;

or a pharmaceutically acceptable salt form thereof.

4. A composition comprising a pharmaceutically acceptable carrier and a compound of claim 1 or a pharmaceutically acceptable salt form thereof.

5. A method of inhibiting hepatitis C nonstructural protein-3 (HCV NS3) protease comprising contacting a compound of claim 1 for a time and under conditions effective to inhibit HCV NS3 protease.

6. A method of inhibiting hepatitis C nonstructural protein-3 (HCV NS3) protease comprising administering a compound of claim 1 to a mammal in need thereof for a time and under conditions effective to inhibit HCV NS3 protease.

* * * * *